US009968667B2

(12) United States Patent
Huang et al.

(10) Patent No.: US 9,968,667 B2
(45) Date of Patent: May 15, 2018

(54) TARGETS AND COMPOSITIONS FOR USE IN DECONTAMINATION, IMMUNOPROPHYLAXIS, AND POST-EXPOSURE THERAPY AGAINST ANTHRAX

(71) Applicant: Altimmune Inc., Gaithersburg, MD (US)

(72) Inventors: Chun-Ming Huang, Gaithersburg, MD (US); JianFeng Zhang, Gaithersburg, MD (US); De-Chu Tang, Gaithersburg, MD (US)

(73) Assignee: Altimmune Inc., Gaithersburg, MD (US)

( * ) Notice: Subject to any disclaimer, the term of this patent is extended or adjusted under 35 U.S.C. 154(b) by 0 days. days.

(21) Appl. No.: 14/870,570

(22) Filed: Sep. 30, 2015

(65) Prior Publication Data
US 2016/0114020 A1    Apr. 28, 2016

Related U.S. Application Data

(63) Continuation of application No. 10/889,197, filed on Jul. 12, 2004, now abandoned.

(60) Provisional application No. 60/486,369, filed on Jul. 11, 2003.

(51) Int. Cl.
| | |
|---|---|
| *A61K 39/07* | (2006.01) |
| *C07K 14/32* | (2006.01) |
| *C12N 7/00* | (2006.01) |
| *A61K 39/00* | (2006.01) |

(52) U.S. Cl.
CPC .............. *A61K 39/07* (2013.01); *C07K 14/32* (2013.01); *C12N 7/00* (2013.01); *A61K 2039/523* (2013.01); *A61K 2039/5256* (2013.01); *A61K 2039/53* (2013.01); *A61K 2039/543* (2013.01); *A61K 2039/552* (2013.01); *A61K 2039/57* (2013.01); *C12N 2710/10043* (2013.01)

(58) Field of Classification Search
None
See application file for complete search history.

(56) References Cited

U.S. PATENT DOCUMENTS

| | | | |
|---|---|---|---|
| 6,114,148 | A | 9/2000 | Seed et al. |
| 6,348,450 | B1 | 2/2002 | Tang et al. |
| 6,716,823 | B1 | 4/2004 | Tang et al. |
| 2002/0051791 | A1 | 5/2002 | Galloway et al. |

OTHER PUBLICATIONS

Cohen, et al. "Attenuated Nontoxinogenic and Nonencapsulated Recombinant Bacillus Anthracis Spore Vaccines Protect Against Anthrax" Infection and Immunity, 2000, 68(8):4549-4558.
Grandvalet, et al. "Identification of Genes Involved in the Activation of the Bacillus Thuringiensis inhA Metalloprotease Gene At the Onset of Sporulation" Microbiology, 2001, 147:1805-1813.
Guttmann, et al. "Phenotypic and Genotypic Comparisons of 23 Strains From the Bacillus Cereus Complex for a Selection of Known and Putative B. Thuringiensis Virulence Factors" FEMS Microbiology Letters, 2000, 188:7-13.
Huang, et al. "Identification of Bacillus Anthracis Proteins Associated With Germination and Early Outgrowth by Proteomic Profiling of Anthrax Spores" Proteomics, 2004, 4:2653-2661.
Huang, et al. "Proteomics Reveals That Proteins Expressed During the Early Stage of Bacillus Anthracis Infection Are Potential Targets for the Development of Vaccines and Drugs" Geno. Prot. Bioinfo. 2004, 2(3):143-151.
Jedrzejas, "The Structure and Function of Novel Proteins of Bacillus Anthracis and Other Spore Forming Bacteria: Development of Novel Prophylactic and Therapeutic Agents" Critical Reviews in Biochemistry and Molecular Biology, 2002, 37(5):339-373.
Jedrzejas, Three-Dimensional Structure and Molecular Mechanism of Novel Enzymes of Spore-Forming Bacteria, Med. Sci. Monit, 2002, 8(8):RA183-190.
Keitel et al. "Recombinant protective antigen 102 (rPA102): profile of a second-generation anthrax vaccine" Expert Rev. Vaccines, 2006, 5(4):417-430.
Leppla et al. "Development of an improved vaccine for anthrax" The Journal of Clinical Investigation, 2002, 110(2):141-144.
Lovgren, et al. "Molecular Characterization of Immune Inhibitor A, A Secreted Virulence Protease From Bacillus Thuringiensis" Molecular Microbiology, 1990, 4(12):2137-2146.
Mock, et al. "Anthrax" Annu. Rev. Microbiol., 2001, vol. 55: 647-71.
Murakami, et al., "A Single Short Stretch of Homology Between Adenoviral Vector and Packaging Cell Line Can Give Rise to Cytopathic Effect-Inducing, Helper-Dependent E1-Positive Particles" Human Gene Therapy, 2002, 13:909-920.
Pitt et al., "In vitro correlate of immunity in a rabbit model of inhalational anthrax*" Vaccine, 2001, 19:4768-4773.
Price et al., "Protection against Anthrax Lethal Toxin Challenge by Genetic Immunization with a Plasmid Encoding the Lethal Factor Protein" Infection and Immunity, 2001, 69(7):4509-4515.
Purcell et al. "Dissecting the Role of Peptides in the Immune Response: Theory, Practice and the Application to Vaccine Design" Journal of Peptide Science, 2003, 9:255-281.

(Continued)

*Primary Examiner* — Nancy A Treptow
(74) *Attorney, Agent, or Firm* — Vedder Price P.C.; Thomas J. Kowalski; Deborah L. Lu

(57) ABSTRACT

The present invention relates to the decontamination of anthrax spores, prophylaxis and treatment of anthrax infections and, more particularly, to compounds that act as specific inhibitors of *B. anthracis* germination/outgrowth-associated proteins, methods and means for making such inhibitors and their use as pharmaceuticals and/or vaccines. The invention also relates to the prophylaxis and treatment of anthrax infections and, more particularly, to vaccines and compositions that comprise *B. anthracis* antigens, epitopes, proteins, or nucleic acid molecules, including anthrax protective antigen, anthrax lethal factor, anthrax edema factor and anthrax proteins associated with spore germination and outgrowth, as well as methods and means for making such compositions and their use pharmaceuticals and/or vaccines.

12 Claims, 25 Drawing Sheets

(56) References Cited

OTHER PUBLICATIONS

Read, et al. "Comparative Genome Sequencing for Discovery of Novel Polymorphisms in Bacillus Anthracis" Science, 2002, 296:2028-2033.
Read, et al. "The Genome Sequence of Bacillus Anthracis Ames and Comparison to Closely Related Bacteria" Nature, 2003, 423:81-86.
Shi, et al. "Protection against Tetanus by Needle-Free Inoculation of Adenovirus-Vectored Nasal and Epicutaneous Vaccines" Journal of Virology, 2001, 75(23):11474-11482.
Welkos, et al. "In-Vitro Characterisation of the Phagocytosis and Fate of Anthrax Spores in Macrophages and the Effects of Anti-PA Antibody" J. Med. Microbiol. , 2002, 51:821-831.
Welkos, et al. "The Role of Antibodies to Bacillus Anthracis and Anthrax Toxin Components in Inhibiting the Early Stages of Infection by Anthrax Spores", Microbiology, 2001, 147: 1677-1685.

SEQUENCE LISTING

```
<160> NUMBER OF SEQ ID NOS: 44

<210> SEQ ID NO 1
<211> LENGTH: 10
<212> TYPE: PRT
<213> ORGANISM: Bacillus anthracis

<400> SEQUENCE: 1

Leu Gly Asp Asp Ala Ile Trp Ser His Arg
1               5                   10

<210> SEQ ID NO 2
<211> LENGTH: 9
<212> TYPE: PRT
<213> ORGANISM: Bacillus anthracis

<400> SEQUENCE: 2

Ser His Asn Tyr Tyr Val Glu Trp Arg
```

```
<210> SEQ ID NO 3
<211> LENGTH: 13
<212> TYPE: PRT
<213> ORGANISM: Bacillus anthracis

<400> SEQUENCE: 3

Gly Thr Tyr Thr Tyr Asn Gly Leu Ala Gly Val Pro Lys
1               5                   10

<210> SEQ ID NO 4
<211> LENGTH: 12
<212> TYPE: PRT
<213> ORGANISM: Bacillus anthracis

<400> SEQUENCE: 4

Thr Tyr Ile Asn Gln Gln Ile Pro Asp Ala Gly Arg
1               5                   10

<210> SEQ ID NO 5
<211> LENGTH: 10
<212> TYPE: PRT
<213> ORGANISM: Bacillus anthracis

<400> SEQUENCE: 5

Lys Ser His Asn Tyr Tyr Val Glu Trp Arg
1               5                   10

<210> SEQ ID NO 6
<211> LENGTH: 12
<212> TYPE: PRT
<213> ORGANISM: Bacillus anthracis

<400> SEQUENCE: 6

Val Leu Val Leu Leu Val Glu Tyr Ala Asp Phe Lys
1               5                   10

<210> SEQ ID NO 7
<211> LENGTH: 14
<212> TYPE: PRT
<213> ORGANISM: Bacillus anthracis

<400> SEQUENCE: 7

Ile Ala Gly Thr Thr Pro Thr Ser Phe Ser Pro Gln Asn Lys
1               5                   10

<210> SEQ ID NO 8
<211> LENGTH: 14
<212> TYPE: PRT
<213> ORGANISM: Bacillus anthracis

<400> SEQUENCE: 8

Gly Ile Gly Leu Ala Thr Tyr Leu Asp Gln Ser Val Thr Lys
1               5                   10

<210> SEQ ID NO 9
<211> LENGTH: 15
<212> TYPE: PRT
<213> ORGANISM: Bacillus anthracis

<400> SEQUENCE: 9

Ala Ala Asp Tyr Gly Ala Asp Ala Ala Thr Gly His Asp Asn Lys
1               5                   10                  15
```

```
<210> SEQ ID NO 10
<211> LENGTH: 14
<212> TYPE: PRT
<213> ORGANISM: Bacillus anthracis

<400> SEQUENCE: 10

Val Val Phe Ser Asp Asp Ala Glu Gly Thr Pro Gln Phe Lys
1               5                   10

<210> SEQ ID NO 11
<211> LENGTH: 16
<212> TYPE: PRT
<213> ORGANISM: Bacillus anthracis

<400> SEQUENCE: 11

Phe Glu Val Val Gly Gln Ala Asp Asp Asn Ser Ala Gly Ala Val Arg
1               5                   10                  15

<210> SEQ ID NO 12
<211> LENGTH: 16
<212> TYPE: PRT
<213> ORGANISM: Bacillus anthracis

<400> SEQUENCE: 12

Trp Thr Val Gly Pro Lys Pro Phe Pro Ile Glu Gly Thr Gln Ala Lys
1               5                   10                  15

<210> SEQ ID NO 13
<211> LENGTH: 18
<212> TYPE: PRT
<213> ORGANISM: Bacillus anthracis

<400> SEQUENCE: 13

Ala Ala Asp Tyr Gly Ala Asp Ala Ala Thr Gly His Asp Asn Lys Gly
1               5                   10                  15

Pro Lys

<210> SEQ ID NO 14
<211> LENGTH: 17
<212> TYPE: PRT
<213> ORGANISM: Bacillus anthracis

<400> SEQUENCE: 14

Phe Gln Ile Ala Asp Ala Ala Phe Ser Phe Asp Lys Thr Pro Ala Trp
1               5                   10                  15

Lys

<210> SEQ ID NO 15
<211> LENGTH: 22
<212> TYPE: PRT
<213> ORGANISM: Bacillus anthracis

<400> SEQUENCE: 15

Gly Asp Asp Leu His Thr Lys Leu Glu Thr Pro Leu Phe Asp Leu Thr
1               5                   10                  15

Asn Ala Thr Thr Ala Lys
            20

<210> SEQ ID NO 16
<211> LENGTH: 27
<212> TYPE: PRT
<213> ORGANISM: Bacillus anthracis
```

```
<400> SEQUENCE: 16

Ser Leu Tyr Glu Ile Glu Ala Glu Tyr Asp Phe Leu Glu Val His Ala
1               5                   10                  15

Val Thr Glu Asp Gly Gln Gln Thr Leu Ile Glu
            20                  25

<210> SEQ ID NO 17
<211> LENGTH: 9
<212> TYPE: PRT
<213> ORGANISM: Bacillus anthracis

<400> SEQUENCE: 17

Asp Leu Lys Pro Gly Asp Ser Val Lys
1               5

<210> SEQ ID NO 18
<211> LENGTH: 7
<212> TYPE: PRT
<213> ORGANISM: Bacillus anthracis

<400> SEQUENCE: 18

Phe Leu Trp Asn Trp Asp Lys
1               5

<210> SEQ ID NO 19
<211> LENGTH: 10
<212> TYPE: PRT
<213> ORGANISM: Bacillus anthracis

<400> SEQUENCE: 19

Gly Asp Asn Ala Gly Glu Asp Phe Gly Lys
1               5                   10

<210> SEQ ID NO 20
<211> LENGTH: 13
<212> TYPE: PRT
<213> ORGANISM: Bacillus anthracis

<400> SEQUENCE: 20

Asp Val Lys Gly Asp Asn Ala Gly Glu Asp Phe Gly Lys
1               5                   10

<210> SEQ ID NO 21
<211> LENGTH: 13
<212> TYPE: PRT
<213> ORGANISM: Bacillus anthracis

<400> SEQUENCE: 21

Gly Asp Asn Ala Gly Glu Asp Phe Gly Lys His Val Lys
1               5                   10

<210> SEQ ID NO 22
<211> LENGTH: 15
<212> TYPE: PRT
<213> ORGANISM: Bacillus anthracis

<400> SEQUENCE: 22

Gln Ser Glu Pro Val Tyr Glu Thr Thr Leu Ala Asp Leu Gln Lys
1               5                   10                  15

<210> SEQ ID NO 23
<211> LENGTH: 19
<212> TYPE: PRT
<213> ORGANISM: Bacillus anthracis
```

```
<400> SEQUENCE: 23

Glu Val Ser Asn Asn Thr Phe Ala Ala Gly Thr Leu Asp Leu Thr Leu
1               5                   10                  15

Asp Pro Lys

<210> SEQ ID NO 24
<211> LENGTH: 18
<212> TYPE: PRT
<213> ORGANISM: Bacillus anthracis

<400> SEQUENCE: 24

Thr Asp Pro Asp Leu Leu Ala Gln Asp Ile Phe Ala Pro Glu Trp Gly
1               5                   10                  15

Glu Lys

<210> SEQ ID NO 25
<211> LENGTH: 12
<212> TYPE: PRT
<213> ORGANISM: Bacillus anthracis

<400> SEQUENCE: 25

Ser Leu Leu Pro Ala Gly Phe Thr Phe Gly Glu Lys
1               5                   10

<210> SEQ ID NO 26
<211> LENGTH: 11
<212> TYPE: PRT
<213> ORGANISM: Bacillus anthracis

<400> SEQUENCE: 26

Glu Arg Glu Glu Glu Gly Ile Ile Ile Thr Lys
1               5                   10

<210> SEQ ID NO 27
<211> LENGTH: 14
<212> TYPE: PRT
<213> ORGANISM: Bacillus anthracis

<400> SEQUENCE: 27

Lys Pro Gly Asn Tyr Leu Thr Leu Glu Val Gln Gly Ile Arg
1               5                   10

<210> SEQ ID NO 28
<211> LENGTH: 15
<212> TYPE: PRT
<213> ORGANISM: Bacillus anthracis

<400> SEQUENCE: 28

Thr Lys Pro Asp Phe Val Ile Ala Ile Asp Ala Leu Ala Ala Arg
1               5                   10                  15

<210> SEQ ID NO 29
<211> LENGTH: 16
<212> TYPE: PRT
<213> ORGANISM: Bacillus anthracis

<400> SEQUENCE: 29

Asn Met Phe Leu Gly Ala Val Gly Thr Leu Glu Asp Glu Glu Lys Arg
1               5                   10                  15

<210> SEQ ID NO 30
<211> LENGTH: 20
```

```
<212> TYPE: PRT
<213> ORGANISM: Bacillus anthracis

<400> SEQUENCE: 30

Val Asn Ser Thr Ile Gln Ser Asp Thr Gly Ile His Pro Gly Ser Gly
1               5                   10                  15

Val Gly Asn Lys
            20

<210> SEQ ID NO 31
<211> LENGTH: 10
<212> TYPE: PRT
<213> ORGANISM: Bacillus anthracis

<400> SEQUENCE: 31

Ala Ala Ala Leu Thr Val Ala Gln Ile Ser
1               5                   10

<210> SEQ ID NO 32
<211> LENGTH: 13
<212> TYPE: PRT
<213> ORGANISM: Bacillus anthracis

<400> SEQUENCE: 32

Ile Val Pro Val Glu Leu Ile Gly Thr Val Asp Ile Arg
1               5                   10

<210> SEQ ID NO 33
<211> LENGTH: 20
<212> TYPE: PRT
<213> ORGANISM: Bacillus anthracis

<400> SEQUENCE: 33

Phe Phe Leu Ser Leu Gly Thr Pro Ala Asn Ile Ile Pro Gly Ser Gly
1               5                   10                  15

Thr Ala Val Arg
            20

<210> SEQ ID NO 34
<211> LENGTH: 25
<212> TYPE: PRT
<213> ORGANISM: Bacillus anthracis

<400> SEQUENCE: 34

Ala Gly Ile Tyr Gln Ile Ser Tyr Thr Leu Thr Ile Ser Leu Asp Asn
1               5                   10                  15

Ser Pro Val Ala Pro Glu Ala Gly Arg
            20                  25

<210> SEQ ID NO 35
<211> LENGTH: 27
<212> TYPE: PRT
<213> ORGANISM: Bacillus anthracis

<400> SEQUENCE: 35

Ser Asn Val Ile Gly Thr Gly Glu Val Asp Val Ser Ser Gly Val Ile
1               5                   10                  15

Leu Ile Asn Leu Asn Pro Gly Asp Leu Ile Arg
            20                  25

<210> SEQ ID NO 36
<211> LENGTH: 12
<212> TYPE: PRT
```

```
<213> ORGANISM: Bacillus anthracis

<400> SEQUENCE: 36

Ala Glu Ala Ala Gln Phe Ile Ala Leu Thr Asp Lys
1               5                   10

<210> SEQ ID NO 37
<211> LENGTH: 13
<212> TYPE: PRT
<213> ORGANISM: Bacillus anthracis

<400> SEQUENCE: 37

Ala Glu Ala Ala Gln Phe Ile Ala Leu Thr Asp Lys Lys
1               5                   10

<210> SEQ ID NO 38
<211> LENGTH: 12
<212> TYPE: PRT
<213> ORGANISM: Bacillus anthracis

<400> SEQUENCE: 38

Leu Ser Ala Asp Asp Val Thr Leu Glu Gly Asp Lys
1               5                   10

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agtacaagtg ctggacctac ggttccagac                                    30

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcctatctca tagcctttt tagaaaagat                                     30

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tatccttcta aaaacttggc gccaatcgca                                    30

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
```

```
gatcactagg attaaccgcc gctatccgcc                                              30

<210> SEQ ID NO 43
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
ccataacccc ttggggcctc taaacgggtc ttgaggggtt ttttgctgaa aggagg               56

<210> SEQ ID NO 44
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tcgaggtatt ggggaacccc ggagatttgc ccagaactcc ccaaaaaacg actttcctcc          60
```

TARGETS AND COMPOSITIONS FOR USE IN DECONTAMINATION, IMMUNOPROPHYLAXIS, AND POST-EXPOSURE THERAPY AGAINST ANTHRAX

CROSS-REFERENCE TO RELATED APPLICATIONS

This application is a continuation of U.S. application Ser. No. 10/889,197 filed Jul. 12, 2004, which claims priority to U.S. Provisional Application 60/486,369 filed Jul. 11, 2003. Reference is also made to the following jointly-owned applications and patents: U.S. patent application Ser. No. 10/346,021 filed Jan. 16, 2003, which is a continuation-in-part of U.S. patent application Ser. No. 10/116,963, filed Apr. 5, 2002, which is a continuation-in-part of U.S. patent application Ser. No. 10/052,323, filed Jan. 18, 2002, which is a continuation-in-part of U.S. patent application Ser. No. 09/563,826, filed May 3, 2000 (issued Feb. 19, 2002 as U.S. Pat. No. 6,348,450), which claims priority from U.S. Provisional Application No. 60/132,216, filed May 3, 1999, and is also a continuation-in-part of U.S. patent application Ser. No. 09/533,149, filed Mar. 23, 2000, which in turn is a continuation of U.S. patent application Ser. No. 09/402,527, filed on Aug. 13, 2000. Each of these above-referenced applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("application cited documents"). Each of the application cited documents, and each document cited or referenced in the application cited documents, is hereby incorporated herein by reference.

GOVERNMENT SUPPORT

Research carried out in connection with this invention may have been supported in part by grants from Grant No. N00014-01-1-0945 awarded by the Office of Naval Research and Grant No. 1-R43-AI-47558-01A2 awarded by the National Institutes of Health. The United States government may have certain rights in the invention.

FIELD OF THE INVENTION

The present invention relates generally to the fields of bacteriology, immunology, and vaccine technology.

The present invention also relates to *Bacillus anthracis* proteins as novel targets and compositions for use in decontamination, immunoprophylaxis, and post-exposure therapy against anthrax. The invention relates to the administration of these proteins by any number of routes including, but not limited to, mucosal, e.g., intranasal, perlingual, buccal, oral, oral cavity, intravenous, intramuscular, transdermal or intracutaneous, when used in immunoprophylaxis or post-exposure therapy. The invention further relates to methods of non-invasive immunization in an animal and/or methods of inducing an immunological, e.g., systemic immune response or a therapeutic, e.g., a systemic therapeutic response, in an animal against anthrax, products therefrom and uses for the methods and products therefrom. The invention yet further relates to such methods comprising contacting the nasal mucosa (e.g. via nasal spray) or the skin of the animal with a vector in an amount effective to induce the response, e.g., systemic immune response against anthrax in the animal. Even further, the invention relates to such methods wherein the vector comprises and expresses an exogenous nucleic acid molecule encoding an epitope or gene product of interest, e.g., an anthrax antigen. Still further, the invention relates to such methods wherein the response, e.g., systemic immune or therapeutic response, can be to or from the epitope or gene product. Even further still, the invention relates to such methods wherein the vector is non-replicative.

The invention yet further still relates to such methods wherein the nucleic acid molecule can be exogenous to the vector. The invention also relates to such methods wherein the exogenous nucleic acid molecule encodes one or more of an antigen or portion thereof, e.g., one or more of an epitope of interest from *Bacillus anthracis*, e.g., anthrax protective antigen, anthrax lethal factor or anthrax proteins associated with spore germination or outgrowth.

Even further, the invention relates to such methods wherein the immune response can be induced by the vector expressing the nucleic acid molecule in the vector or in the animal's cells, e.g., cells lining a mucosal surface, such as the nasal mucosal surface, epidermal cells including but not limited to keratinocytes, melanocytes, langerhans cells, merkel cells and hair matrix cells. The invention still further relates to such methods wherein the immune response can be against *Bacillus anthracis*.

Also, the invention relates to compositions used in the methods. For instance, the invention relates to a prophylactic vaccine or a therapeutic vaccine or an immunological composition comprising the vector, wherein the vector can be replicative or non-replicative.

The invention additionally relates to such methods and compositions therefor wherein the animal can be a vertebrate, e.g., a mammal, advantageously a mammal such as a human or a companion or domesticated or food- or feed-producing or livestock or game or racing or sport animal, for instance, a cow, a horse, a dog, a cat, a goat, a sheep or a pig.

The invention further relates to such methods and compositions therefor wherein the vector can be one or more of a viral, including viral coat, e.g., with some or all viral genes deleted therefrom, bacterial, protozoan, transposon, and retrotransposon, and DNA vector, e.g., a recombinant vector; an adenovirus, such as an adenovirus defective in its E1 and/or E3 and/or E4 region(s) and/or all adenoviral genes.

The invention further relates to such methods and compositions therefore wherein the vector can be non-replicative.

The invention further relates to mucosal, e.g., intranasal, perlingual, buccal, oral, oral cavity, administration of adenovirus defective in its E1 and/or E3 and/or E4 region(s) and/or all adenoviral genes, advantageously defective in its E1 and E3 regions, e.g., such an adenovirus comprising an exogenous or heterologous nucleic acid molecule, such as an exogenous or heterologous nucleic acid molecule encoding an epitope of interest of an anthrax, e.g., one or more anthrax epitopes of interest and/or one or more anthrax antigens. Such an administration can be a method to induce an immunological response, such as a protective immunological response. The adenovirus in this instance can be a human adenovirus. The adenovirus can be another type of adenovirus, such as a canine adenovirus.

The invention still further relates to such methods encompassing applying a delivery device including the vector to the skin of the animal, as well as such a method further including disposing the vector in and/or on the delivery device; and, to such delivery devices.

The invention yet further relates to such methods wherein the vector can have all viral genes deleted therefrom, as well as to such vectors.

The invention yet further relates to such methods wherein the vector can be non-replicative bacterial vectors expressing *Bacillus anthracis* antigens, for example, wherein the bacterial vector has been irradiated.

In addition, the invention relates to immunological products generated by the expression and the expression products, as well as in in vitro and ex vivo uses thereof.

The invention also relates to such methods wherein the *Bacillus anthracis* protective antigen or fragments thereof are expressed from the viral or bacterial vectors.

The invention further relates to such methods wherein an immunogenic but atoxic *Bacillus anthracis* lethal factor is expressed from the viral or bacterial vectors.

The invention yet further relates to such methods wherein immunogenic but atoxic fragments of the *Bacillus anthracis* immune inhibitor A, Hypothetical protein 1 (Germaxin), Hypothetical proteins 2, 4, and 5, GPR-like spore protease, CIP protease, cysteine synthase A, heat-shock proteins 70 and 60, class 1 heat shock protein, elongation factor G and Ts, RNA polymerase, acetate kinase, delta-1-pyrroline-5-carb-oxylate dehydrogenase, pyruvate dehydrogenase, alkyl hydroperoxide reductase, oxidoreductase, elonase, ATP synthase, fructose-bisphosphate aldolase, triosephosphate isomerase, glyceraldehyde 3-physphate dehydrogenase, sugar ABC transporter, band 7, and alcohol dehydrogenase are expressed from the viral or bacterial vectors.

The invention still further relates to such methods wherein targeting the *Bacillus anthracis* alanine racemace induces pre-mature spore germination for immunoprophylaxis and post-exposure therapy against anthrax, and decontamination of areas covered by anthrax spores.

BACKGROUND

Anthrax is a zoonotic illness that has been recognized for centuries. In the 1870s, Robert Koch demonstrated for the first time the bacterial origin of a specific disease, with his studies on experimental anthrax, and also discovered the spore stage that allows persistence of the organism in the environment. Shortly afterward, *Bacillus anthracis* was recognized as the cause of woolsorter disease, now known as inhalational anthrax. The development of vaccines against anthrax began in 1880 with William Greenfield's successful immunization of livestock against anthrax and Louis Pasteur's 1881 trial of a heat-cured anthrax vaccine in sheep.

*Bacillus anthracis* is a large, gram-positive, sporulating rod, with square or concave ends. Growing readily on sheep blood agar, *B. anthracis* forms rough, gray-white colonies of four to five micrometer, with characteristic comma-shaped or "comet-tail" protrusions. Several tests are helpful in differentiating *B. anthracis* from other *Bacillus* species. *Bacillus anthracis* is characterized by an absence of the following: hemolysis, motility, growth on phenylethyl alcohol blood agar, gelatin hydrolysis, and salicin fermentation. *Bacillus anthracis* may also be identified by the API-20E and API-50CHB systems used in conjunction with the previously mentioned biochemical tests. Definitive identification is based on immunological demonstration of the production of protein toxin components and the poly-D-glutamic acid capsule, susceptibility to a specific bacteriophage, and virulence for mice and guinea pigs.

Naturally occurring human cases of anthrax are invariably zoonotic in origin, with no convincing data to suggest that human-to-human transmission has ever taken place. Primary disease takes one of three forms: (1) cutaneous, the most common, which results from contact with an infected animal or animal product; (2) inhalational, which is much less common and results from spore deposition in the lungs; and (3) gastrointestinal, which is due to ingestion of infected meat. Most literature cites cutaneous disease as constituting the large majority (up to 95%) of naturally occurring exposure cases.

Anthrax has been studied for use as a biological weapon for over 80 years, with the transmission of spores through air as the most likely method of transmission, resulting in inhalational anthrax. Due to the rapidly fatal hemorrhagic mediastinitis caused by inhalation of anthrax spores, the dissemination of airborne spores in a populated area could be devastating.

Disease occurs when spores enter the body, germinate to the bacillary form, and multiply. In cutaneous disease, spores gain entry through cuts, abrasions, or in some cases through certain species of biting flies. Germination is thought to take place in macrophages, and toxin release results in edema and tissue necrosis but little or no purulence, probably because of inhibitory effects of the toxins on leukocytes. Generally, cutaneous disease remains localized, although if untreated it may become systemic in up to 20% of cases, with dissemination via the lymphatics. In the gastrointestinal form, *B. anthracis* is ingested in spore-contaminated meat, and may invade anywhere in the gastrointestinal tract. Transport to mesenteric or other regional lymph nodes and replication occur, resulting in dissemination, bacteremia, and a high mortality rate. As in other forms of anthrax, involved nodes show an impressive degree of hemorrhage and necrosis.

The pathogenesis of inhalational anthrax is more fully studied and understood than that of cutaneous or gastrointestinal anthrax. Inhaled spores are ingested by pulmonary macrophages and carried to hilar and mediastinal lymph nodes, where they germinate and multiply, elaborating toxins and overwhelming the clearance ability of the regional nodes. Bacteremia occurs, and death soon follows.

Penicillin remains the drug of choice for treatment of susceptible strains of anthrax, with ciprofloxacin and doxycycline employed as suitable alternatives. Some data in experimental models of infection suggest that the addition of streptomycin to penicillin may also be helpful. Penicillin resistance remains extremely rare in naturally occurring strains; however, the possibility of resistance should be suspected in a biological warfare attack. Since reports in 1999 that an anthrax strain had been engineered to be resistant to the tetracycline and penicillin classes of antibiotics, ciprofloxacin is the recommended treatment for adults with suspected inhalational anthrax. The more severe forms require intensive supportive care and have a high mortality rate despite optimal therapy.

The virulence of *B anthracis* is mediated by two plasmids, pXO1 and pXO2, which encodes genese involved in toxin production and capsule formation, respectively. The pXO1 genes pagA, lef, and cya encode the tripartite toxin protective antigen (PA)-lethal factor (LF)-edema factor (EF) associated with *B. anthracis* pathogenicity (Inglesby 2002). Production of PA-LF-EF peaks during the late exponential phase of vegetative growth (Liu 2004). The importance of a toxin in pathogenesis was demonstrated in the early 1950s, when sterile plasma from anthrax-infected guinea pigs caused disease when injected into other animals (Smith and Keppie 1954). It has since been shown that the anthrax toxins are composed of three entities, which in concert lead to some of the clinical effects of anthrax (Stanley and Smith 1961; Beall 1962). The first of these, protective antigen (PA), is an 83 kd protein so named because it is the main protective constituent of anthrax vaccines. Protective antigen binds to a cellular receptor (Bradley 2001) and is proteolytically cleaved by cell surface furin to produce a 63-KD fragment (PA63). A second binding domain is then exposed on the 63 kd remnant, which combines with either edema factor (EF), an 89 kd protein, to form edema toxin, or lethal factor (LF), a 90 kd protein, to form lethal toxin (Leppla 1990). This occurs through the receptor-bound PA63, which oligomerizes to a heptamer and acts to translocate the catalytic moieties of the toxin, LF and/or EF, from endosomes to the cytosol (Singh 1999). Edema factor, a calmodulin-dependent adenylate cyclase, acts by converting adenosine triphosphate to cyclic adenosine monophosphate. Intracellular cyclic adenosine monophosphate levels are thereby increased and neutrophil functions are impaired, leading to the edema characteristic of the disease (Leppla 1982; Swartz 2001; Inglesby 2002). Lethal factor appears to be a zinc metalloprotease and has been demonstrated to lyse macrophages at high concentration (Bradley 2001), while inducing the release of tumor necrosis factor .alpha. and interleukin 1.beta. at lower concentrations (Friedlander 1986; Hanna 1993), which have been linked to the sudden death in anthrax infection (Swartz 2001; Inglesby 2002).

Although anthrax vaccination dates to the early studies of Greenfield and Pasteur, the "modern" era of anthrax vaccine development began with a toxin-producing, unencapsulated (attenuated) strain in the 1930s. Administered to livestock as a single dose with a yearly booster, the vaccine was highly immunogenic and well tolerated in most species, although somewhat virulent in goats and llamas. This preparation is essentially the same as that administered to livestock around the world today. The first human vaccine was developed in the 1940s from nonencapsulated strains. This live spore vaccine, similar to Sterne's product, is administered by scarification with a yearly booster. Studies show a reduced risk of 5- to 15-fold in occupationally exposed workers (Shlyakhov and Rubinstein 1994).

To date, there have been many attempts to improve the safety profile and immunogenicity of anthrax vaccines by using PA as an antigen. These attempts include the formulation of PA in adjuvants (Ivins 1992), the use of purified PA (Singh 1998), the development of PA-based DNA vaccines (Gu 1999), and the expression of PA in *Salmonella typhimurium* (Coulson 1994).

British and U.S. vaccines were developed in the 1950s and early 1960s, with the U.S. producing an aluminum hydroxide-adsorbed, cell-free culture filtrate of an unencapsulated strain (V770-NP 1-R) containing PA as the major protective immunogen, and the British vaccine an alum-precipitated, cell-free filtrate of a Sterne strain culture. The U.S. vaccine has been shown to induce high levels of antibody only to protective antigen, while the British vaccine induces lower levels of antibody to protective antigen but measurable antibodies against lethal factor and edema factor (Turnbull 1986; Turnbull 1988). Neither vaccine has been examined in a human clinical efficacy trial (Inglesby 2002). A high number of the recipients of the vaccine have reported some type of reaction to vaccination although most were minor. Manufacturer labeling for the current Michigan Department of Public Health anthrax vaccine adsorbed (AVA) product cites a 30% rate of mild local reactions and a 4% rate of moderate local reactions with a second dose.

The current complex dosing schedule for the AVA vaccine consists of 0.5 mL administered subcutaneously at 0, 2, and 4 weeks, and 6, 12, and 18 months, followed by yearly boosters. Animal studies examining the efficacy of available anthrax vaccines against aerosolized exposure have been performed. While some guinea pig studies question vaccine efficacy, primate studies have supported its role. In recent work, rhesus monkeys immunized with 2 doses of the AVA vaccine were challenged with lethal doses of aerosolized *B anthracis* spores. All monkeys in the control group died 3 to 5 days after exposure, while the vaccinated monkeys were protected up to 2 years after immunization (Ivins 1996). Another trial used the AVA vaccine in a 2-dose series with a slightly different dosing interval, and again found it to be protective in all rhesus monkeys exposed to lethal aerosol challenge (Pitt 1996). Thus, available evidence suggests that two doses of the current AVA vaccine should be efficacious against an aerosol exposure to anthrax spores. However, one significant limitation on the use of vaccines is that existing vaccines provide no protection against a number of strains of *B. anthracis*. Additionally, the current requirement for multiple injections resulting local pain and edema suggests an effective alternative is needed (Joellenbeck 2002). The Georgian/Russian anthrax vaccine consists of live spores from a Sterne strain of *B. anthracis* that is administered in the shoulder by scarification. This vaccine also has several undesirable side effects and unknown efficacy (Demicheli 1998). Other alternatives that have been investigated include a highly purified, minimally reactogenic, recombinant protective antigen vaccine using aluminum as well as other adjuvants, cloning the protective antigen gene into a variety of bacteria and viruses, and the development of mutant, avirulent strains of *B. anthracis*.

Further underscoring the need for a new class of anthrax vaccines or remedies is the development of enabling technology capable of engineering *B. anthracis* spores into vectors expressing unpredictable toxins by replacing pXO1 with an artificial plasmid, owing to the dispensability of the pXO1 plasmid for growth of *B. anthracis* (Welkos 2001).

In the 2001 U.S. anthrax attacks, anthrax spores were enclosed in letters and envelopes sent through the mail and resulted in both cutaneous anthrax (11 cases: 7 confirmed, 4 suspected) in those who handled such letters, and inhalational anthrax (11 cases) (Centers for Disease Control and Prevention 2001). Other known experiences with large-scale, non-naturally occurring anthrax exposure are limited to the 1979 accidental release of anthrax spores from a bioweapons factory in Sverdlovsk, Russia.

These recent incidents, which also include the suspected use of biological and chemical weapons during the Persian Gulf War, underscore the threat of biological warfare either on the battlefield or by terrorists. Anthrax has been the focus of much attention as a potential biological warfare agent for at least six decades, and modeling studies have shown the potential for use in an offensive capacity. Dispersal experiments with the simulant *Bacillus globigii* in the New York subway system in the 1960s suggested that release of a similar amount of *B. anthracis* during rush hour would result in 10,000 deaths. On a larger scale, the World Health Organization estimated that 50 kg of *B. anthracis* released upwind of a population center of 500,000 would result in up to 95,000 fatalities, with an additional 125,000 persons incapacitated (Huxsoll 1989). Both on the battlefield and in a terrorist strike, *B. anthracis* has the attribute of being potentially undetectable until large numbers of seriously ill individuals present with characteristic signs and symptoms of inhalational anthrax. Given these findings, efforts to prevent the disease or to ameliorate or treat its effects are of obvious importance. The U.S. military's current M17 and M40 gas masks provide excellent protection against the 1 to 5 .mu.m particulates needed for a successful aerosol attack. Assuming a correct fit, these masks would be highly effective if in use at the time of exposure. Some protection might also be afforded by various forms of shelter.

Until recently, the AVA anthrax vaccine was supplied only to the Department of Defense for vaccination of soldiers. This use has recently expanded to include vaccination of reporters who would face potential exposure while covering any future warfare or terrorist situations. At this time, vaccination of the general public is not encouraged by the Centers for Disease Control.

Due to the limited use of the available anthrax vaccines and their limited ability to prevent infection caused by numerous anthrax strains, it is therefore apparent that while certain prophylactic and treatment schemes may prove useful in preventing or ameliorating anthrax infections, there remains a compelling need to improve the arsenal of techniques and agents available for this purpose.

Contemporary anti-anthrax remedies focus on the three-component toxin system protective antigen (PA)-lethal factor (LF)-edema factor (EF) that is produced during multiplication of the vegetative form of *B. anthracis* in the host (Mock and Fouet 2001). The dissemination of an odorless and invisible aerosol containing PA-free anthrax spores encoding exogenous toxins would be devastating, as all PA-targeted anthrax vaccines (Price 2001; Welkos 2001; Joellenbeck 2002; Rhie 2003; Tan 2003) and remedies (Sellman 2001) are ineffective in protection against anthrax strains without PA. Furthermore, although targeting PA has proven effective to varying degrees of success in counteracting anthrax, it is unknown at this time whether any of the PA-targeted methods can protect humans against inhalational anthrax (Inglesby 2002) during a massive onslaught with airborne anthrax spores used as a bioweapon.

A solution to this dilemma might be found at the level of spore germination and early outgrowth.

The present invention identifies *B. anthracis* spore proteins as novel targets in decontamination, immunoprophylaxis, and post-exposure therapy against anthrax.

During the life cycle of *B. anthracis*, the germinating spores are likely the weakest link in the cycle, akin to plant seedlings and animal babies, and hence are the easiest vaccine target. Additionally, germination is an upstream event during the life cycle of *B. anthracis*; arrest of spore germination will preclude any downstream events including the production of PA-LF-EF. Consequently, blocking spore germination and early outgrowth provides a logical means to arrest bioengineered anthrax spores regardless of the exogenous toxin they may encode.

Additionally as previously mentioned, PA, LF, and EF are encoded by a plasmid in *B. anthracis*. Technology that enables the replacing of this plasmid with others encoding other unpredictable toxins (e.g., tetanus toxin, cobratoxin, etc.) is not beyond reach. Bioterrorists may bypass any PA-targeted remedies by launching an attack with anthrax spores producing toxins other than PA-LF-EF. Therapies that target the germinating spores would prevent the production of such toxins from occurring. Arrest of spore germination with vaccines and/or inhibitors overall may prevent utilization of anthrax spores as bioweapons.

Furthermore, factors associated with spore germination or outgrowth may be highly conserved and can hardly be altered, making these proteins an ideal target that should be conserved between strains. In contrast, vegetative cells undergo mutations over time. Development of antibiotic resistance in vegetative cells is one such example.

The present invention also provides a new composition for vaccination against *Bacillus anthracis*, using adenovirus and bacterium vectored nasal and epicutaneous vaccines that can provide protection to large numbers of people in a timely manner by non-medical personnel.

There are several noteworthy reasons for utilizing recombinant Ad vector as a vaccine carrier. These include (i) Ad vectors are capable of transducing both mitotic and postmitotic cells in situ (Shi 1999), (ii) stocks containing high titers of virus (greater than 10.sup.11 pfu [plaque-forming units] per ml) can be prepared, making it possible to transduce cells in situ at high multiplicity of infection (MOI), (iii) the vector is safe based on its long-term use as a vaccine, (iv) the virus is capable of inducing high levels of transgene expression (at least as an initial burst), and (v) the vector can be engineered to a great extent with versatility. Recombinant Ad vectors have been utilized as vaccine carriers by intranasal, epicutaneous, intratracheal, intraperitoneal, intravenous, subcutaneous, and intramuscular routes.

Ad-vectored nasal vaccine appears to be more effective in eliciting an immune response than injection of DNA or topical application of Ad (Shi 2001). Previously reported results have shown that the potency of the E1/E3-defective Ad5 vector as a nasal vaccine carrier is not suppressed by any preexisting immunity to Ad (Xiang 1996; Shi 2001).

Furthermore, it is possible to create an epicutaneous vaccine using recombinant *Escherichia coli* vectors as the carrier. Expression of heterologous genes in recombinant *E. coli* vectors about two decades ago (Itakura 1977; Goeddel 1979; Goeddel 1979) allowed *E. coli* cells to be utilized as protein factories for production of exogenous proteins including a variety of vaccines. It was subsequently demonstrated that recombinant plasmid DNA extracted from *E. coli* vectors could be inoculated into animals to elicit an immune response against antigens encoded by the plasmid, the so called genetic immunization or DNA-based vaccination (Tang 1992; Ulmer 1993). Both approaches required the disruption of *E. coli* cells prior to inoculation into animals, in conjunction with subsequent extraction and purification of recombinant protein and DNA, respectively; it is hazardous to inject undisrupted *E. coli* cells into humans as a vaccine due to the presence of endotoxin. It has recently been demonstrated that topical application of live or irradiated *E. coli* cells may be a more potent vaccination modality than injection of DNA. It is also believed that the skin is able to disrupt *E. coli* cells following topical application and the present invention hypothesizes that the antigen may be captured from disrupted *E. coli* cells in the outer layer of skin followed by antigen presentation and the elicitation of protective immunity against pathogens, including *Bacillus anthracis*. Topical application of *E. coli* cells as a vaccination modality does not pose a biosafety concern because the skin is already in frequent contact with *E. coli* cells in the environment. Moreover, the biosafety margin of this modality can be further amplified by making recombinant *E. coli* vectors replication incompetent, for example, with .gamma.-irradiation.

OBJECT AND SUMMARY OF THE INVENTION

The present invention relates to the prophylaxis and treatment of anthrax infections and decontamination of anthrax spores, more particularly, to compounds that act as specific inhibitors or enhancers for *B. anthracis* spore germination, methods and means for making such inhibitors and enhancers and their use as pharmaceuticals, vaccines and/or decontamination agents.

Accordingly, it is an object of the invention described herein to provide compositions that are capable of precisely targeting *B. anthracis* spore proteins without producing significant undesirable side effects.

Another object of the invention relates to the prophylaxis and treatment of anthrax infections and, more particularly, to vaccines and compositions that comprise *B. anthracis* antigens, epitopes, proteins, or nucleic acid molecules, including anthrax protective antigen, anthrax lethal factor, anthrax edema factor and anthrax germination/outgrowth associated proteins, as well as methods and means for making such compositions and their use as pharmaceuticals, vaccines, and/or decontamination agents.

Additionally, it is an object of the invention that viral or bacterial vectors such as *Escherichia coli* or adenovirus may be useful in making the compositions of the present invention and in expressing the *B. anthracis* antigens, epitopes, proteins or nucleic acid molecules of the present invention.

Both non-invasive vaccination onto the skin (NIVS) and intranasal application can improve vaccination schemes because skin and nasal mucosa are immunocompetent tissues and this non-invasive procedure requires no specially trained personnel. Skin-targeted non-invasive gene delivery can achieve localized transgene expression in the skin and the elicitation of immune responses (Tang 1997). These results indicate that vector-based NUVS is a novel and efficient method for the delivery of vaccines. The simple, effective, economical and painless immunization protocol of the present invention should make vaccination less dependent upon medical resources and, therefore, achieve vaccination of large numbers of individuals against anthrax in a timely manner by non-medical personnel.

Accordingly, an object of the invention can be any one or more of: providing a method for inducing an immunological response, e.g., protective immunological response, and/or a therapeutic response in a host or animal, e.g., vertebrate such as mammal, comprising nasally or topically administering a vector that comprises and expresses a nucleic acid molecule encoding a gene product that induces or stimulates the response; such a method wherein the nucleic acid molecule is heterologous and/or exogenous with respect to the host; mucosal, e.g., intranasal, perlingual, buccal, oral, oral cavity administration of adenovirus defective in its E1 and/or E3 and/or E4 region(s) and/or all adenoviral genes, advantageously defective in its E1 and E3 and E4 regions, e.g., such an adenovirus comprising an exogenous or heterologous nucleic acid molecule, such as an exogenous or heterologous nucleic acid molecule encoding an epitope of interest of anthrax, e.g., one or more *Bacillus anthracis* epitiopes of interest and/or one or more *Bacillus anthracis* antigens; such an administration wherein an immunological response, such as a protective immunological response is induced; products for performing such methods; uses for such methods and products, inter alia.

The present invention provides a method of non-invasive immunization in an animal, comprising the step of: contacting skin or nasal, oral, perlingual or buccal mucosa of the animal with a vector in an amount effective to induce an immune response in the animal. The invention also provides a method for immunizing animals comprising the step of skin-targeted non-invasive delivery of a preparation comprising vectors, whereby the vector is taken up by epidermal cells and has an immunogenic effect on vertebrates. The invention further provides a method for immunizing animals by a delivery device, comprising the steps of including vectors in the delivery device and contacting the naked skin of a vertebrate with a uniform dose of vaccines confined within the device, whereby the vector is taken up by epidermal cells for expressing and/or presenting a specific antigen in the immunocompetent skin tissue. The invention further provides a method for immunizing animals by a delivery device, comprising the steps of including vectors in the delivery device and contacting the nasal mucosa of a vertebrate with a uniform dose of vaccines confined within the device, whereby the vector is taken up by the mucosa for expressing and/or presenting a specific antigen in the immunocompetent tissue. The vector may be adenovirus recombinants, DNA/adenovirus complexes, DNA/liposome complexes, bacterial vectors containing recombinant plasmids, or other vectors capable of expressing antigens in the skin or mucosa of a vertebrate.

In a preferred embodiment of the present invention, the vector is non-replicative. For example, the vector can be irradiated.

In an embodiment of the present invention, there is provided a method of inducing an immune response, comprising the step of: contacting skin, or anal, oral perlingual or buccal mucosa of an individual or animal in need of such treatment by topically applying to said skin an immunologically effective concentration of a recombinant vector encoding a gene of interest.

In another embodiment of the present invention, there is provided a method of inducing a protective immune response in an individual or animal in need of such treatment, comprising the step of: contacting the skin or nasal mucosa of said animal by topically applying to said skin an immunologically effective concentration of a vector encoding a gene which encodes an antigen which induces a protective immune effect in said individual or animal following administration. In yet a further embodiment of the invention, contacting the skin may include the use of microneedles or similar devices. For example, "Microfabricated microneedles: a novel approach to transdermal drug delivery" describes the benefits associated with the use of microneedles, and would allow one of skill in the art to practice the present invention in combination with such devices {Henry, 1998 #134}. In certain instances, the use of such devices may be considered "non-invasive."

The invention thus provides methods of non-invasive immunization in an animal and/or methods of inducing an immune, e.g., systemic immune, or therapeutic response in an animal, products therefrom and uses for the methods and products therefrom. The invention further provides such methods comprising contacting skin or nasal mucosa of the animal with a vector in an amount effective to induce the response, e.g., immune response such as systemic immune response or therapeutic response, in the animal. Even further, the invention provides such methods wherein the vector comprises and expresses an exogenous nucleic acid molecule encoding an epitope or gene product of interest. Still further, the invention provides such methods wherein the systemic immune response can be to or from the epitope or gene product.

The invention additionally provides such methods wherein the nucleic acid molecule can be exogenous to the vector. The invention also provides such methods wherein the exogenous nucleic acid molecule encodes one or more of an antigen of interest or portion thereof, e.g., an epitope of interest, from a pathogen; for instance, one or more of anthrax protective antigen, anthrax lethal factor, anthrax edema factor, or *Bacillus anthracis* proteins associated with germianation/outgrowth; and/or a therapeutic and/or an immunomodulatory gene, such as a co-stimulatory gene, a chemokine gene and/or a cytokine gene. See also U.S. Pat. No. 5,990,091, WO 99/60164 and WO 98/00166 and documents cited therein.

Even further, the invention provides such methods wherein the immune response can be induced by the vector expressing the nucleic acid molecule in the vector and/or in the animal's cells, e.g., epidermal cells. The invention still further provides such methods wherein the immune response can be against a pathogen.

Also, the invention provides compositions used in the methods. For instance, the invention provides a prophylactic vaccine or a therapeutic vaccine or an immunological or a therapeutic composition comprising the vector, e.g., for use in inducing or stimulating a response via topical application and/or via mucosal and/or nasal and/or perlingual and/or buccal and/or oral and/or oral cavity administration. The invention also provides compositions comprising a non-replicative vector. Additionally, the invention also provides compositions comprising a vector or a non-replicative vector, in combination with an adjuvant.

The invention additionally provides to such methods and compositions therefor wherein the animal can be a vertebrate, e.g., a mammal, such as human, or a domesticated or companion or feed-producing or food-producing or livestock or game or racing or sport animal such as a cow, a dog, a cat, a goat, a sheep, a horse, or a pig.

The invention further provides such methods and compositions therefor wherein the vector can be one or more of a virus, including viral coat, e.g., with some or all viral genes deleted therefrom, bacterial, protozoan, transposon, retrotransposon, and DNA vector, e.g., a recombinant vector; an adenovirus, such as an adenovirus defective in its E1 and/or E3 and/or E4 region(s) and/or all adenoviral genes. The invention further provides such methods and compositions therefore wherein the vector can be chosen from yeast vectors, insect cells transduced with baculovirus vectors, or tissue culture cells, and wherein the vector is non-replicative. For example, the vector can be irradiated.

The invention further provides such methods and compositions therefor wherein the vector can be an *Escherichia* bacterial vector. Further still, the invention provides such methods and compositions therefor wherein the vector is preferably an *Escherichia coli* bacterial vector.

The invention further provides intranasal and/or mucosal and/or perlingual and/or buccal and/or oral and/or oral cavity administration of adenovirus defective in its E1 and/or E3 and/or E4 region(s) and/or all adenoviral genes, advantageously defective in its E1 and E3 and E4 regions, e.g., such an adenovirus comprising an exogenous or heterologous nucleic acid molecule, such as an exogenous or heterologous nucleic acid molecule encoding an epitope of interest of *Bacillus anthracis*, e.g., one or more of anthrax protective antigen, anthrax lethal factor, anthrax edema factor, or anthrax proteins associated with spore germination/outgrowth. Such an administration can be a method to induce an immunological response, such as a protective immunological response. The adenovirus in this instance can be a human adenovirus. The adenovirus can be another type of adenovirus, such as a canine adenovirus.

The invention still further provides such methods encompassing applying a delivery device including the vector to the skin of the animal, as well as such a method further including disposing the vector in and/or on the delivery device; and, to such delivery devices.

The invention yet further provides such methods wherein the vector can have all viral genes deleted therefrom, as well as to such vectors.

In addition, the invention provides gene products, e.g., expression products, as well as immunological products (e.g., antibodies), generated by the expression, cells from the methods, as well as in in vitro and ex vivo uses thereof. The expression products and immunological products therefrom can be used in assays, diagnostics, and the like; and, cells that express the immunological products and/or the expression products can be isolated from the host, expanded in vitro and re-introduced into the host.

Even further still, while non-invasive delivery is desirable in all instances of administration, the invention can be used in conjunction with invasive deliveries; and, the invention can generally be used as part of a prime-boost regimen. For instance, the methods of the present invention can be used as part of a prime-boost regimen wherein vaccines are administered prior to or after or concurrently with another administration such as a non-invasive or an invasive administration of the same or a different immunological or therapeutic ingredient, e.g., before, during or after prime vaccination, there is administration by injection or by non-invasive methods described in this invention of a different vaccine or immunological composition for the same or similar pathogen such as a whole or subunit vaccine or immunological composition for the same or similar pathogen whose antigen or epitope of interest is expressed by the vector in the non-invasive administration.

The present invention further comprises the use of the topical application of recombinant vectors as previously described for use in the administration of genes encoding antigens of interest, expression products, or immunological products, all of which can be used to induce a therapeutic effect.

The present invention also encompasses delivery devices (bandages, adhesive dressings, spot-on formulation and its application devices, pour-on formulation and its application devices, roll-on formulation and its application devices, shampoo formulation and its application devices or the like) for the delivery of skin-targeted and other non-invasive vaccines or immunological compositions and uses thereof, as well as compositions for the non-invasive delivery of vectors; and, kits for the preparation of compositions for the non-invasive delivery of vectors. Such a kit comprises the vector and a pharmaceutically acceptable or suitable carrier or diluent and an optional delivery device, each in its own packaging; the packaging may be included in a unitary container or the packaging may each be in separate containers or each may be in its own separate container; the kit can optionally include instructions for admixture of the ingredients and/or administration of the composition.

Pour-on and spot-on formulations are described in U.S. Pat. Nos. 6,010,710 and 5,475,005. A roll-on device is also described in U.S. Pat. No. 5,897,267. The contents of U.S. Pat. Nos. 6,010,710, 5,475,005 and 5,897,267 are hereby incorporated herein by reference, together with documents cited or referenced therein and all documents cited or referenced in such documents. Moreover, a skilled artisan also knows how to make shampoo formulation as well as devices to apply the formulation to an animal.

It is noted that in this disclosure, terms such as "comprises", "comprised", "comprising" and the like can have the meaning attributed to it in U.S. patent law; e.g., they can mean "includes", "included", "including" and the like.

These and other objects, features, and advantages of the invention become further apparent in the following detailed description of the invention when taken in conjunction with the accompanying drawings which illustrate, by way of example, the principles of this invention.

BRIEF DESCRIPTION OF THE DRAWING

The following Detailed Description, given to describe the invention by way of example, but not intended to limit the invention to specific embodiments described, may be understood in conjunction with the accompanying Figures, incorporated herein by reference, in which:

FIGS. 10A and 10B depict the percent cell viability as a function of serum dilution. Sera was obtained from groups immunized as described in the figure legends. Lambda, PA63 and LF7 expressed from a temperature-sensitive lambda promoter; NIVS, noninvasive vaccination onto the skin; IN, intranasal vaccination.

FIGS. 11A and 11B depict the percentage of animals surviving after challenge with *B. anthracis*. The animals received topical application of vaccinations containing *E. coli* vectors expressing PA63 and LF7 or PA63 together with LF7 or neither PA63 or LF7 (as a control) driven by the temperature-sensitive lambda promoter.

Cells were exposed to PBS, *E. coli* control protein or germaxin as indicated. Amount of apoptosis is depicted on the X-axis, and cell death is shown in the Y-axis.

Figure 13:
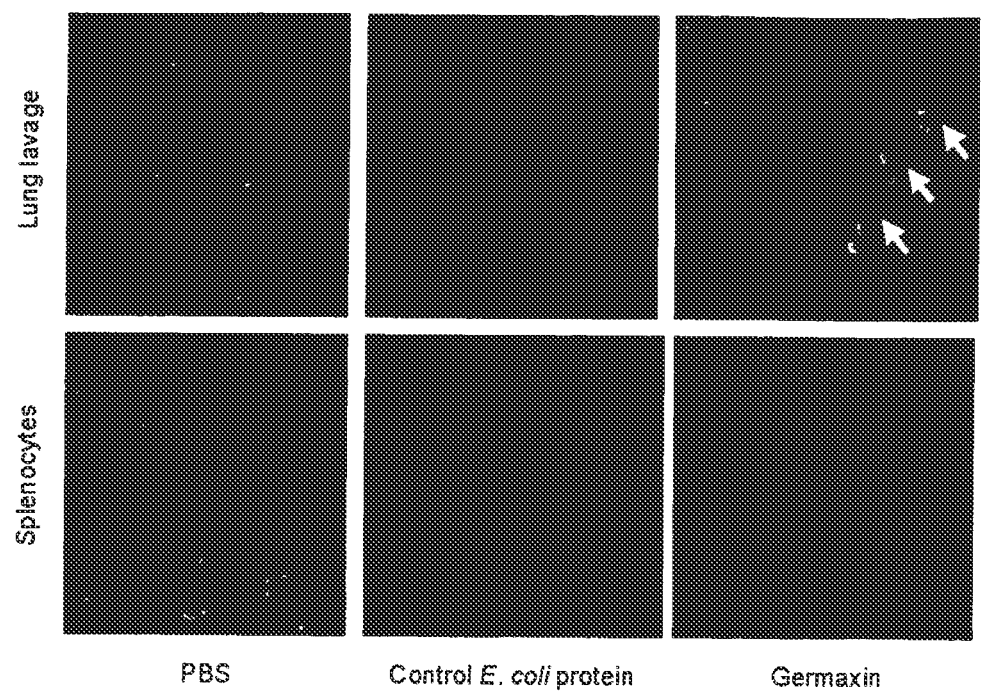

FIG. 13. Specificity of germaxin for induction of apoptosis.

T-cells in splenocytes and macrophges in lung lavage were marked with anti-mouse CD3 and anti-mouse CD11b, respectively. The cells were exposed to PBS, *E. coli* control protein or germaxin as shown prior to immuocytochemical staining. Arrows indicate apoptosis of macrophages in lung lavage. T cells in splenocytes were not affected.

DETAILED DESCRIPTION

Figures 2A, 2B:
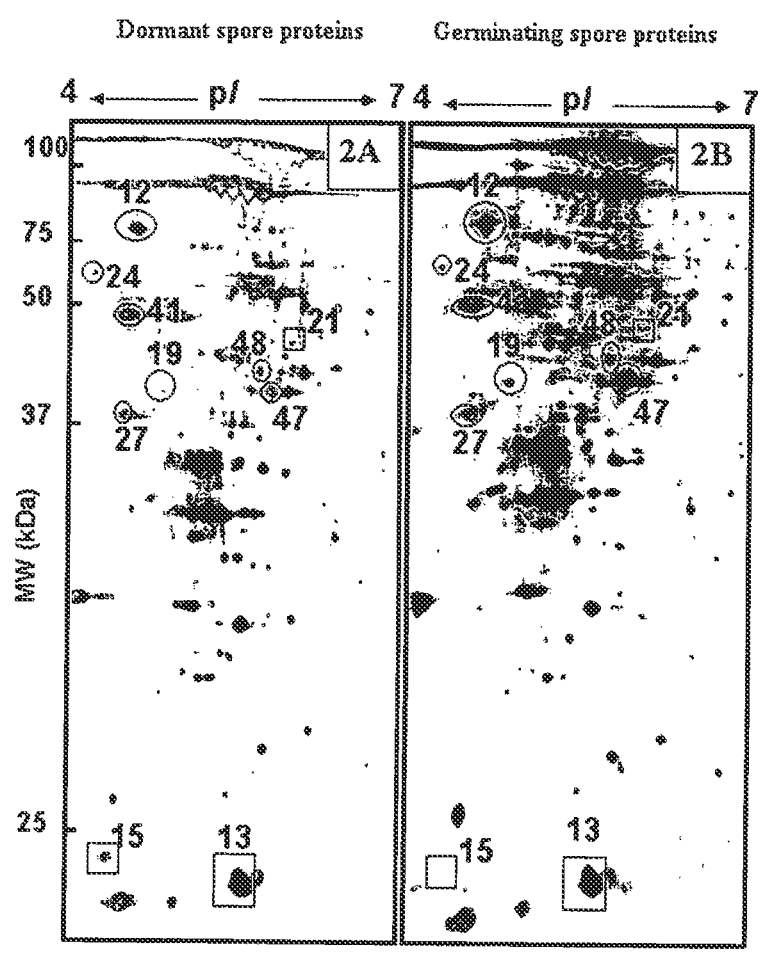
Figure 2C:
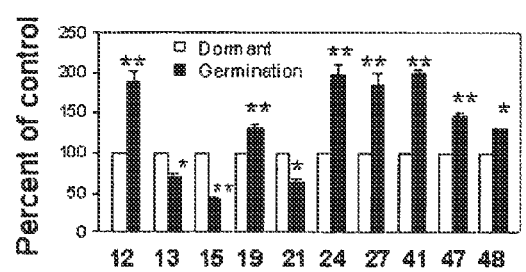
Figure 3A:
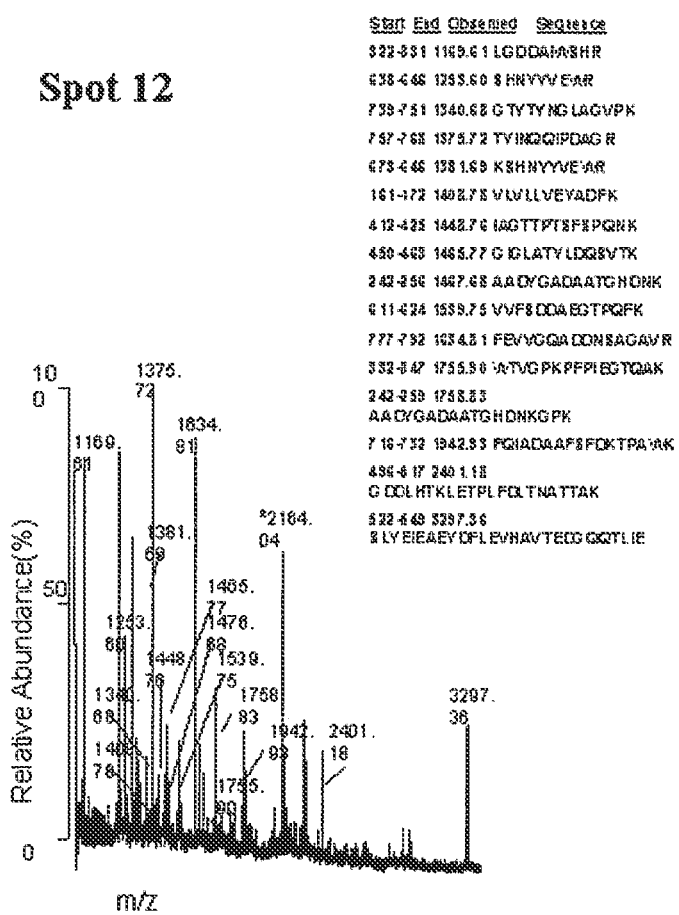
Figure 3B:
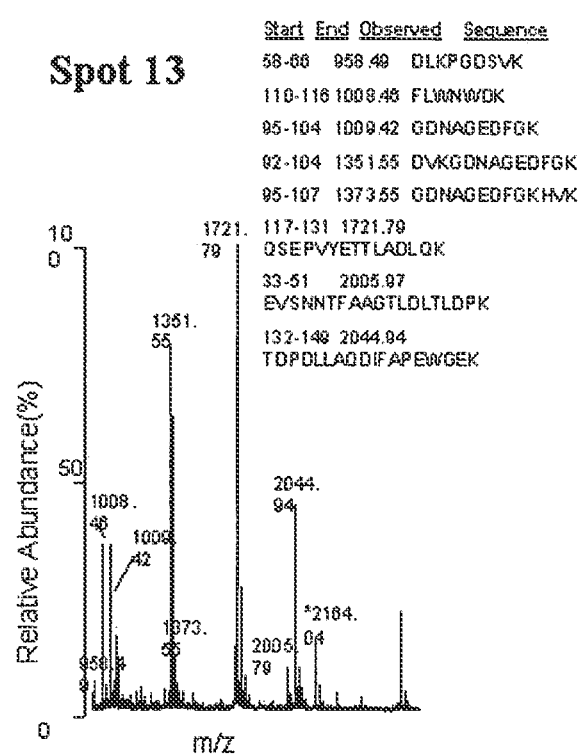
Figure 3C:
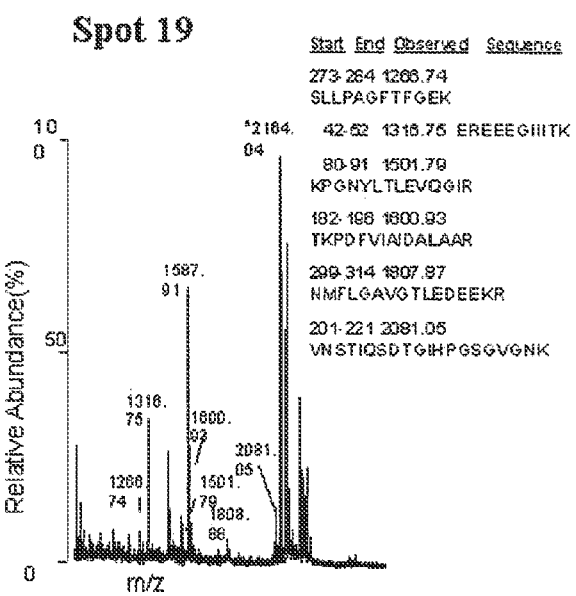
Figure 3D:
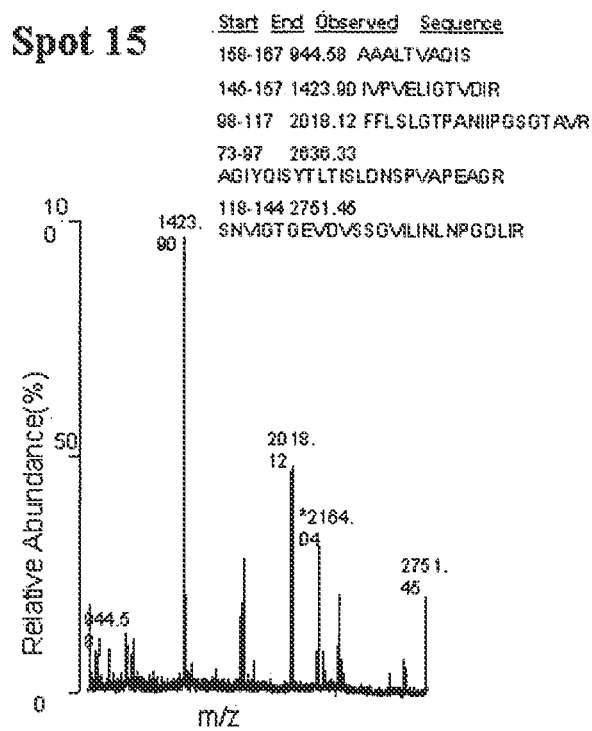

In one embodiment of the present invention, novel germination/outgrowth-associated proteins are identified. These novel proteins include, but are not limited to: a *Bacillus anthracis* germination/outgrowth-associated protein corresponding to Spot 12, wherein the protein has a peptide fingerprint mass spectra as depicted in FIG. 3A, a *Bacillus anthracis* germination/outgrowth-associated protein corresponding to Spot 13, wherein the protein has a peptide fingerprint mass spectra as depicted in FIG. 3B, a *Bacillus anthracis* germination/outgrowth-associated protein corresponding to Spot 19, wherein the protein has a peptide fingerprint mass spectra as depicted in FIG. 3C, a *Bacillus anthracis* germination/outgrowth-associated protein corresponding to Spot 15, wherein the protein has a peptide fingerprint mass spectra as depicted in FIG. 3D, a *Bacillus anthracis* germination/outgrowth-associated protein corresponding to any of spots 21, 24, 27, 41, 47, or 48, each of which is identified in FIG. 2C as having increases or decreases by at least 30%; and a spore protein corresponding to any of spots that has not been reported to be expressed in *Bacillus anthracis* (Table 1 and FIGS. 2A and 2B). A second embodiment of the invention includes methods of identifying and isolating the present novel proteins and additional germination/outgrowth-associated proteins.

In a still further embodiment of the present invention, the novel germination/outgrowth-associated and other spore proteins may be used in decontamination of anthrax spores, and the prevention or treatment of inhalational anthrax, gastrointestinal anthrax, or cutaneous anthrax. Methods and compositions used in the prevention or treatment of disease arising from exposure to *B. anthracis* includes the use of vaccines and/or immunogenic compositions which comprise one or more of the spore proteins described herein, or fragments thereof, and/or one or more vectors which encode one or more of the spore proteins described herein, or fragments thereof, and/or inhibitors of one or more of the germination/outgrowth-as-sociated proteins described herein.

Additionally, the invention includes a method of providing immunization in an animal comprising administering a vector that contains and expresses a nucleic acid molecule encoding the gene product, in an amount effective to induce the response, wherein the immunization and/or systemic immune response and/or systemic therapeutic response affords the animal protection against challenge with *B anthracis*. In an advantageous embodiment, the gene product is one or more of the spore proteins described herein or a fragment thereof.

A further embodiment of the invention includes a method of inducing a systemic immune response or systemic therapeutic response to a gene product, in an animal, comprising administering a vector that contains and expresses a nucleic acid molecule encoding the gene product, in an amount effective to induce the response, wherein the immunization and/or systemic immune response and/or systemic therapeutic response affords the animal protection against challenge with *B. anthracis*. In an advantageous embodiment, the gene product is one or more of the spore proteins described herein or a fragment thereof.

In a still further embodiment, any of the vaccines or immunogenic compositions herein described may optionally include an excipient and/or adjuvant and/or a suitable carrier or diluent. It is understood that one of skill in the art would be able to practice the present invention without any undue experimentation.

Yet further still, the present invention provides methods of making the herein described vaccines and immunogenic compositions. Additionally, a further embodiment of the present invention includes kits providing the components of any of the herein described vaccines or immunogenic compositions, and methods of making such kits.

The present invention advantageously comprises a method of treatment after suspected or true exposure to *B. anthracis* comprising administering an effective amount of one or more inhibitors to one or more of the spore proteins described herein. Such treatment could also include administering the aforementioned vaccines or immunogenic compositions. A further embodiment of the present invention includes the pharmaceuticals, therapeutics, and other compositions employed in the post-exposure treatment, which can include one or more of the spore proteins described herein, or fragments thereof, DNA encoding the proteins or fragments thereof, or inhibitors to the fragments or to any associated factors produced in conjunction with the spore proteins. As one of skill in the art is aware, such treatment or therapies may include the use of excipients, diluents, carriers, or other additional material as is known in the art.

It has been previously demonstrated that vectored vaccines can be inoculated in a novel way as skin-targeted non-invasive vaccines, or immunological or therapeutic compositions. The combination of vectored vaccines with a non-invasive delivery mode results in a new class of "democratic" vaccine, or immunological or therapeutic compositions that require little or no special skill and equipment for administration. Thus, one can administer such compositions to the skin of himself or herself (and, this administration can advantageously be under the direction of a medical practitioner, e.g., to ensure that dosage is proper) or to the skin of an animal (e.g., advantageously a shaved area of skin if the animal is a mammal, although as demonstrated herein, hair removal is not necessary, and more advantageously at a region where the animal will not remove the administration by rubbing, grooming or other activity); and, the present invention thus provides advantages in the administration of vaccine, or immunological, or therapeutic compositions comprising a vector that expresses a gene product, especially with respect to administering such compositions to newborns, young animals, animals generally, children and the like, to whom invasive, e.g., needle, administration can be difficult or inconvenient or painful or harmful.

The present invention is also directed to a method of non-invasive immunization or treatment in an animal, comprising the step of: contacting skin of the animal with a recombinant vector in an amount effective to induce immune response in the animal. Specifically, the present invention is directed towards methods and compositions for the treatment or prevention of infection by *Bacillus anthracis.*

As used herein, a vector is a tool that allows or facilitates the transfer of an entity from one environment to another. By way of example, some vectors used in recombinant DNA techniques allow entities, such as a segment of DNA (such as a heterologous DNA segment, such as a heterologous cDNA segment) and/or heterologous protein, to be transferred into a target cell. In an advantageous embodiment, the vector includes a viral vector, a bacterial vector, a protozoan vector, a DNA vector, or a recombinant thereof.

In a still further embodiment of the present invention, the therapies, treatments, vaccines, and immunogenic compositions herein described may all be used to prevent disease due to exposure to *B. anthracis* in animals. In an advantageous embodiment of the present invention, the animal is a vertebrate. In a still more advantageous embodiment of the present invention, the vertebrate is a mammal. In an even more advantageous embodiment of the present invention, the mammal is a human or a companion or domesticated or food- or feed-producing or livestock or game or racing or sport animal.

Information in U.S. Pat. No. 5,990,091 issued Nov. 23, 1999, WO 99/60164, WO98/00166, "Adenoviral gene delivery elicits distinct pulmonary-associated T helper cell responses to the vector and to its transgene" (van Ginkel 1997), "Vaccination against acute respiratory virus infections and measles in man" (Osterhaus and de Vries 1992), WO 99/53940 and U.S. Pat. Nos. 6,042,838 and 6,004,802, can be relied upon for the practice of this invention (e.g., expressed products, antibodies and uses thereof, vectors for in vivo and in vitro expression of exogenous nucleic acid molecules, exogenous nucleic acid molecules encoding epitopes of interest or antigens or therapeutics and the like, promoters, compositions comprising such vectors or nucleic acid molecules or expressed products or antibodies, dosages, inter alia). It is noted that immunological products and/or antibodies and/or expressed products obtained in accordance with this invention can be expressed in vitro and used in a manner in which such immunological and/or expressed products and/or antibodies are typically used, and that cells that express such immunological and/or expressed products and/or antibodies can be employed in in vitro and ex vivo applications, e.g., such uses and applications can include diagnostics, assays, ex vivo therapy (e.g., wherein cells that express the gene product and/or immunological response are expanded in vitro and reintroduced into the host or animal), etc., see U.S. Pat. No. 5,990,091, WO 99/60164, WO 98/00166, WO 99/53940, and U.S. Pat. Nos. 6,042,838, and 6,004,802, and documents cited therein and documents cited or referenced in such documents. Further, expressed antibodies or gene products that are isolated from herein methods, or that are isolated from cells expanded in vitro following herein administration methods, can be administered in compositions, akin to the administration of subunit epitopes or antigens or therapeutics or antibodies to induce immunity, stimulate a therapeutic response and/or stimulate passive immunity. The quantity to be administered will vary for the patient (host) and condition being treated and will vary from one or a few to a few hundred or thousand micrograms, e.g., 1 .mu.g to 1 mg, from about 100 ng/kg of body weight to 100 mg/kg of body weight per day and preferably will be from 10 pg/kg to 10 mg/kg per day. A vector can be non-invasively administered to a patient or host in an amount to achieve the amounts stated for gene product (e.g., epitope, antigen, therapeutic, and/or antibody) compositions. Of course, the invention envisages dosages below and above those exemplified herein, and for any composition to be administered to an animal or human, including the components thereof, and for any particular method of administration, it is preferred to determine therefor: toxicity, such as by determining the 50% lethal dose (LD.sub.50) in a suitable animal model e.g., rodent such as mouse; and, the dosage of the composition(s), concentration of components therein and timing of administering the composition(s), which elicit a suitable response, such as by titrations of sera and analysis thereof, e.g., by ELISA and/or seroneutralization analysis. Such determinations do not require undue experimentation from the knowledge of the skilled artisan, this disclosure and the documents cited herein. And, the invention also comprehends sequential administration of inventive compositions or sequential performance of herein methods, e.g., periodic administration of inventive compositions such as in the course of therapy or treatment for a condition and/or booster administration of immunological compositions and/or in prime-boost regimens; and, the time and manner for sequential administrations can be ascertained without undue experimentation. Further, the invention comprehends compositions and methods for making and using vectors, including non-replicative vectors, including methods for producing gene products and/or immunological products and/or antibodies in vivo and/or in vitro and/or ex vivo (e.g., the latter two being, for instance, after isolation of cells from a host that has had a non-invasive administration according to the invention, e.g., after optional expansion of such cells), and uses for such genes and/or immunological products and/or antibodies, including in diagnostics, assays, therapies, treatments, and the like. Vector compositions are formulated by admixing the vector with a suitable carrier or diluent; and, gene product and/or immunological product and/or antibody compositions are likewise formulated by admixing the gene and/or immunological product and/or antibody with a suitable carrier or diluent; see, e.g., U.S. Pat. No. 5,990,091, WO 99/60164, WO 98/00166, WO 99/53940, and U.S. Pat. Nos. 6,042,838 and 6,004,802, documents cited therein, and other documents cited herein, and other teachings herein (for instance, with respect to carriers, diluents and the like).

If nasal or respiratory (mucosal) administration is desired, compositions may be in a form and dispensed by a squeeze spray dispenser, pump dispenser or aerosol dispenser. Such dispensers may also be employed to deliver the composition to oral or oral cavity (e.g., buccal or perlingual) mucosa. Aerosols are usually under pressure by means of a hydrocarbon. Pump dispensers can preferably dispense a metered dose or, a dose having a particular particle size.

Compositions of the invention can contain pharmaceutically acceptable flavors and/or colors for rendering them more appealing, especially if they are administered orally (or buccally or perlingually); and, such compositions can be in the form of tablets or capsules that dissolve in the mouth or which are bitten to release a liquid for absorption buccally or perlingually (akin to oral, perlingual or buccal medicaments for angina such as nitroglycerin or nifedimen). The viscous compositions may be in the form of gels, lotions, ointments, creams and the like (e.g., for topical and/or mucosal and/or nasal and/or oral and/or oral cavity and/or perlingual and/or buccal administration), and will typically contain a sufficient amount of a thickening agent so that the viscosity is from about 2500 to 6500 cps, although more viscous compositions, even up to 10,000 cps may be employed. Viscous compositions have a viscosity preferably of 2500 to 5000 cps, since above that range they become more difficult to administer. However, above that range, the compositions can approach solid or gelatin forms which are then easily administered as a swallowed pill for oral ingestion and/or a pill or capsule or tablet for holding in the mouth, e.g., for buccal or perlingual administration.

Liquid preparations are normally easier to prepare than gels, other viscous compositions, and solid compositions. Additionally, liquid compositions are somewhat more convenient to administer, especially by injection or orally or buccally or perlinually, to animals, children, particularly small children, and others who may have difficulty swallowing a pill, tablet, capsule or the like, or in multi-dose situations. Viscous compositions, on the other hand, can be formulated within the appropriate viscosity range to provide longer contact periods with mucosa, such as the lining of the stomach or nasal mucosa or for perlingual or buccal or oral cavity absorption.

Obviously, the choice of suitable carriers and other additives will depend on the exact route of administration and the nature of the particular dosage form, e.g., liquid dosage form (e.g., whether the composition is to be formulated into a solution, a suspension, gel or another liquid form), or solid dosage form (e.g., whether the composition is to be formulated into a pill, tablet, capsule, caplet, time release form or liquid-filled form).

Solutions, suspensions and gels, normally contain a major amount of water (preferably purified water) in addition to the antigen, lipoprotein and optional adjuvant. Minor amounts of other ingredients such as pH adjusters (e.g., a base such as NaOH), emulsifiers or dispersing agents, buffering agents, preservatives, wetting agents, jelling agents, (e.g., methylcellulose), colors and/or flavors may also be present. The compositions can be isotonic, i.e., it can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions must be selected to be chemically inert with respect to the vector or antigen or epitope of interest and optional adjuvant or other active or immunity-enhancing ingredients. This will present no problem to those skilled in chemical and pharmaceutical principles, or problems can be readily avoided by reference to standard texts or by simple experiments (not involving undue experimentation), from this disclosure and the documents cited herein.

The immunologically effective compositions of this invention are prepared by mixing the ingredients following generally accepted procedures. For example the selected components can be simply mixed in a blender, or other standard device to produce a concentrated mixture which can then be adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient or animal, and the composition form used for administration (e.g., solid vs. liquid). Dosages for humans or other mammals can be determined without undue experimentation by the skilled artisan, from this disclosure, the documents cited herein, the Examples below and from the applications, patents and other documents cited herein and documents cited or referenced in documents cited herein, all of which are incorporated herein by reference.

Suitable regimes for initial administration and booster doses or for sequential administrations also are variable, and may include an initial administration followed by subsequent administrations; but nonetheless, may be ascertained by the skilled artisan, from this disclosure, the documents cited and incorporated by reference herein, including applications and patents cited herein and documents referenced or cited herein, all of which are hereby incorporated herein by reference, as well as the Examples below. The compositions can be administered alone, or can be co-administered or sequentially administered with other compositions of the invention or with other prophylactic or therapeutic compositions.

EXAMPLES

The present invention will now be described by way of the following examples, which are illustrative only and non-limiting.

Bacterial Strains and Spore Preparations.

The Sterne strain of *Bacillus anthracis* harboring the plasmid (pXO1.sup.+) encoding the anthrax toxins but lacking the plasmid (pXO2.sup.−) encoding the capsule were used in this study (provided by Colorado Serum). Spores were prepared from broth cultures of *Bacillus anthracis* Sterne and purified by centrifugation on density gradients of Renografin-60 (Bracco Diagnostic, Princeton N.J.) as described previously (Steichen 2003). Dormant spores of *Bacillus anthracis* Sterne were heated at 65.degree. C. for 30 min prior to growth or purification. The germination period after inoculation of dormant spores into medium was determined by decline in optical density at 560 m (OD.sub.560), loss of refractility of spores by phase-contrast microscopy, increase in stainability of spores with Gram's crystal violet, and loss of heat resistance as described (Welkos 2001).

Example 1: Characterization of Germination of *Bacillus anthracis* Spores

Figure 1A:
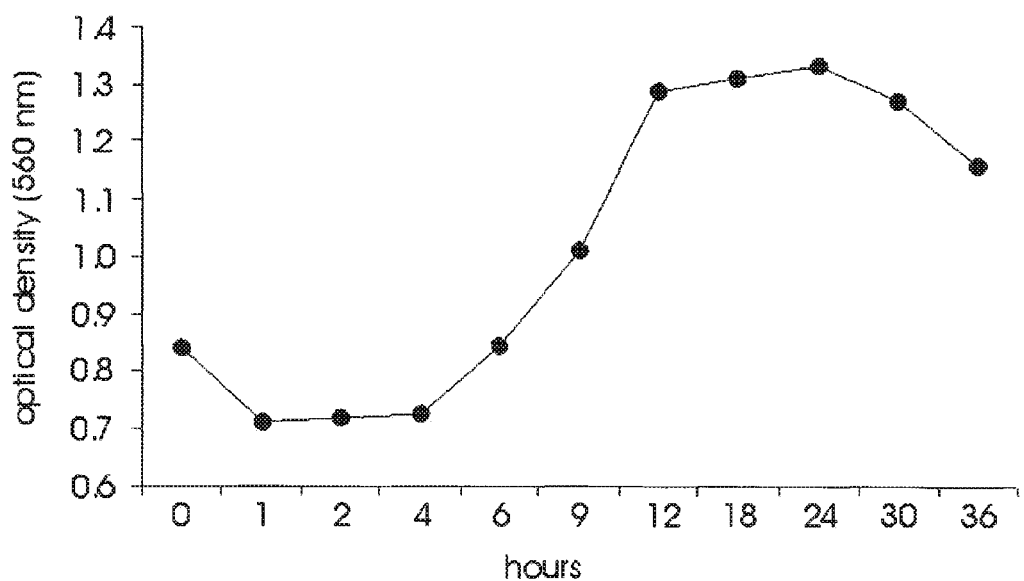
FIGS. 1A-B. *B. anthracis* growth (1A) Growth curve of *B. anthracis*. (1B) Spore germination and outgrowth at the onset of the *B. anthracis*' growth curve. Growth was measured by periodically reading the optical density of cul harboring pnirB-LF7 and -PA63; .lambda.32, *E. coli* cells harboring p.lambda.tsP.sub.R-LF7 and -PA63 with the P.sub.R promoter repressed by c1857 at 32.degree. C.; .lambda.42, *E. coli* cells harboring pktsP.sub.R-LF7 and -PA63 with the P.sub.R promoter induced for 2 hours at 42.degree. C. prior to administration. There were 15 mice per group for nirB; and 10 mice per group for others. Open bar, sera harvested a month postimmunization before the boost; solid bar, sera harvested two months postimmunization (i.e., a month postboost). Shown are geometric means.
Figure 1B:
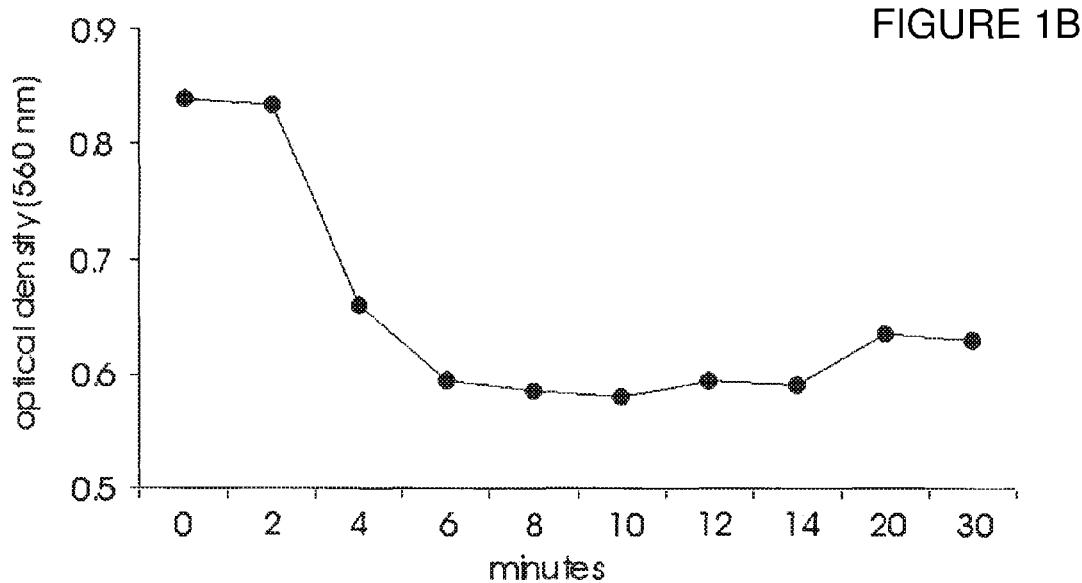

Dormant spores of *Bacillus anthracis* Sterne strain were heated at 65.degree. C. for 30 min prior to growth in medium for 2 days at 37.degree. C. with shaking. Aliquots of samples were removed periodically for spectrophotometric analysis (OD.sub.560) and the results were plotted as a growth curve characterizing the spore germination stage (FIGS. 1A and 1B). The decline in OD.sub.560 for the first 15 min (FIG. 2*b*) is recognized as germinating stage (Welkos, S. et al., Microbiology 147:1677-1685, 2001).

Microscopic validation of spore germination was also performed. Purified dormant spores and spores with germination and early outgrowth induced at 37.degree. C. in medium for 10 min, respectively, were fixed in 10% buffered formalin, dried, and viewed on a Zeiss Axioskop2 plus microscope using a 100.times.oil immersion lens.

Example 2: Proteomic Profiling of *Bacillus anthracis* Spores

Proteomic profiling of *Bacillus anthracis* dormant and germinating spores was used to reveal a number of spore proteins.

*Bacillus anthracis* spores were prepared as previously described (Steichen, C. et al., J Bacteriol 185:1903-1910, 2003). Total protein was extracted from dormant and germinating spores as described (Huang 2003). Aliquots containing 300 .mu.g protein were mixed 1:1 with rehydration solution containing 7 M urea, 2 M thiourea, 4% CHAPS, 2% SB 3-10, 5 mM tri-butylphosphine, 1.6% pH 5-8 Bio-lytes, 0.4% pH 3-10 Bio-Lytes, and trace bromophenol blue. Samples were subjected to isoelectricfocusing (IEF) in 13-cm linear gradient Immobiline Dry-Strips, pH 4-7, at 60 kVh using a Pharmacia Hoefer Multiphor II electrophoresis chamber.

Following IEF, Dry-Strips were incubated at room temperature for 20 min in equilibration solution containing 50 mM Tris-HCl, pH 8.8, 6 M urea, 2% sodium dodecyl sulfate (SDS), 30% glycerol, and 5 mM tri-butylphosphine. Dry-Strips were then embedded in 1% agarose containing trace bromophenol blue and loaded onto a large format (12.5 cm.times.20 cm), 8-16% gradient SDS-polyacrylamide gel. Electrophoresis was conducted at 200V for 5 to 6 h or 30 mA per gel overnight until the bromophenol blue dye front was within 2 cm of the bottom of the gel.

Polyacrylamide gels were then stained with Coomassie blue or silver nitrate as described (Huang 2003). Silver-stained gels were scanned using a Molecular Dynamics Personal Densitometer, and protein spots were quantified using PDQuest software (Bio-Rad, Hercules, Calif.). All differences in gel-spot density between groups were verified manually to rule out the possibility of artifacts. To address variability in silver-staining, individual gel spot volumes were normalized by dividing their optical density values by the total optical density values of all the spots present in the gel. FIGS. 2A and 2B depict a proteomic profile obtained by analyzing protein from dormant spores. Fifty protein spots were subsequently excised and analyzed by in-gel trypsin digestion followed by MALDI-TOF MS.

In-gel digestion was performed essentially as described (Huang 2003). Protein spots excised from the Coomassie blue- or silver-stained gel were destained in 0.2 ml acetonitrile for 15 min and dried to completion in a SpeedVac vacuum centrifuge. Samples were then rehydrated on ice for 45 min in digestion buffer (50 mM acetonitrile, 0.04 mg/ml modified trypsin; Promega, Madison, Wis., USA). After removing excess solution, proteins were further digested at 37.degree. C. for 15 h. The resultant peptides were extracted with 5% formic acid in 50% acetonitrile and desalted and concentrated using ZipTips containing C 18 resin (Millipore, Bedford, Mass., USA).

Peptides were eluted from the ZipTips with 75% acetonitrile/0.1% trifluoroacetic acid, applied to the sample target, and air-dried. Peptide fragments were then reconstituted in matrix solution containing .alpha.-cyano-4-hydroxycinnamic acid dissolved in 50% acetonitrile/0.1% trifluoroacetic acid and analyzed with a PerSeptive Voyager-DE MALDI-TOF mass spectrometer (PerSeptive Biosystems, Framingham, Mass., USA). Peptides were evaporated with a N.sub.2 laser at 337 nm. Each spectrum was the cumulative average of 50-100 laser shots. All peptide samples were measured as mono-isotopic masses, and autolytic peaks of trypsin were used for internal calibration. Up to one missed trypsin cleavage was allowed, although most matches did not contain any missed cleavages. This procedure resulted in mass accuracies of 100 ppm. Peptide fingerprint mass spectra exceeding 5% of full scale were analyzed, interpreted, and matched to SWISS-PROT database entries using Mascot, a searching algorithm available at the webpage administered by Matrix Science, Ltd. Matches were computed using a probability-based Mowse score defined as −10*log (P), where P is the probability that the observed match was a random event (Perkins 1999). Mowse scores greater than 70 were considered significant (p<0.05).

Peptide mass fingerprint spectra were analyzed, interpreted, and matched to SWISS-PROT database entries using the Mascot database searching algorithm (Table 1). Over 500 proteins from the dormant Sterne spore strain were reproducibly displayed across an IEF range of 4 to 7. A total of 50 protein spots (FIGS. 2A and 2B and Table I), corresponding to 36 different anthrax spore proteins, were successfully identified by MALDI-TOF MS (PerSeptive Biosystems, Framingham, Mass.). Four proteins (spot 11-14) were further sequenced by Q-TOF 2 MS/MS (Micromass, Manchester, UK).

Tandem mass spectral analyses were performed with a Q-TOF 2 mass spectrometer (Micromass, Manchester, UK) using electrospray ionization. Samples had undergone a 16 h tryptic digest at 37.degree. C. The resulting peptides were purified using ZipTips to concentrate and desalt the samples. The samples were then analyzed by LCMSMS. Liquid chromatography was performed using a LC Packings Ultimate LC, Switchos microcolumn switching unit and Famos autosampler (LC Packings, San Francisco, Calif.) The samples were concentrated on a 300 .mu.m i.d. C18 precolumn at a flow rate of 10 .mu.1/min with 0.1% formic acid and then flushed onto a 75 .mu.m i.d. C18 column at 200 .mu.1/min with a gradient of 5-100% actonitrile (0.1% formic acid) in 30 min. The nano-lc interface was used to transfer the lc eluent into the mass spectrometer. The Q-TOF was operated in the automatic switching mode whereby multiply-charged ions were subjected to MSMS if their intensities rose above 6 counts.

Proteins of diverse function were characterized, including those involved as structural proteins, proteases, amino acid/protein metabolism, molecular chaperones, energy metabolism, transcription/translation, transporters, and membrane proteins.

Example 3: Determination of Germination/Outgrowth-Associated Proteins

Germination/outgrowth-associated proteins were revealed by subtracting background proteins in dormant spores. The protein samples from dormant spores (time 0, FIG. 2A) and germinating stage (10 min, FIG. 2B) were subjected to IEF within linear pH gradients ranging from 4-7 followed by 2-DE and silver-staining. Using MALDI-TOF MS in conjunction with a probability-based database searching algorithm, 10 proteins were recognized to display increase or decreases during the germinating stage. The protein spots were quantified using PDQuest software (Bio-Rad, Hercules, Calif.). All germination/outgrowth-stage protein spots showing a statistically significant increase or decrease (defined as greater than 30% change in comparison to those in dormant spores) were selected for further analysis.

To further identify protein spots, spots were cut from the silver-stained gels and in-gel digested with the trypsin enzyme. The digested peptides were mixed with matrix solution containing .alpha.-cyano-hydroxycinnamic acid and then analyzed on a PerSeptive Voyager-DE MALDI-TOF mass spectrometer (PerSeptive Biosystems). Peptide fingerprint mass spectra generated from MALDI-TOF were interpreted and matched to SWISS-PROT database entries using Mascot, a searching algorithm available at the website administered by Matrix Science, Ltd.

Overall, a partial proteome map of *B. anthracis* spores was constructed with the results generated by 2-DE. Using PDQuest software, 587 paired protein spots, isolated from dormant and germinating spores, respectively, were reproducibly displayed under the specified conditions (FIGS. 2A and 2B). Fifty protein spots, comprising 36 individual proteins, were identified by MALDI-TOF MS (Table 1), with protein sequence coverage averaging 26%. A subset of spots (11-14) was further characterized by Q-TOF 2 MS/MS (Table 1). Comparative sequence alignment of the 36 identified proteins using the BLAST algorithm (Gish and States 1993) showed that 26 of them share the highest sequence identity with putative homologues of *B. cereus*, 5 are most similar to proteins of other *Bacillus* species, whereas 5 have no significant homology to database entries. The identified proteins are functionally diverse and 86% (31/36) of them have not been included in the *B. anthracis* proteomic database prior to this report (Table 1). Ninety-four % (29/31) of these newly-discovered *B. anthracis* proteins (Spots 12-14, 17-20, 22-23, 25, 29-50) were predicted through whole-genome sequencing efforts (Read 2002; Ariel 2003; Ivanova 2003; Read 2003); however, it was not known that they are expressed as spore proteins in such abundance.

Twenty-six *B. anthracis* spore proteins, whose levels are not significantly different between dormant and germinating spores, were identified as reference markers in this study. Among these, surface layer homology (SLH) domain protein is a structural, cell surface-associated protein (Couture-Tosi. E. 2002) identified by MALDI-TOF MS analysis of protein spots 1-11. Three internal sequences (amino acids, 194-205: AEAAQFLALTDK (SEQ ID NO: 36), 194-206: AEAAQFIALTDKK (SEQ ID NO: 37), and 238-249: LSADDVTLEGDK (SEQ ID NO: 38) within spot 11 were sequenced by Q-TOF 2 MS/MS to confirm the existence of this protein (Table I). Clp protease is a stress-responsive protease (Lemos and Burne 2002) identified from spot 20. The relevance of chaperones to the germination process is suggested from the number and types identified in this study although some of them may have been trapped into spores during their expression in mother cells. Of these, we identified Heat shock protein (Hsp)-70 (spot 25), Hsp-60 (spot 26), and chaperonin (spot 28). In addition to chaperones, proteins with a role in transcription and translation were also identified. These include elongation factors G and Ts and RNA polymerase, spots 29, 30, and 31, respectively. Metabolic proteins account for 21 of the 50 identified spots. The enzyme Cysteine synthase A (EC 4.2.99.8) was identified from protein spots 22 and 23. Acetate kinase (EC 2.7.2.1) was identified from spot 32. Delta-1-pyrroline-5-carboxylate dehydrogenase (EC 1.2.1.3) was identified from spots 33 and 34. Multiple subunits of the Pyruvate dehydrogenase multienzyme complex (PDH) were also identified. The PDH E1.alpha. and .beta. subunits, the PDH E2 subunit, and the PDH E3 subunit, were identified from spots 35, 42, 36, and 38, respectively. A role for the E1.beta., E2 and E3 subunits of PDH in the regulation of sporulation has been previously elucidated in *B. subtilis* (Walter and Aronson 1999; Gao 2002). Alkyl hydroperoxide reductase (EC 1.6.99.3) was identified from spot 37. Present in both spores and growing cells, Alkyl hydroperoxide reductase is an oxidative stress-responsive protein and component of the peroxide-responsive perR operon (Casillas-Martinez 2000). Oxidoreductase (EC 1.1.1.-), identified from spot 39, is a member of the large aldo/keto reductase family. Enolase (EC 4.2.1.11) was identified from spot 40. The F.sub.0 portion of ATP synthase (EC 3.6.3.14) was identified from spot 45. Spot 43 was characterized as Fructose bisphosphate aldolase (EC 4.1.2.13). In *B. subtilis*, induction of this enzyme occurs following exposure to anaerobic conditions (Marino 2000). Spot 44 was identified as Triosephosphate isomerase (EC 5.3.1.1). Spot 50 was identified as Alcohol dehydrogenase (EC 1.1.1.1). Band 7, SPFH domain protein of the Band 7 family, was identified from spot 49. Spore proteins in this category also include Hypothetical proteins 2 (Spot 14), 4 (Spot 17) and 5 (Spot 18) with no significant homology to database entries and no known functions.

Seven proteins exhibited germination and early outgrowth-associated increases. Of these, the level of Immune inhibitor A (spot 12) was increased nearly 2-fold. The GPR-like spore protease (spot 19) was increased to a lesser degree. The level of the chaperones Trigger factor in spot 24 and TCP-1/cpn60 in spot 27 was also elevated nearly 2-fold. Trigger factor plays a role in the process of protein maturation and the export of secretory proteins (Deuerling 1999). Levels of the F.sub.1 portion of ATP synthase (spot 41), Glyceraldehyde-3-phosphate dehydrogenase (spots 46 and 47), and Sugar ABC transporter (spot 48) were all increased, suggesting that there may be increased metabolic activity involving these proteins during spore germination and early outgrowth.

Proteins with germination and early outgrowth-associated decreases include Hypothetical protein 1 which has recently been named germaxin (spot 13), Hypothetical protein 3 (spot 15 and 16), and Alanine racemase (spot 21). The Hypothetical protein 3 was recently identified as a potential *B. anthracis* spore coat protein (Lai 2003) with unknown functions.

Spot 12

Figure 4A:
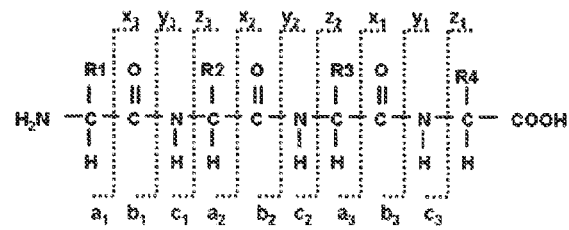
Figure 4B:
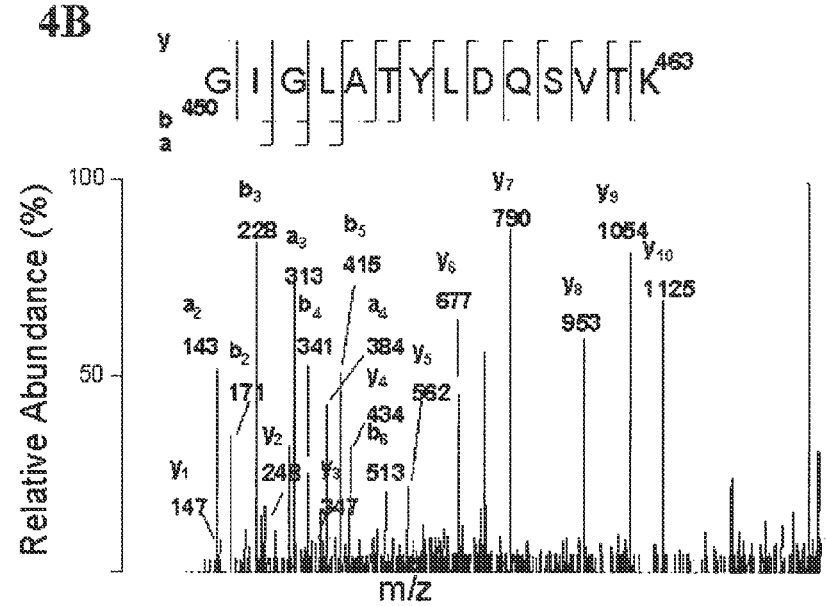

Sixteen peaks within the peptide mass fingerprint of spot 12 matched those of protein with accession # gi.vertline.21399197 in the SWISS-PROT database (FIG. 3A). The protein originally named as hypothetical protein predicted by GeneMark is a predicted protein from genomes of *Bacillus anthracis* (Read 2002). By using a Q-TOF 2 mass spectrometer, the internal sequence of this predicated protein was determined for the amino acids between positions 450 and 463 with m/z value at 1465.77 (FIG. 4B). All 14 amino acid residuals (GIGLATYLDQSVTK; SEQ ID NO: 8) from spot 12 were easily determined. More interestingly, the entire amino acid sequence of spot 12 of *Bacillus anthracis* was found to share more than 95% of its identity with immune inhibitor A (gi.vertline.9858110) of *Bacillus thuringiensis*. Both of these proteins contain the HEXXH motif which is defined as a zinc-binding domain of metalloprotease (Lovgren 1990), suggesting that spot 12 may be a zinc-dependent metalloprotease, specifically immune inhibitor A.

Figure 4C:
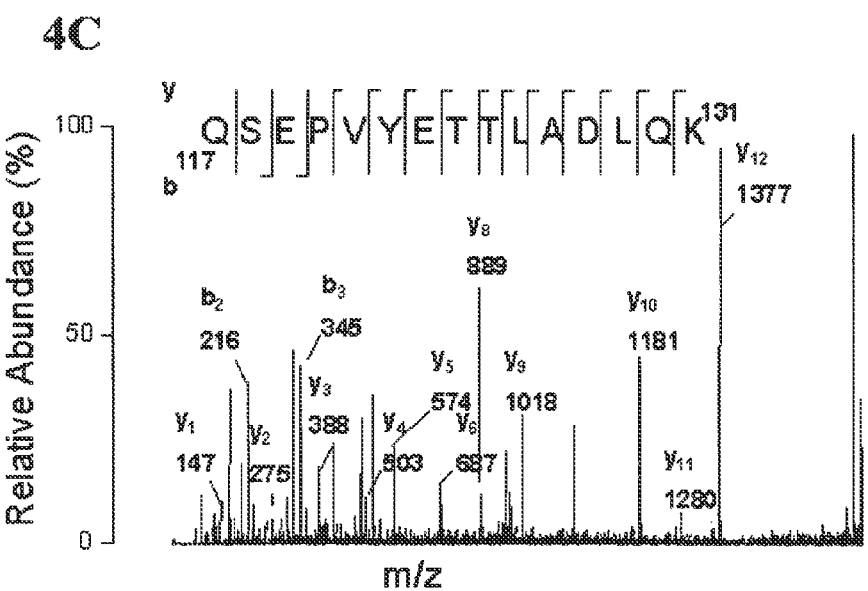
Figure 5A:
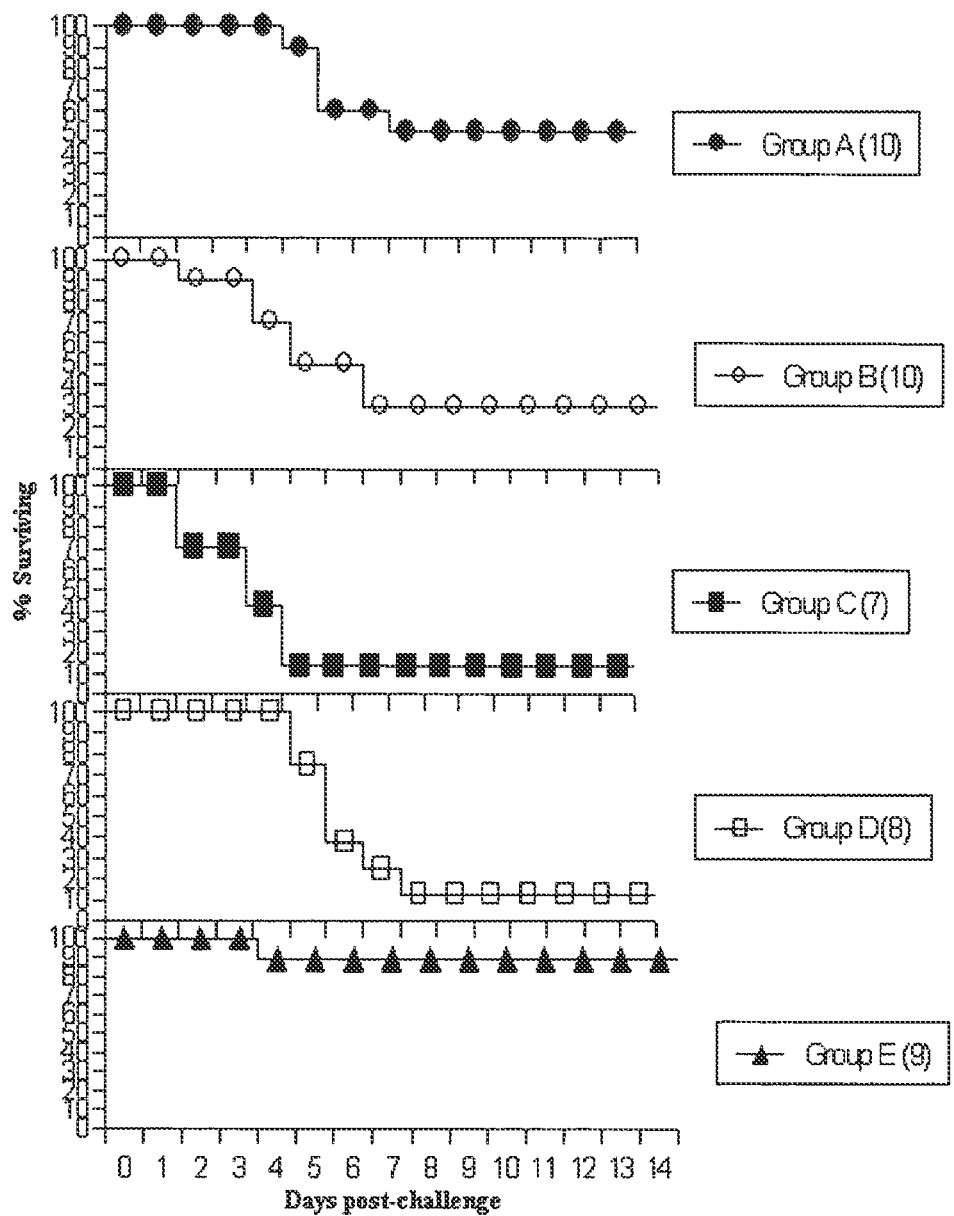
Figure 5B:
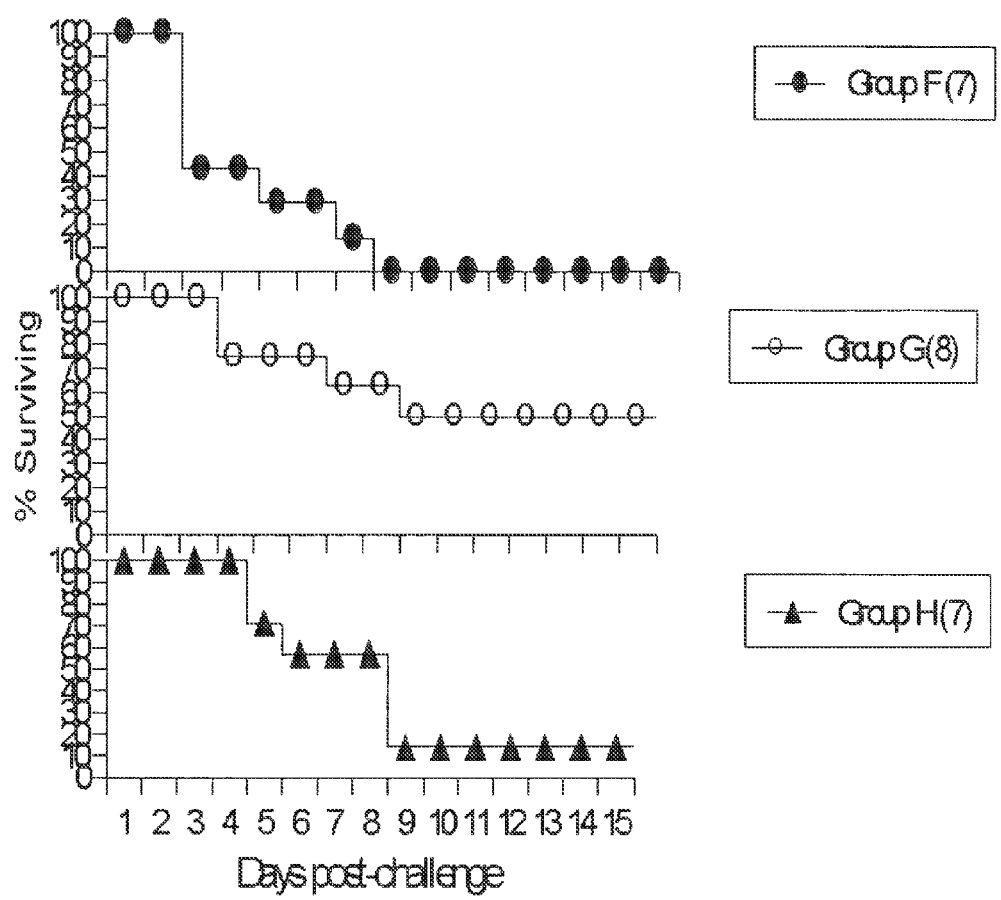
Figure 5C:
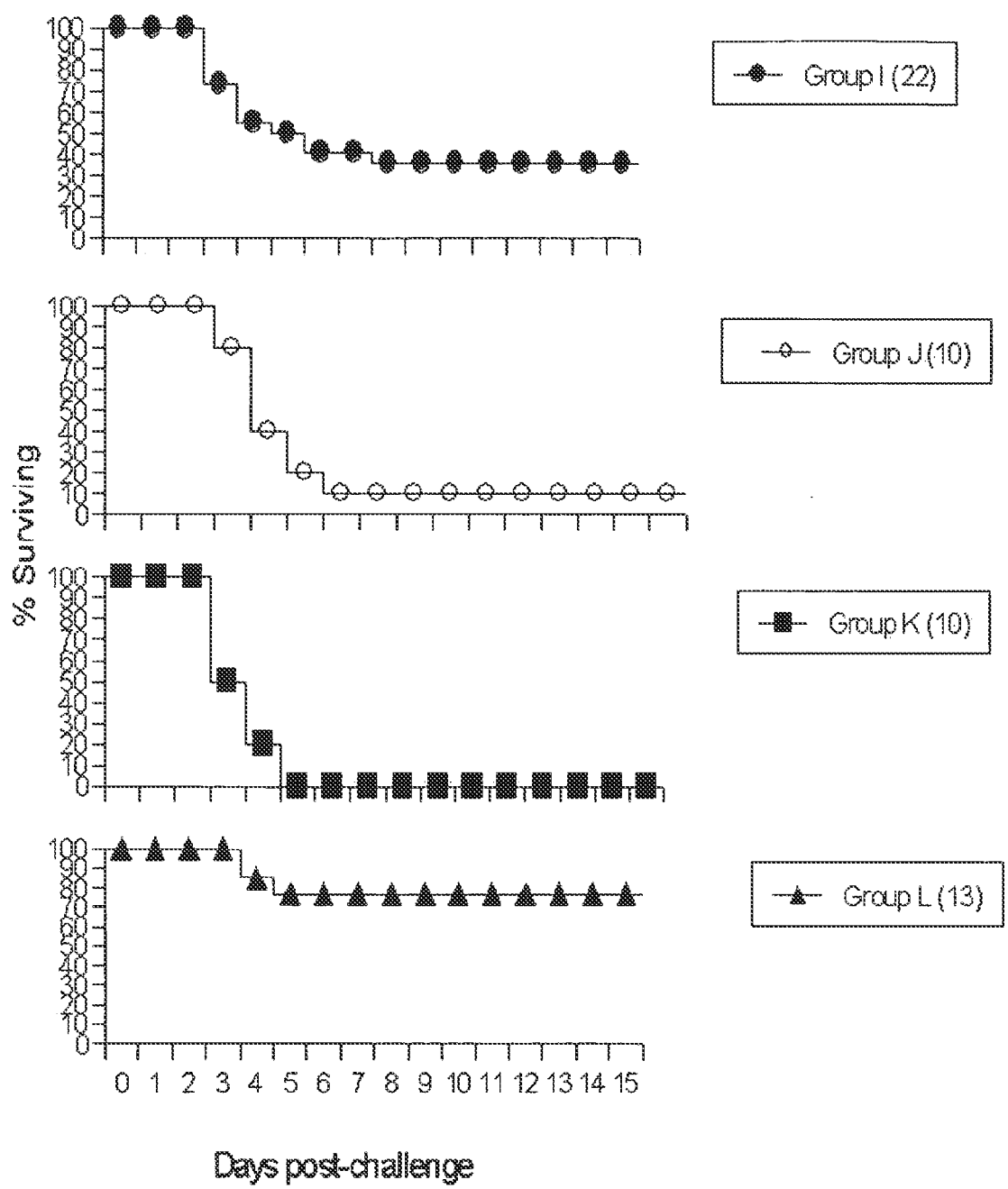
Figure 5D:
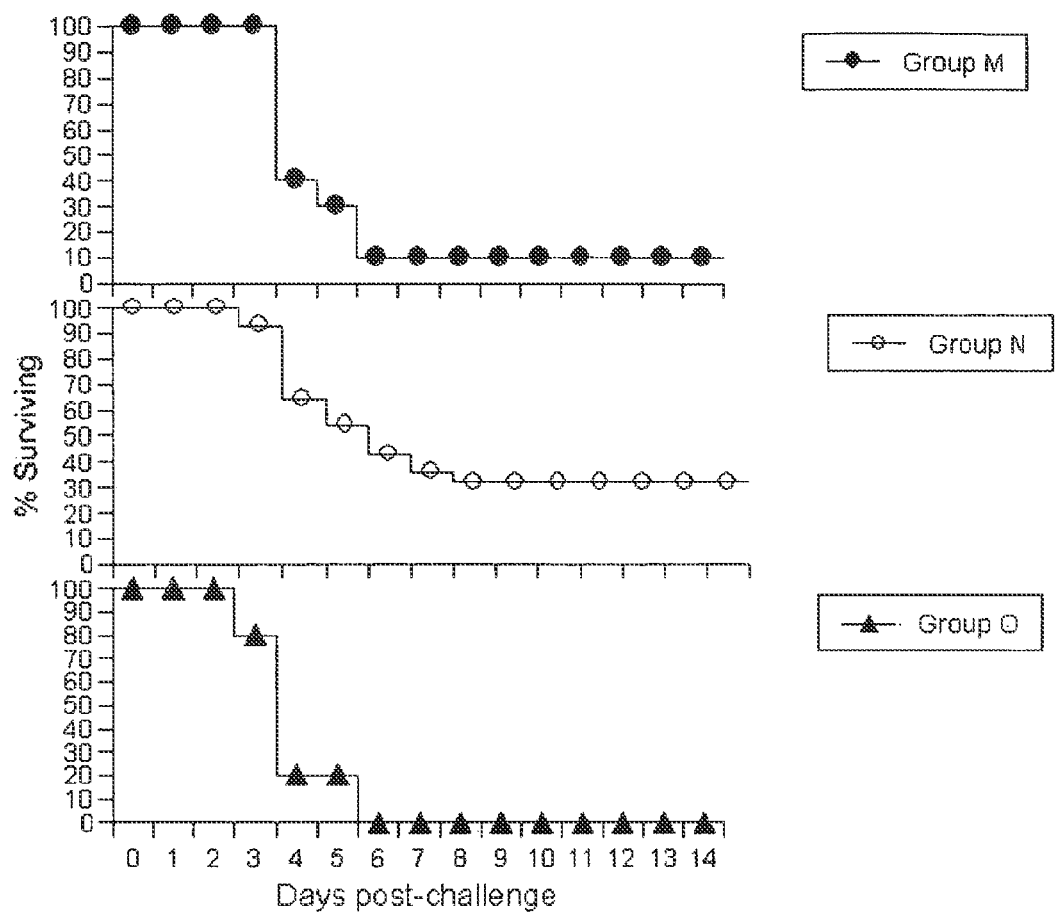
Figure 5E:
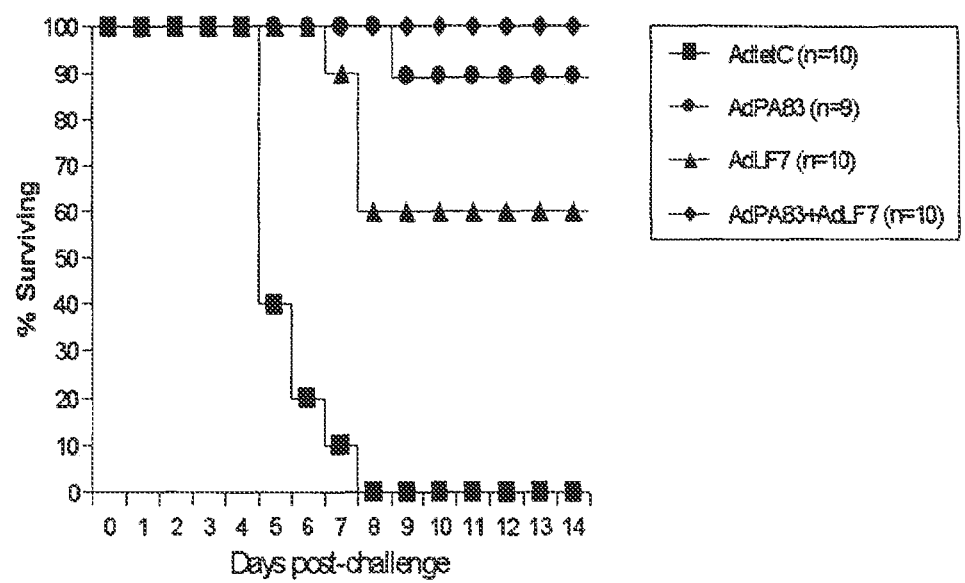
Figure 6A:
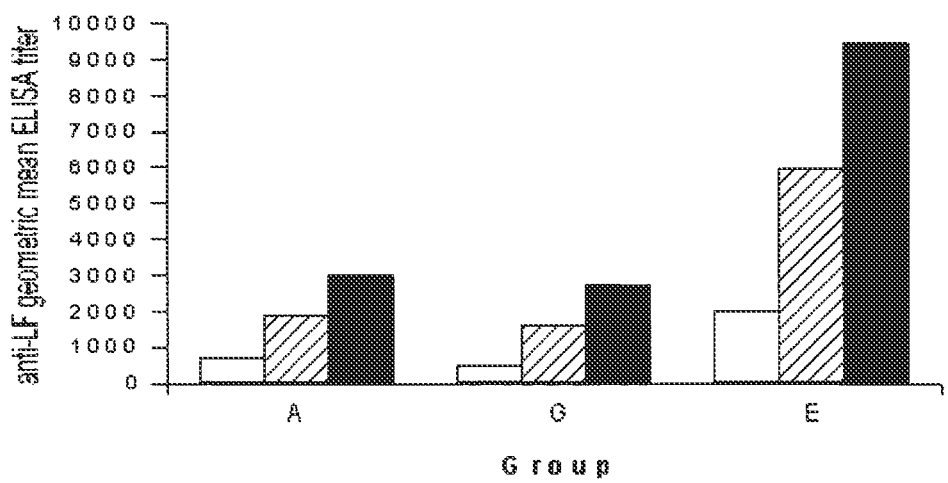
Figure 6B:
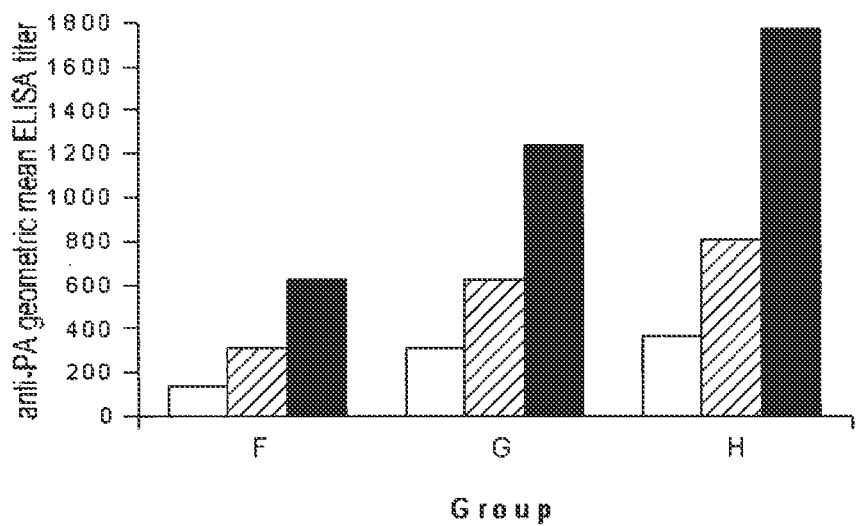
Figure 6C:
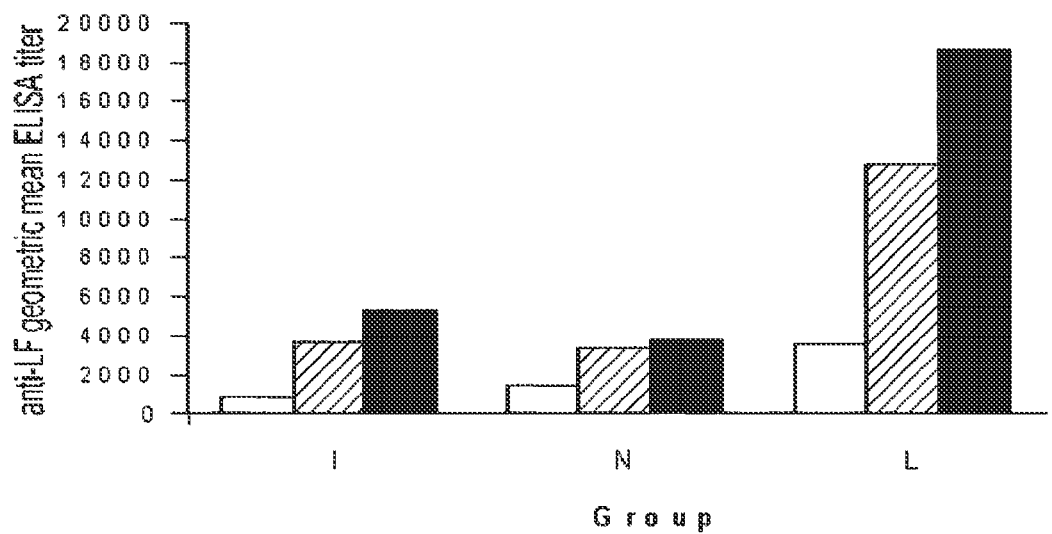
Figure 6D:
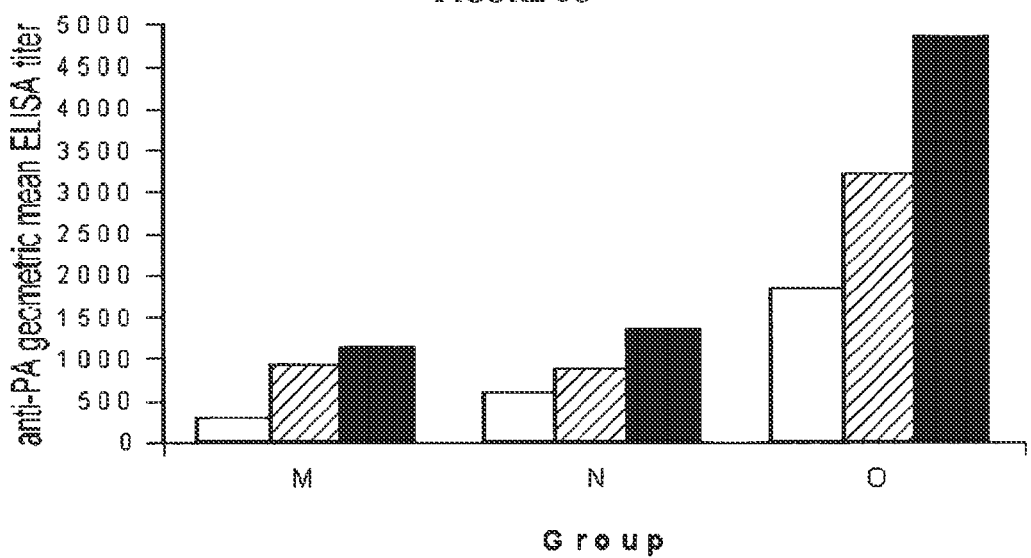
Figure 7A:
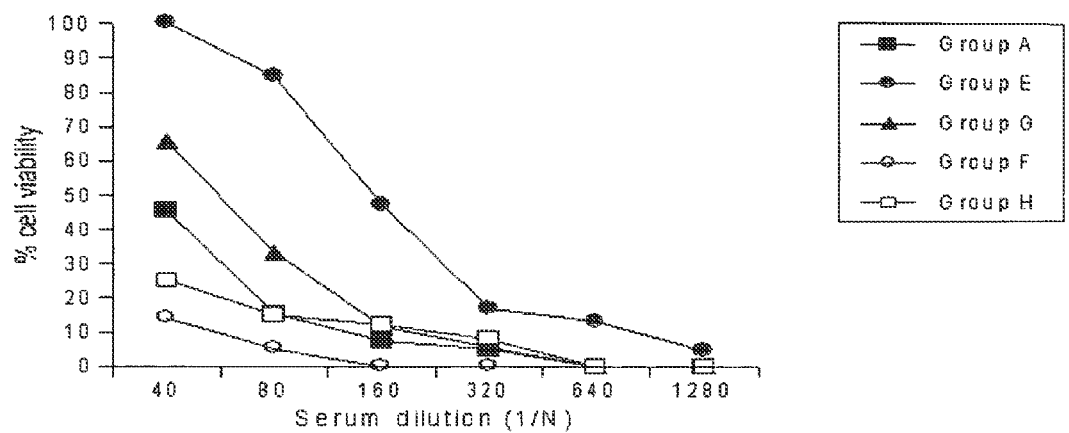
Figure 7B:
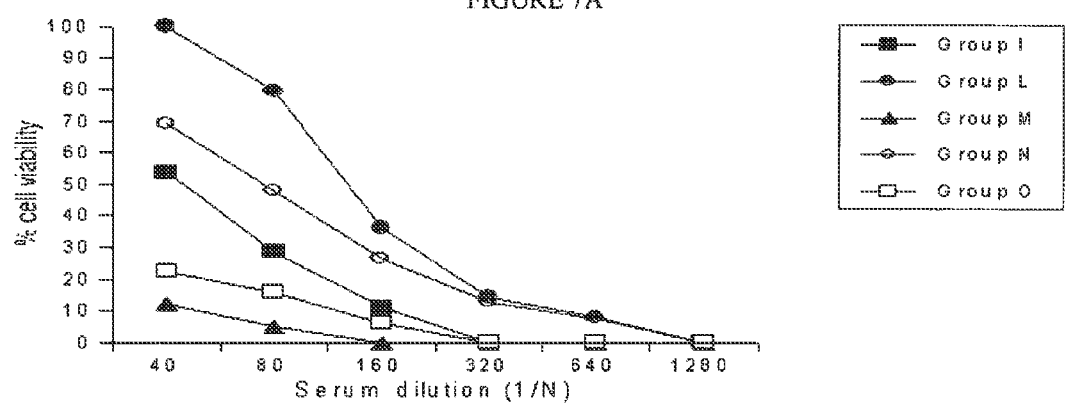
Figure 7C:
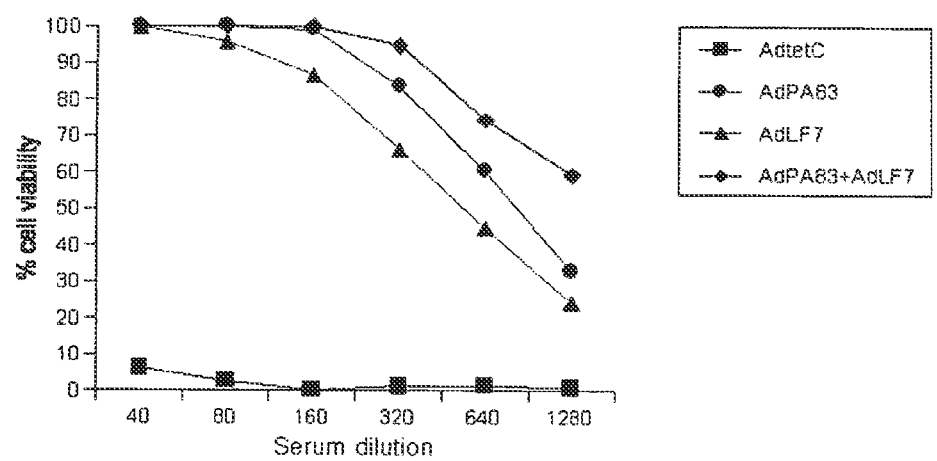

Immune inhibitor A is a secreted virulence protease from *Bacillus thuringiensis* and it specifically degrades two antibacterial proteins (cecropins and attacins) produced by an insect host (Dalhammar and Steiner 1984), suggesting that it may contribute to the overall virulence of *Bacillus thuringiensis*. *Bacillus thuringiensis* is highly resistant to the insect immune system due to its production of two factors, inhibitor A and inhibitor B, which selectively block the humoral defense system developed by insects against *Escherichia coli* and *Bacillus cereus* (Edlund 1976). Immune inhibitor A has been known to be a metalloprotease with similarity to the *Bacillus* thermoproteolyticus' thermolysin, the *Pseudomonas aeruginosa* elastase and the protease E-15 from *Serratia* (Dalhammar and Steiner 1984). Using a transcriptional immune inhibitor A'-lacZ fusion, it was shown that this protein expression is activated at the onset of sporulation (Grandvalet 2001). These results have shown for the first time that immune inhibitor A is expressed in *Bacillus anthracis* (FIGS. 2, 3, and 4) and that it is able to be expressed in spores with an increase during germination/outgrowth.

Spot 13

Eight peaks within the peptide mass fingerprint of spot 13 matched those of the protein with accession # gi|21399194 in the SWISS-PROT database (FIG. 3B). Like spot 12, spot 13 was named as a hypothetical protein predicted by GeneMark and also a predicted protein from the genome of *Bacillus anthracis* (Read T. D. et al., Science 296:2028-2033, 2002). By Q-TOF 2 mass spectrometer, we have also sequenced seven internal sequences of this predicated protein (Table 1). One of internal sequence with 15 amino acid residuals (QSEPVYETTLADLQK; SEQ ID NO: 22) from spot 13 was shown in FIG. 4C. This protein was listed as Hypothetical protein 1 with unknown functions (Huang 2004). It has recently been demonstrated that this protein induces apoptosis of macrophages (FIG. 13) and the protein has been assigned the name "germaxin".

Spot 19

Similarly, spot 19 was excised and analysed, and it was determined that although the peptide mass fingerprint of spot 19 matched a dihydropyridine sensitive L-type calcium channel beta subunit (accession # gi.vertline.21402368) (FIG. 3C) the entire sequence of this protein shares 69% identity to the germination protease, the product of the gpr gene of *Bacillus megaterium* (Sanchez-Salas and Setlow 1993). This protein has only 37% homology with rat dihydropyridine sensitive L-type calcium channel beta subunit (P54287). The DNA contained by the spores of the *bacillus* species was saturated with a group of small, acid-soluble proteins (SASP) that protect the DNA from a variety of harsh treatments and play a major role in spore resistance and long-term survival. The SASP-specific germination protease GPR degrades SASP, which also functions as the major energy reserve of the dormant spore, to amino acids during the first minute of *B. subtilis* spore germination (Tovar-Rojo 2003). SASP degradation is accompanied by increases in transcription, protein synthesis, and rapid growth (Sanchez-Salas 1992). This degradation was initiated by a sequence-specific protease called germination protease, which exhibits no obvious mechanistic or amino acid sequence similarity to any known class of proteases (Sanchez-Salas 1992). The germination protease is synthesized during sporulation as an inactive tetrameric zymogen termed P(46), which later autoprocesses to a smaller form termed P(41), which is active only during spore germination. According to published literature, the crystal structure of P(46) has been determined (Ponnuraj 2000). *Bacillus subtilis* mutants with an inactivated gpr.sup.− gene grew, sporulated, and triggered spore germination as did gpr.sup.+ strains. However, SASP degradation was very slow during germination of gpr.sup.− mutant spores, and in rich media the time taken for spores to return to vegetative growth was much longer in gpr.sup.− than in gpr.sup.+ spores (Sanchez-Salas and Setlow 1993).

Blocking the function of the GPR-like spore protease might be expected to produce a phenotype similar to that observed in *B. megaterium* and *B. subtilis* gpr mutants, namely decreased SASP degradation with accompanying retardation of germination (Sanchez-Salas and Setlow 1993). These observations collectively suggest that immunologic or pharmacologic targeting of this enzyme could deter spore germination. Degradation of the cortex, coat, and exosporium during spore germination (Liu 2004) may provide a unique window for drugs or vaccines to penetrate into spores for inactivation of core proteins that are biologically active.

Although this germination protease has not been documented until now in *Bacillus anthracis*, we found this protein was increased in the 2D Gel during the germinating stage, suggesting that this protein may play an important role in anthrax germination.

Spot 15

Five peaks within the peptide mass fingerprint of spot 15 matched those of the protein with accession # gi.vertline.21399147 in the SWISS-PROT database (FIG. 3D). Spot 15 only has an unknown protein name and may be a novel and anthrax-specific protein since its entire amino acid sequence fails to match proteins of other species.

Spot 21

Alanine racemase (EC 5.1.1.1) (spot 21) converts L-alanine, a germination-promoting compound to D-alanine, a germination inhibitor and essential component of the peptidoglycan found within the cell wall and spore cortex. It is hypothesized that Alanine racemase converts L-alanine to D-alanine in a hostile environment to inhibit germination and maximize survival potential (Kanda-Nambu 2000). Previous efforts have demonstrated that Alanine racemase is present in the exosporium layer (the outermost layer of spores in contact with the environment) of *B. anthracis* (Steichen 2003), and is both tightly adsorbed to exosporium and a major chemical trigger of germination in *B. cereus* (Todd 2003). Down-regulation of Alanine racemase during germination as revealed in this study (Table 1 and FIGS. 2A and 2B) corroborates the hypothesis that inhibition of this enzyme may be a prerequisite for *B. anthracis* spores to germinate. Expression of Alanine racemase in exosporium may allow inactivation of this enzyme by specific antibodies or inhibitors without the requirement for penetration into spores, and thereby minimizing survival potential of *B. anthracis* by triggering pre-mature germination before the spore reaches a favorable environment. Anti-Alanine racemase agents may even be used for decontamination of anthrax spores by inducing abortive germination.

Other Isolated Spots

Spot 48 was identified as L-arabinose transport ATP-binding protein araG. The araG protein belongs to the ABC transporter and plays a role in metabolizing L-arabinose as the sole carbon and energy source (Sa-Nogueira and Ramos 1997). Two molecular chaperones (heat shock protein 60; spot 26 and cpn 60; spot 27) and two energy-involved enzymes (ATP synthase; spot 41 and glyceraldehyde 3-phosphate dehydrogenase (GAPDH), C terminal domain; spot 47) have been up-regulated during spore germination. The elevated expression of molecular chaperones in germinating plant seeds suggests that the presence of higher levels of molecular chaperones is necessary to assist the rapid assembly of the oligomeric protein structures (Apuya 2001). In addition to the ten proteins that are regulated in expression during *B. anthracis* spore germination, we identified forty other proteins that are expressed in both dormant and germinating spores including a number of novel proteins demonstrated for expression in *B. anthracis* for the first time (Table 1 and FIGS. 2A and 2B). This proteomic database provides fundamental information for understanding the biology of anthrax spores. Some of these proteins may be essential to the viability of spores, and may also appear as novel candidates for drug and vaccine development.

Example 4: Construction of Replication Competent Adenovirus (RCA)-Free Ad Vectors Encoding *B. anthracis* PA63 and LF7

Shuttle plasmids pAdApt-PA63 and pAdApt-LF7 containing the *B. anthracis* PA63 and LF7 fragments, respectively, were constructed by insertion of PA63 and LF7 fragments into pAdApt (provided by Crucell). PA63 contains a biologically active portion (amino acids 175 to 764) of *B. anthracis* PA corresponding to the protease-cleaved PA63 fragment of the full-length 83-KD protein (Price, 2001). LF7 is an immunogenic but atoxic fragment of LF. The catalytic domain of LF resides in the C-terminal part where a HEXXH zinc-metalloprotease consensus sequence (residues 686-690) was identified. Mutations of the critical residues abolish lethal toxin activity and binding of $Zn^{2+}$ to LF (Mock and Fouet 2001). Toxicity of LF was inactivated in LF7 by substitution of Cysteine for E-687 within the catalytic site of LF (Klimpel 1994). RCA-free E1/E3-defective adenovirus serotype 5 (Ad5) vectors encoding PA63 (rAdCMV-PA63) and LF7 (rAdCMV-LF7) were generated by co-transfecting pAdApt-PA63 and pAdApt-LF7, respectively, with the Ad backbone plasmid pJM17 (Shi 2001) (provided by F. Graham) into PER. C6 packaging cells (Murakami 2002) (provided by Crucell) followed by plaque purifications. RCA-free Ad vectors are generated using this protocol because PER.C6 cells contain Ad5 nucleotides 459-3510, which precludes double crossover-type homologous recombination with pAdApt-based plasmids that do not contain any overlapping sequences (Murakami 2002). Elimination of RCA in Ad stocks reduces the risk of exposure to the potential oncogene E1a and pathogenesis induced by replication of Ad in the host.

Example 5: Immunization of Mice Against PA and LF by Intranasal and Topical Application of Ad-Vectored Vaccines To determine whether animals can be effectively immunized against the anthrax toxin by intranasal and topical application of Ad-vectored vaccines, AJ and ICR mice were immunized as outlined in Table 2. Briefly, three-month-old mice were immunized by intranasal and topical application of Ad-LF7, Ad-PA63, and a control Ad vector AdCMV-tetC as described (Shi 2001). Vectors, dosages, and frequencies (Groups A-O) are described in C2 and Table 2. Specifically, immunizations comprised one of: Ad-LF7, an Ad5 vector encoding anthrax LF7; Ad-PA63, an Ad5 vector encoding anthrax PA63; or AdCMV-tetC, an Ad5 vector encoding the tetanus toxin C-fragment (used here as a control) (Shi 2001). The AJ mice were susceptible to *B. anthracis* Sterne spores (Welkos and Friedlander 1988), whereas the ICR mice were more resistant. Animals were immunized on Day 0, followed by two booster applications on Days 30 and 210, respectively.

TABLE 2

Immunization of mice by Ad-vectored anthrax vaccines

| Group | Strain | Immunization |
|---|---|---|
| A | AJ | Topical application of $10^8$ pfu of Ad-LF7 |
| B | AJ | Topical application of $10^7$ pfu of Ad-LF7 |
| C | AJ | Topical application of $10^6$ pfu of Ad-LF7 |
| D | AJ | Topical application of $10^8$ pfu of AdCMV-tetC |
| E | AJ | Intranasal instillation of $10^7$ pfu of Ad-LF7 |
| F | AJ | Topical application of $10^8$ pfu of Ad-PA63 |
| G | AJ | Topical application of $10^8$ pfu of Ad-LF7 and $10^8$ pfu of Ad-PA63 |
| H | AJ | Intranasal instillation of $10^7$ pfu of Ad-PA63 |
| I | ICR | Topical application of $10^8$ pfu of Ad-LF7 |
| J | ICR | Topical application of $10^7$ pfu of Ad-LF7 |
| K | ICR | Topical application of $10^8$ pfu of AdCMV-tetC |
| L | ICR | Intranasal instillation of $10^7$ pfu of Ad-LF7 |
| M | ICR | Topical application of $10^8$ pfu of Ad-PA63 |
| N | ICR | Topical application of $10^8$ pfu of Ad-LF7 and $10^8$ pfu of Ad-Pa63 |
| O | ICR | Intranasal instillation of $10^7$ pfu of Ad-PA63 |

Example 6: Protection of Mice by Ad-Vectored Vaccines Against *B. anthracis* Sterne Spores Control and immunized animals were challenged with *B. anthracis* Sterne spores. Live spores were inoculated into AJ mice by intranasal instillation, to simulate inhalational anthrax. ICR mice were very resistant to inhalational Sterne spores, and challenge studies in this mouse strain were thus carried out by intraperitoneal injection (i.p.) of live spores. Three-month-old mice were immunized by intranasal and topical application of Ad-LF7, Ad-PA63, and a control Ad vector AdCMV-tetC as described (Shi 2001). Vectors, dosages, and frequencies (Groups A-O) are described in C2 and Table 2. One month after the last boost when mice were 11 months old, AJ mice were challenged by intranasal instillation of *B. anthracis* Sterne spores in a volume of 10 µl water containing $10^5$ cfu (colony-forming units). ICR mice were challenged by i.p. injection of Sterne spores in a volume of 50 µl water containing $10^8$ cfu. The 50% lethal dose ($LD_{50}$) of Sterne spores was $10^4$ cfu for 3-month-old AJ mice after inhalation; and $10^7$ cfu for 3-month-old ICR mice after i.p. injection. This *B. anthracis* Sterne 34F2 vaccine strain (Colorado Serum Company, Denver, Colo.) is nonencapsulated ($pXO2^-$) but toxigenic ($pXO1^+$) with PA and LF expressed from the pXO1 plasmid. Spores were grown in the supplemented nutrient broth medium (Hanson 1964) with modifications [0.8% Bacto nutrient broth, 0.1% KCl, 0.012% $MgSO_4$, 1 mM $Ca(NO_3)_2$, 10 μM $MnCl_2$, 1 μM $FeSO_4$, pH 7.6] at 37° C. with shaking. Dormant anthrax spores were purified from death-phase (48-h) culture by centrifugation of spores, vegetative cells and cell debris through gradients of Renografin-60 (Bracco Diagnostic, Princeton, N.J.) in conjunction with extensive washes as described (Steichen 2003). Purified dormant anthrax spores were stored in water at 4° C.

Challenged animals were monitored daily for survival up to 30 days. Difficult breathing was taken as the disease endpoint. No symptoms or deaths occurred 14 days post-challenge. As shown in FIG. 5A-5E, the Ad vector encoding the immunogenic but atoxic LF fragment (LF7) was significantly more effective than its counterpart encoding PA63 in protecting mice (both AJ and ICR) against live Sterne spores, and the Ad-vectored nasal vaccine is more potent than its epicutaneous counterpart. The data depicted in FIG. 5A-5E was plotted as % death versus days after challenge. Numbers in parentheses after each Group represent the number of animals that received each treatment.

Intranasal instillation of 10.sup.7 pfu of Ad-LF7 was able to protect 89% AJ (Group E in FIG. 5A) and 77% ICR (Group L in FIG. 5C) mice against a lethal dose of anthrax spores. Topical application of 108 pfu Ad-LF7 was able to protect 50% AJ (Group A in FIG. 5A) and 36% ICR (Group I in FIG. 5C) mice. Intranasal and topical application of Ad-PA63 was not very effective in protecting animals (Groups F and H in FIG. 5B; Group M and 0 in FIG. 5D). Co-administration of Ad-LF7 and Ad-PA63 (Group G in FIG. 5B; Group N in FIG. 5D) was as effective as Ad-LF7 alone. Greater than 87% animals immunized with the control vector AdCMV-tetC (Group D in FIG. 5A; Group K in FIG. 5C) were killed by anthrax spores within 9 days.

These results demonstrate that an Ad vector encoding an immunogenic but atoxic LF fragment (LF7) is more effective in protecting animals against inhalational anthrax than a counterpart encoding PA63. Eighty-nine % and 50% AJ mice could be protected against inhalational anthrax following intranasal instillation and topical application of Ad-LF7, respectively. PA63 was less immunogenic than LF7 in the mouse genetic background.

Example 7: Elicitation of Anti-PA and -LF Antibodies by Ad-Vectored Anthrax Vaccines To determine whether protection against anthrax as shown in FIG. 5A-5E was mediated, at least in part, by the elicitation of toxin-neutralization antibodies following administration of Ad-vectored anthrax vaccines, anti-PA and -LF antibody titers were analyzed by ELISA and mouse macrophage protection assay through toxin neutralization.

ALT (Groups A-H) and ICR (Groups I-O) mice were immunized against PA and LF as described in Examples 5 and 6, above. Serum samples were harvested 1, 2, and 8 months after the primary immunization, and analyzed for anti-PA and -LF antibodies by ELISA as described (Shi 2001) with purified PA and LF proteins (List Biological Laboratories, Inc.), respectively, as the capture antigen (1 ng protein per well). FIG. 6A-6D shows that Ad-LF7 elicited higher ELISA antibody titers than Ad-PA63. Additionally, Ad-vectored nasal vaccine was more effective in inducing an antibody response than its epicutaneous counterpart. These results show that the level of ELISA antibody titers was correlated with that of protection (FIG. 5A-5E).

Additionally, serum samples harvested 8 months after the primary immunization (one month after the last booster application) were analyzed for toxin-neutralization antibodies as described for a mouse macrophage protection assay (Price 2001) with modifications. Briefly, sera from all immunized animals in a group were pooled in equal amounts, serially diluted, and incubated with PA and LF proteins (List Biological Laboratories, Inc.). A final concentration of 0.06 .mu.g PA and 0.12 .mu.g LF with or without neutralization was added to 10.sup.5 mouse monocyte-macrophage RAW 264.7 cells (ATCC) per well in a 96-well plate. At the end of the incubation 16 hour incubation period, 0.05 .mu.g MTT (3-[4,5-dimethylthiazol-2-yl]-2,5-diphenyltetrazolium bromide; Sigma) per well was added, followed by a 1-h incubation. Cells that survive exposure to PA-LF are able to oxidize MTT to an insoluble purple pigment, thus providing a proportional measure of the viability of the cells. At the end of the incubation period, the level of survival was determined using a microplate reader at OD.sub.540. Shown in FIG. 7A-7C is the percent cell viability. Survival of control cells without exposure to PA+LF was arbitrarily defined as 100%. FIG. 7A-7C shows that Ad-LF7 elicited higher toxin-neutralization antibody titers than Ad-PA63. Also, the Ad-vectored nasal vaccine was more effective in inducing an antibody response than its epicutaneous counterpart.

Overall, as shown in FIGS. 6A-6D and 7A-7C, the highest ELISA and toxin-neutralization antibody titers were induced by intranasal instillation of Ad-LF7. Topical application of Ad-LF7 was also quite effective, whereas the immunogenicity of PA63 was low. The level of ELISA antibody titers (FIG. 6A-6D) and toxin-neutralization antibody titers (FIG. 7A-7C) were both correlated with that of protection (FIG. 5A-5E). Due to the close correlation between toxin-neutralization antibody titers and protection of animals against live anthrax spores, it is thus logical to use the toxin-neutralization antibody titer as a standard in determining the potency of an experimental anthrax vaccine.

Example 8: Dissemination and Degradation of PA DNA Following Topical Application of Ad-PA63

To analyze the safety margin of Ad-vectored epicutaneous anthrax vaccines, DNA was extracted from various tissues of AJ mice at different time points following topical application of Ad-PA63, followed by PCR-based amplification of the PA DNA. Specifically, AJ Mice were immunized by topical application of 108 pfu of Ad-PA63 as described in Examples 5 and 6, above. At indicated time points, total DNA was extracted from the tissues and amplified by PCR using specific primers. The forward primer 5'-AGTACAAGTGCTGGACCTACGGTTCCAGAC-3' (SEQ ID NO:39) and reverse primer 5'-TCCTATCTCATAGCCTTTTTTAGAAAAGAT-3' (SEQ ID NO:40) were used to amplify the nearly full-length 1.7 kb PA63 fragment. The forward primer 5'-TATCCTTCTAAAAACTTGGCGCCAATCGCA-3' (SEQ ID NO:41) and reverse primer 5'-GATCACTAGGATTAACCGCCGCTATCCGCC-3' (SEQ ID NO:42) were used to amplify a 0.3 kb subfragment encompassing 18% of the PA63 fragment. The data were presented as the number of animals containing detectable signals for a specific tissue per total number of animals analyzed. DNA was extracted using DNAZOL solution. One .mu.g of DNA was amplified for 39 cycles at optimized annealing temperatures. Amplified DNA fragments were fractionated in 1% agarose gel and stained with ethidium bromide.

As summarized in Table 3, the nearly full-length PA63 gene could be amplified from the skin at the administration site both 3 hours and 1 day post-inoculation. The nearly full-length gene was undetectable in skin DNA after 2 days or in DNA extracted from other tissues. However, a sub-fragment of the PA63 DNA was amplified from liver, spleen, heart, lung, brain, kidney, whole blood, or lymph nodes using a different set of primers. The PA63 subfragment was amplifiable from a wide variety of tissues 1 day postimmunization, but not 3 hr after topical application. No foreign DNA was detectable in any of the tissues a month post-inoculation. Results suggest that vector DNA delivered by a vaccine patch may be acquired by putative antigen-presenting cells (APC), followed by degradation and dissemination into deep tissues including lymphoid organs. The elimination of foreign DNA in a month post immunization highlights the safety of epicutaneous vaccines. The transient expression of antigens in the skin following topical application of vectors may also minimize antigen-induced apoptosis of T lymphocytes that may deplete the pool of memory T cells (Swain 1999).

These results show that the mouse skin can absorb Ad-vectored vaccines. Ad vectors absorbed by the skin is rapidly degraded and disseminated systemically. One month postimmunization, no trace amount of the antigen DNA could be amplified by PCR in any of the tissues examined, indicating that the skin is able to protect the host's genetic integrity by degrading absorbed environmental DNA. This leads to the conclusion that topical application of Ad vectors is safe because the vector DNA does not persist.

erate plasmid pZErO-nirB. Amplification of a MCS from plasmid pBluescript II KS (Stratagene) with PCR was also performed, and the amplified MCS was inserted into the XhoI-StuI site of pZErO-nirB to generate plasmid pZErO-nirB-MCS. Plasmid pnirBVaxin was generated by the insertion of a synthetic T7 terminator into the SacI-StuI site of pZErO-nirB-MCS to generate. The T7 terminator was made by annealing the following two synthetic oligonucleotides:

CCATAACCC CTTGGGGCCT CTAAACGGGT CTT-GAGGGGT TTTTTGCTGA AAGGAGG (SEQ ID NO:43) and TCGA GGTATTGGG GAACCCCGGAGATTTGC-CCA GAACTCCCCA AAAAACGACT TCCTCC (SEQ ID NO:44).

The plasmid p.lambda.tsP.sub.RVaxin was constructed by replacing the nirB promoter in plasmid pnirBVaxin with a fragment containing the bacteriophage lambda P.sub.R promoter-cro ribosome binding site-ATG codon in conjunction with the .lambda.cI857 variant of the XcI gene which codes for a temperature-sensitive repressor of P.sub.R. The cI857 product represses P.sub.R at 32.degree. C., but allows transcription from the P.sub.R promoter at 42.degree. C. (Queen 1983). The lambda PR promoter-cI857 repressor unit was amplified from plasmid pCQV2 (Queen 1983) (provided by C. Queen) and inserted into the AflIII-XhoI site of pnirB-Vaxin to replace the nirB promoter.

Recombinant plasmids encoding the *B. anthracis* PA63 were constructed by amplifying the PA63 gene with PCR from plasmid pCPA (provided by D. Galloway) which contains a biologically active portion (corresponding to amino acids 175 to 764) of *B. anthracis* PA corresponding to the protease-cleaved PA63 fragment of the full-length 83-KD protein (Price 2001). The PA63 fragment was inserted into the XhoI-XbaI site of pnirBVaxin and p.lambda.tsP.sub.RVaxin to generate plasmids pnirB-PA63 (PA63 driven by nirB promoter) and p.lambda.tsP.sub.R-PA63 (PA63 driven by .lambda.P.sub.R promoter), respectively.

TABLE 3

Summary of PA63 DNA dissemination in AJ mice following topical application of Ad-PA63

| | Skin[a] | LN[b] | Heart | Spleen | Liver | Kidney | Blood | Brian | Lung |
|---|---|---|---|---|---|---|---|---|---|
| II. full-length PA63 fragment | | | | | | | | | |
| 3 hr | 3/3 | 0/3 | 0/3 | 0/3 | 0/3 | 0/3 | 0/3 | 0/3 | 0/3 |
| 1 day | 3/3 | 0/3 | 0/3 | 0/3 | 0/3 | 0/3 | 0/3 | 0/3 | 0/3 |
| 1 month | 0/3 | 0/3 | 0/3 | 0/3 | 0/3 | 0/3 | 0/3 | 0/3 | 0/3 |
| II. Subfragment of PA63 DNA | | | | | | | | | |
| 3 hr | 3/3 | 0/3 | 0/3 | 0/3 | 0/3 | 0/3 | 0/3 | 0/3 | 0/3 |
| 1 day | 3/3 | 3/3 | 3/3 | 2/3 | 3/3 | 2/3 | 3/3 | 1/3 | 2/3 |
| 1 month | 0/3 | 0/3 | 0/3 | 0/3 | 0/3 | 0/3 | 0/3 | 0/3 | 0/3 |

[a]Administration site (abdominal skin);
[b]pooled inguinal, cervical, and brachial lymph nodes.

Example 9: Construction of Recombinant Plasmids for Expression of *B. anthracis* Antigens in *E. coli* Vectors The plasmid pnirBVaxin with the *E. coli* nirB promoter inserted upstream from a multiple cloning site (MCS) was constructed by amplifying the nirB promoter including its ATG initiation codon and ribosome binding site with polymerase chain reaction (PCR) from plasmid pTET-nir (Chatfield 1992) (provided by J. McGhee). The amplified fragment containing the nirB promoter was then inserted into the AflIII-XhoI site of plasmid pZErO™-2 (Invitrogen) to gen- Recombinant plasmids encoding the N-terminal region (amino acids 10-254 containing the PA binding domain) of *B. anthracis* LF (LF4 fragment) were constructed by excising the LF4 fragment from plasmid pCLF4 (Price 2001) (provided by D. Galloway) followed by insertion into the XhoI-NotI site of pnirBVaxin and p.lambda.tsP.sub.RVaxin to generate plasmids pnirB-LF4 (LF4 driven by nirB promoter) and p.lambda.tSP.sub.R-LF4 (LF4 driven by .lambda.P.sub.R promoter), respectively. The LF4 fragment was amplified by PCR from plasmid pCLF4 and inserted into the BamHI-XhoI site of pCAL-n-FLAG to generate plasmid pCAL-n-FLAG-LF4 (LF4 driven by the T7 promoter).

Recombinant plasmids encoding the full length but atoxic *B. anthracis* LF (LF7 fragment) were constructed by amplifying the LF7 fragment with PCR from plasmid pAdApt-LF7 (provided by D. Galloway) followed by insertion of the LF7 fragment into the BamHI-XhoI site of pCAL-n-FLAG to generate plasmid pCAL-n-FLAG-LF7 (LF7 driven by T7 promoter). The LF7 fragment was subsequently excised from pCAL-n-FLAG-LF7 and inserted into the BamHI-SacI site of pnirBVaxin and p.lambda.tsP.sub.RVaxin to generate plasmids pnirB-LF7 (LF7 driven by nirB promoter) and p.lambda.tsP.sub.R-LF7 (LF7 driven by kPR promoter), respectively. The LF4 fragment in pCLF4 was replaced by the LF7 fragment to generate plasmid pCMV-LF7 (LF7 driven by the cytomegalovirus [CMV] early promoter). The catalytic domain of LF resides in the C-terminal part where a HEXXH zinc-metalloprotease consensus sequence (residues 686-690) is identified. Mutations of the critical residues abolish lethal toxin activity and binding of $Zn^{2+}$ to LF (Mock, 2001). Toxicity of LF was inactivated in LF7 by substitution of Cysteine for E-687 within the catalytic site of LF (Klimpel 1994).

Figure 8:
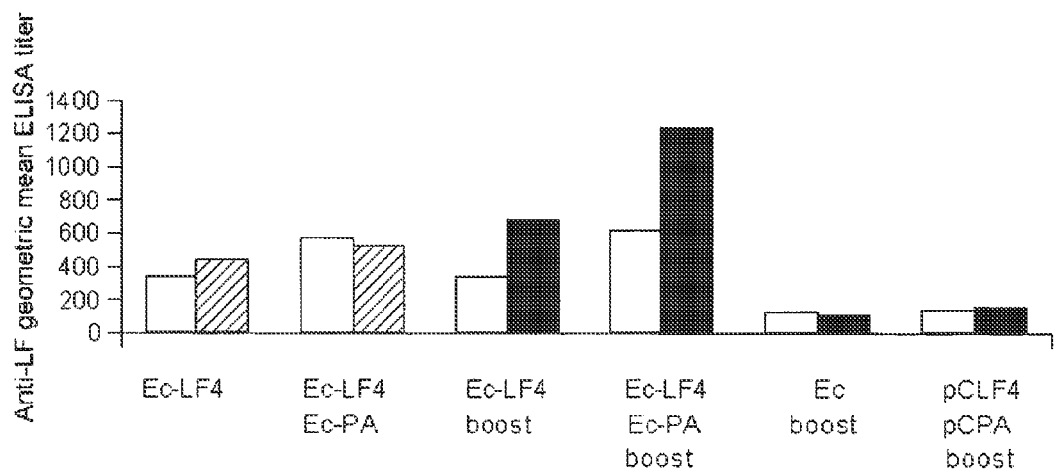

Example 10: Immunization of Animals by Topical Application of *E. coli*-Vectored Vaccines To determine whether animals can be immunized by topical application of *E. coli*-vectored vaccines and whether vectors expressing PA and LF also confer synergy when combined, as previously demonstrated for DNA-based vaccines (Price 2001), mice were immunized by topical application of *E. coli* vectors expressing LF4, PA63, or both, and determination of antibody titers against LF was subsequently performed (FIG. 8).

Young (2-3 months old) female ICR mice (Harlan) were immunized by topical application of *E. coli* vectors harboring the plasmids pnirB-LF4, pnirB-PA63, or a combination of both. Topical application was carried out by pipetting $5.\times 10^9$ cfu of *E. coli* BL21-CodonPlus cells (Stratagene) harboring each plasmid onto pre-shaved abdominal skin of a mouse followed by covering the vector as a thin film over naked skin with a piece of the Tegaderm patch (3M) as described (Shi 2001). *E. coli* cells were harvested during mid-log phase and washed twice in PBS prior to administration. Unabsorbed vectors were washed away in an hour. As a positive control, DNA-based vaccination was conducted by intramuscular (IM) injection of pCLF4 and pCPA DNA (Price 2001) (100 .mu.g each) into the hind leg quadriceps as described (Shi 2001). Serum samples were assayed for anti-LF antibodies 1 and 2 months after the primary immunization. Titers of anti-LF IgG were determined by ELISA as described (Shi 2001) using purified LF protein (provided by D. Galloway) as the capture antigen. Briefly, serum samples and peroxidase-conjugated goat anti-mouse IgG (Promega) were incubated sequentially on the plates with extensive washing between each incubation. The end-point was calculated as the dilution of serum producing the same $OD_{490}$ as a 1/100 dilution of pre-immune serum. Sera negative at the lowest dilution tested were assigned endpoint titers of 1. FIG. 8 shows the tier results obtained one month post immunization but prior to any boosts, two months post immunization but prior to any boosts, and two month post immunization where a boost was give one month post immunization.

This demonstrates that animals can be immunized against an anthrax antigen following topical application of a recombinant *E. coli* vector expressing the antigen and suggests that the cutaneous immune system may be rapidly activated when the outer layer of skin is in contact with *E. coli* cells at the specified concentration. Further, an unidentified host defense mechanism may subsequently disrupt *E. coli* cells, capture the antigen from within, and present the exogenous antigen to the host immune system in eliciting an immune response. The commercial impact of this finding is great owing to the potency of this regimen (as this is more effective than IM injection of DNA), simplicity in mass production of *E. coli* vectors, elimination of problems associated with needle injections, and the high biosafety margin of laboratory *E. coli* strains.

In an attempt to optimize the potency of *E. coli*-vectored epicutaneous vaccines, the anthrax antigen was inserted downstream from a variety of prokaryotic and eukaryotic promoters as described above, followed by epicutaneous immunization of animals with *E. coli* vectors harboring the same antigen driven by different promoters, and subsequently determined the anti-LF antibody response (see FIGS. 9 and 10A-10B).

A/J mice were immunized by topical application of recombinant *E. coli*-vectored vaccines with one booster application a month postimmunization, as described in Example 6. Specifically, $5.\times 10^9$ cfu of *E. coli* BL21-CodonPlus cells harboring a plasmid encoding LF7 mixed with the same number of *E. coli* cells harboring another plasmid encoding PA63 driven by the same promoter was administered onto the skin of each animal. Serum samples were assayed for anti-LF antibodies 1 and 2 months after the primary immunization. Animals in the control group received administrations of *E. coli* cells harboring p.lambda.tsP.sub.RVaxin.

Figure 9:
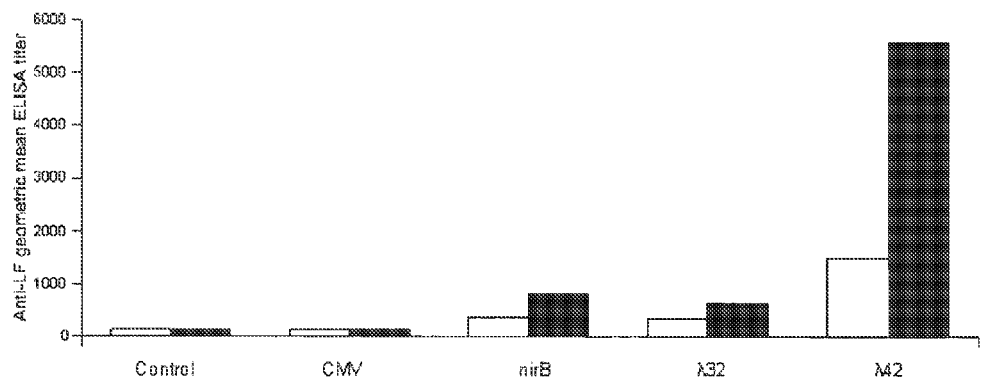
Figure 10A:
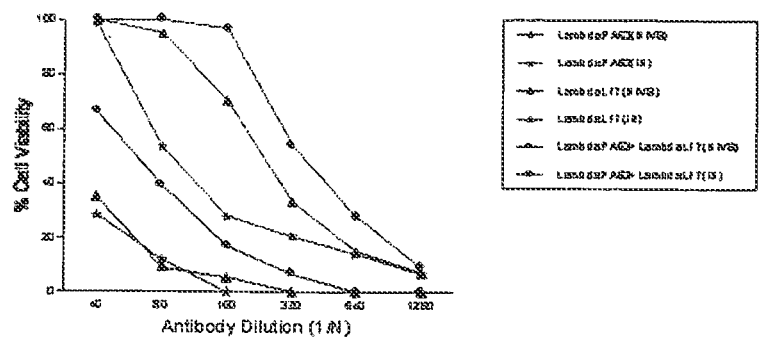
FIGS. 10A-B. Neutralizing antibodies against anthrax PA and LF elicited by intranasal and topical application of *E. coli* vectors expressing PA63 and LF7, respectively.
Figure 10B:
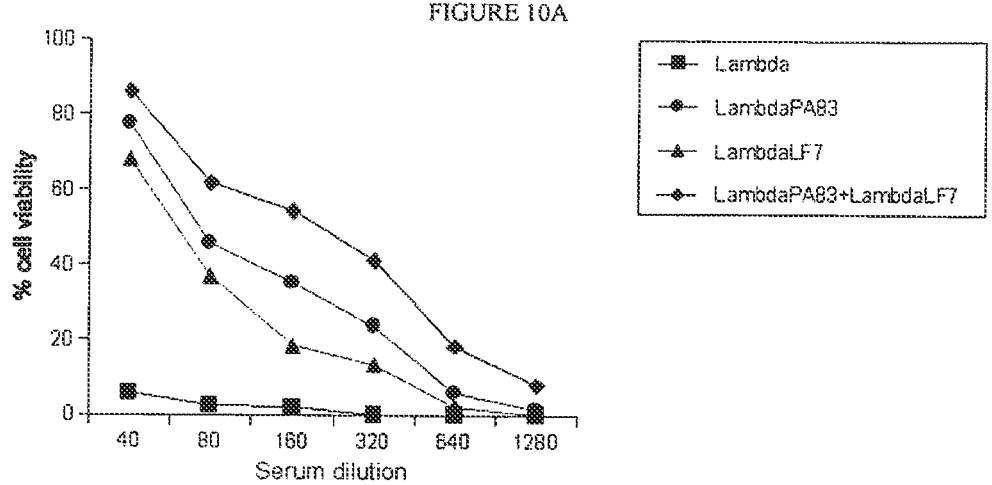

These results are shown in FIG. 9 which shows that the temperature-induced lambda PR promoter is potent in eliciting an immune response against the expressed antigen, even more effective than the *E. coli* nirB promoter. LF7 driven by the eukaryotic CMV promoter did not elicit any detectable antibody response. The same pattern of antibody response was reproduced in ICR mice (data not shown). Similar responses against PA were also generated when sera were analyzed with ELISA using PA83 protein (provided by D. Galloway) as the capture antigen.

It is possible that the potency of *E. coli*-vectored epicutaneous vaccine is correlated with the level of antigen expression. The temperature-induced lambda $P_R$ promoter may be more transcriptionally active than other promoters tested. Failure of the eukaryotic CMV promoter to generate an effective epicutaneous vaccine in the *E. coli* setting suggests that the antigen protein may be expressed in *E. coli* cells instead of the animal's own cells. The temperature-sensitive lambda $P_R$ promoter-c1857 repressor provides a unique system for production of exogenous antigens that may impede the growth of *E. coli* cells.

Additionally, AJ mice were immunized by intranasal and topical application of *E. coli* vectors expressing PA63 and LF7. Sera were serially diluted and incubated with PA+LF, and added to RAW264.7 cells as described in Example 7. Cell viability was determined by the MTT assay. The data is plotted in FIGS. 10A and 10B, which demonstrates that the *E. coli*-vectored nasal vaccine is more potent than the *E. coli*-vectored epicutaneous vaccine. Additionally, it is apparent that LF7 is more immunogenic than PA63.

Figure 11A:
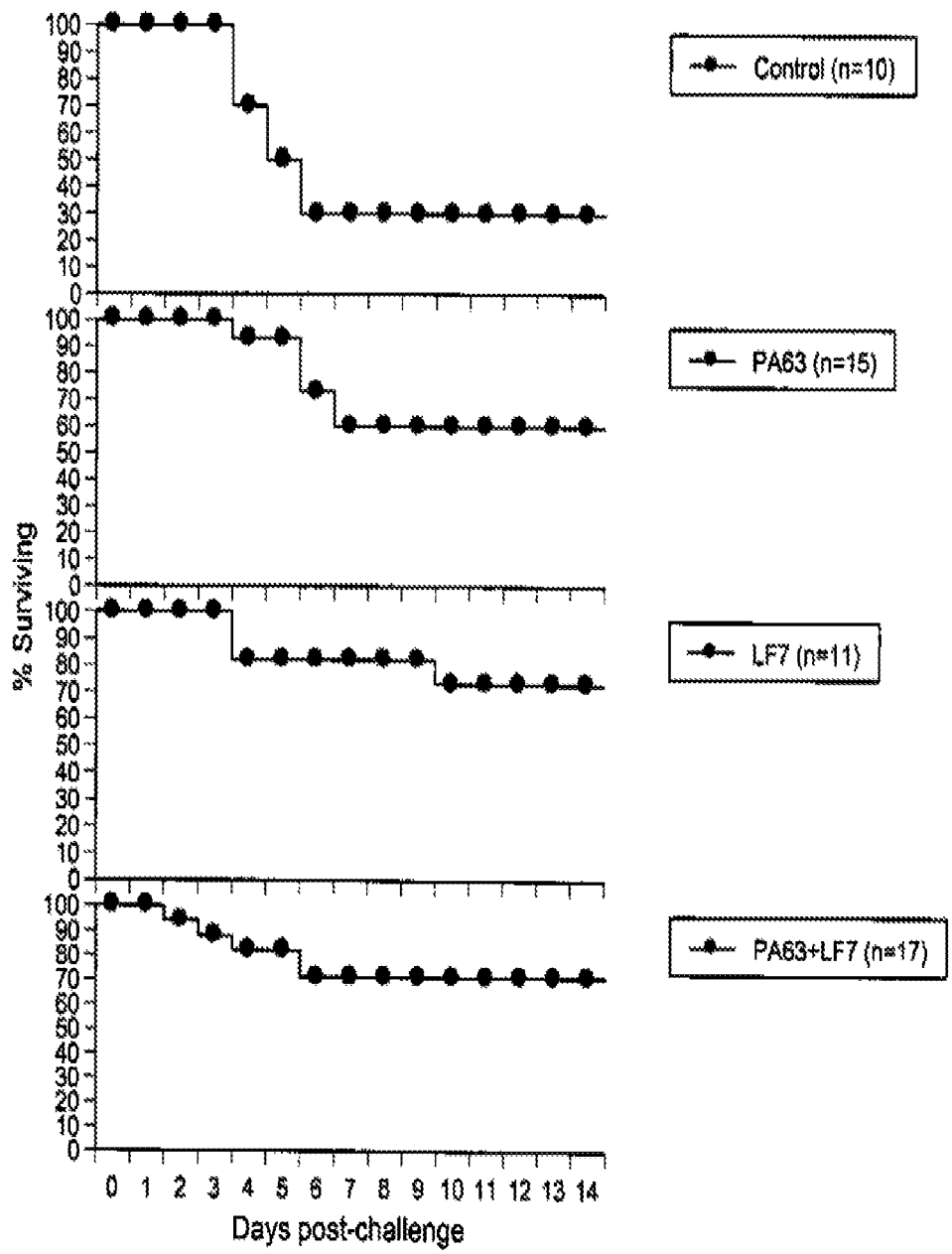
FIG. 11A-B. Protection of mice against inhalation anthrax by topical application of *E. coli*-vectored epicutaneous vaccines.
Figure 11B:
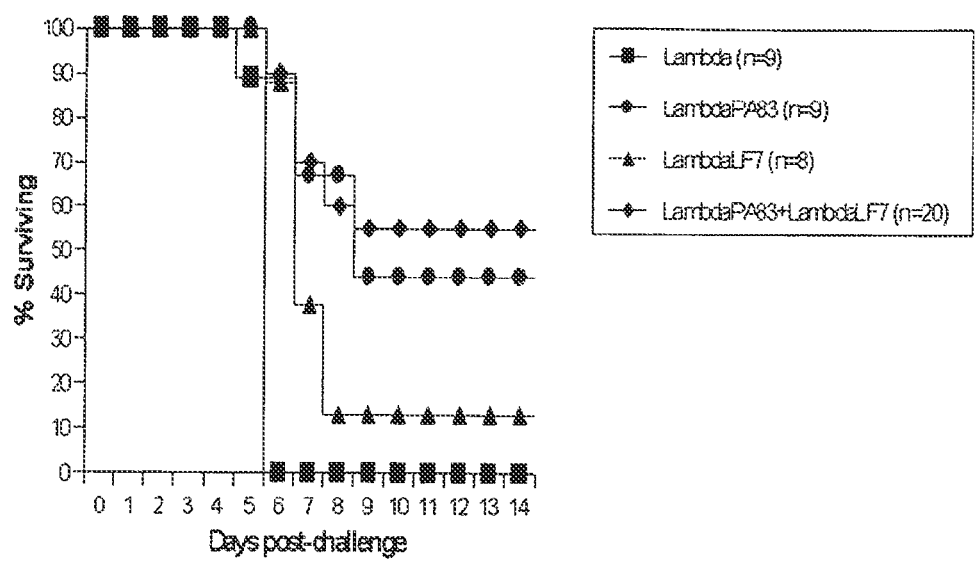

Furthermore, AJ mice immunized by topical application of *E. coli* vectors expressing LA63 and LF7 driven by the temperature-sensitive lambda promoter were challenged by intranasal inoculation of *B. anthracis* Sterne spores as described in Example 6, above. The challenge results shown in FIGS. 11A and 11B show that topical application of *E. coli*-vectored epicutaneous vaccines protects animals against inhalational anthrax.

Example 11: Induction of Apoptosis and Death of RAW 264.7 Cells by Germaxin

The mouse macrophage-like RAW 264.7 cells were incubated for one day with PBS, 25 ng/ml *E. coli* control protein or germaxin at concentrations of 25 ng/ml or 250 ng/ml. Germaxin was obtained by purification through an affinity column from *E. coli* cells expressing *B. anthracis* germaxin.

Figure 12:
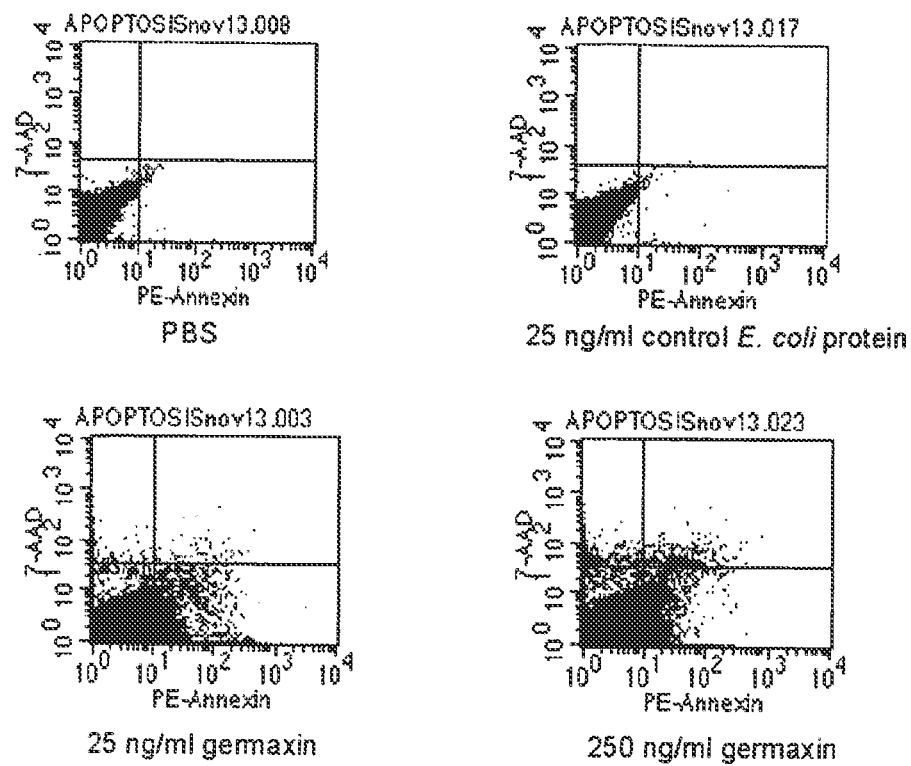
FIG. 12. Induction of apoptosis and death of RAW 264.7 cells by germaxin.

After incubation, cells were stained with Annexin V to detect apoptosis, and 7-AAD for determining cell death by flow cytometry. As shown in FIG. 12, there was significant increase in both apoptosis and cell death in those cells incubated with either concentration of germaxin in comparison with those incubated with PBS or the *E. coli* control protein. Additionally, the levels of apoptosis and cell death show little variation between cells incubated with the two concentrations of germaxin.

Example 12: Specificity of Germaxin to Induce Apoptosis in Macrophages

To determine whether germaxin's ability to induce cell death and apoptosis was specific to any types of cells, lung lavage and splenocytes were harvested and cultured from an AJ mouse. Macrophages present in the lung lavage culture were marked with an antibody against mouse CD11b (red cells in upper half of FIG. 13), and T-cells present in the splenocyte culture were marked with an antibody against mouse CD3 (red cells in lower half of FIG. 13). Cells were exposed to PBS, 25 ng/ml *E. coli* control protein, or 25 ng/ml *B. anthracis* germaxin (germaxin is described in Table 1).

One day later, apoptotic cells were identified by the Tunel assay (see arrows in upper right panel of FIG. 13). These results demonstrate that the *B. anthracis* germaxin protein induces the apoptosis of macrophages but not of T-cells.

The invention will now be further described by the following numbered paragraphs:

1. A *Bacillus anthracis* germination/outgrowth-associated spore protein corresponding to Spot 12 (Accession # NP_843763), wherein the protein has a peptide fingerprint mass spectra as depicted in FIG. 3A.

2. A *Bacillus anthracis* germination/outgrowth-associated spore protein corresponding to Spot 13 (Accession #: NP_655179), wherein the protein has a peptide fingerprint mass spectra as depicted in FIG. 3B.

3. A *Bacillus anthracis* germination/outgrowth-associated spore protein corresponding to Spot 19 (Accession # NP_846769), wherein the protein has a peptide fingerprint mass spectra as depicted in FIG. 3C.

4. A *Bacillus anthracis* germination/outgrowth-associated spore protein corresponding to Spot 15 (Accession # NP_655132), wherein the protein has a peptide fingerprint mass spectra as depicted in FIG. 3D.

5. A *Bacillus anthracis* germination/outgrowth-associated spore protein that is up- or down-regulated during germination by at least 30%, wherein the protein corresponds to Spot 21 (Accession # NP_654182), 24 (Accession # NP_846918), 27 (Accession # NP_654198), 41 (Accession # NP_847705), 47 (Accession # NP_653587), or 48 (Accession # NP_846171).

6. Novel *Bacillus anthracis* spore proteins corresponding to Spots 17 (Accession # NP_657537), 18 (Accession # NP_658120), 20 (Accession # NP_653598), 28 (Accession # NP_242212), 49 (Accession # NP_654492), 50 (Accession # NP_654728).

7. A method of immunization in an animal and/or a method of inducing a systemic immune response or systemic therapeutic response to a gene product, in an animal, comprising administering a vector that contains and expresses a nucleic acid molecule encoding the gene product, in an amount effective to induce the response, wherein the immunization and/or systemic immune response and/or systemic therapeutic response affords the animal protection against challenge with *B. anthracis*.

8. A method of immunization in an animal and/or a method of inducing a systemic immune response or systemic therapeutic response to a gene product, in an animal, comprising administering a vector that contains and expresses a nucleic acid molecule encoding the gene product, in an amount effective to induce the response, wherein the nucleic acid molecule encodes the *Bacillus anthracis* spore protein of any of paragraphs 1-6 or a portion thereof alone or in combination.

9. A vaccine or immunogenic composition against *Bacillus anthracis* comprising a spore protein as described in any of paragraphs 1-6, or a fragment thereof, or a genetic vector encoding a spore protein as described in any of paragraphs 1-6, or a fragment thereof, and optionally an excipient and/or adjuvant and/or a suitable carrier or diluent.

10. A method of preparing the vaccine or immunogenic composition of paragraph 9.

11. A method of treating an animal after suspected or real exposure to *B. anthracis* comprising administering an effective amount of one or more inhibitors to one or more of the spore proteins of paragraphs 1-6.

12. The method of any of paragraphs 7, 8 or 11, wherein the animal is a vertebrate.

13. The method of paragraph 12 wherein the vertebrate is a mammal.

14. The method of paragraph 13 wherein the mammal is a human or a companion or domesticated or food- or feed-producing or livestock or game or racing or sport animal.

15. A method of immunization, therapy, or decontamination of anthrax spores by inducing pre-mature spore germination with agents targeting the spore proteins of paragraphs 1-6.

16. The *Bacillus anthracis* spore protein of any of paragraphs 1-7 wherein the protein is obtained by a process comprising the steps of expressing the protein in a vector and purifying the protein.

17. The spore protein of paragraph 1, wherein the protein comprises the sequences depicted in FIG. 3A.

18. The spore protein of paragraph 2, wherein the protein comprises the sequences depicted in FIG. 3B.

19. The spore protein of paragraph 3, wherein the protein comprises the sequences depicted in FIG. 3C.

20. The spore protein of paragraph 1, wherein the protein comprises the sequences depicted in FIG. 3D.

21. A method of immunization in an animal and/or a method of inducing a systemic immune response or systemic therapeutic response to any of the 31 *B. anthracis* spore proteins described in Table 1.

22. A method of non-invasive immunization in an animal and/or a method of inducing a systemic immune response or systemic therapeutic response to a gene product from *Bacillus anthracis*, in an animal, comprising contacting skin, or nasal, oral, perlingual or buccal mucosa of the animal with a vector that contains and expresses a nucleic acid molecule encoding the gene product, in an amount effective to induce the response.

23. The method of paragraph 22 wherein the method comprises contacting the skin of the animal with the vector.

24. The method of paragraph 22 wherein the method comprises contacting the nasal mucosa with the vector.

25. The method of paragraph 22 wherein the method comprises contacting the oral or buccal or perlingual mucosa with the vector.

26. The method of paragraph 22 wherein the nucleic acid molecule is exogenous or heterologous to the vector.

27. The method of paragraph 22 wherein the response comprises a systemic immune response.

28. The method of paragraph 22 wherein the vector comprises and expresses an exogenous nucleic acid molecule encoding an epitope of interest.

29. The method of paragraph 22 wherein the vector comprises and expresses an antigen.

30. The method of paragraph 22 wherein the vector comprises and expresses a therapeutic product.

31. The method of paragraph 22 wherein the nucleic acid molecule encodes an epitope of interest and/or an antigen of interest and/or a nucleic acid molecule that stimulates and/or modulates an immunological response and/or stimulates and/or modulates expression comprising transcription and/or translation an endogenous and/or exogenous nucleic acid molecule.

32. The method of paragraph 26 wherein the exogenous nucleic acid molecule encodes one or more of an antigen or portion thereof, or one or more of an epitope of interest, from *Bacillus anthracis*.

33. The method of paragraph 26 wherein the exogenous nucleic acid molecule encodes one or more of: anthrax protective antigen, anthrax lethal factor, and anthrax edema factor.

34. The method of paragraph 31 wherein the response is induced by the vector expressing the nucleic acid molecule in the animal's cells.

35. The method of paragraph 34 wherein the cells comprise epidermal cells.

36. The method of paragraph 31 wherein the response comprises an immune response against *Bacillus anthracis*.

37. The method of paragraphs 22 wherein the animal is a vertebrate.

38. The method of paragraph 37 wherein the vertebrate is a mammal.

39. The method of paragraph 38 wherein the mammal is a human or a companion or domesticated or food- or feed-producing or livestock or game or racing or sport animal.

40. The method of paragraph 39 wherein the animal is a cow, a horse, a dog, a cat, a goat, a sheep, or a pig.

41. The method of paragraph 22 wherein the vector comprises one or more of a viral vector, a viral coat comprising a virus having some or all viral genes deleted therefrom, a bacterial vector, protozoan vector, a transposon, a retrotransposon, and a DNA vector.

42. The method of paragraph 41 wherein the vector comprises a recombinant vector.

43. The method of paragraph 42 wherein the vector comprises an adenovirus.

44. The method of paragraph 43 wherein the adenovirus is defective or deleted in its E1 and/or E3 and/or E4 region(s).

45. The method of paragraph 41, wherein the vector is an *Escherichia* bacterial vector.

46. The method of paragraph 45 wherein the *Escherichia* vector is *Escherichia coli*.

47. The method of paragraph 46 wherein the *Escherichia coli* is replication defective.

48. The method of paragraph 47 wherein the *Escherichia coli* is rendered replication defective by irradiation, antibiotics, fixatives, genetic substitutions or deletions, or gentle heat.

49. A method of inducing a systemic immune response or systemic therapeutic response to a gene product from *Bacillus anthracis*, in an animal, comprising topical and/or intranasal and/or mucosal and/or buccal and/or perlingual and/or oral administration of a vector comprising an adenovirus defective in its E1 and/or E3 and/or E4 region(s), wherein the adenovirus contains and expresses a nucleic acid molecule encoding the gene product for the response.

50. A method of inducing a systemic immune response or systemic therapeutic response to a gene product from *Bacillus anthracis*, in an animal, comprising topical and/or intranasal and/or mucosal and/or buccal and/or perlingual and/or oral administration of a vector comprising replication defective *Escherichia coli*, wherein the vector contains and expresses a nucleic acid molecule encoding the gene product for the response.

51. The method of paragraph 49 or 50 comprising topical administration.

52. The method of paragraph 49 or 50 comprising intranasal administration.

53. The method of paragraph 49 wherein the adenovirus is defective or deleted in its E1 and E3 regions.

54. The method of paragraphs 49 or 50 wherein the vector comprises an exogenous or heterologous nucleic acid molecule encoding the gene product for the response.

55. The method of paragraph 49 or 50 wherein the nucleic acid molecule is exogenous or heterologous and encodes an epitope of interest and the method is for inducing a systemic immunological response.

56. The method of paragraph 49 wherein the adenovirus is a human adenovirus.

57. The method of paragraph 49 wherein the adenovirus comprises a non-human adenovirus.

58. The method of paragraph 22, 49, or 50 wherein the vector is matched to, or a natural pathogen of, the animal.

59. The method of paragraph 22, 49, or 50 comprising applying a delivery device including the vector to the skin of the animal.

60. The method of paragraph 59 further comprising disposing the vector in and/or on the delivery device.

61. A pharmaceutical, vaccine, immunogenic, immunological or therapeutic composition for use in a method according to any one of paragraphs 22, 49, or 50 comprising the vector in a pharmaceutically acceptable carrier or diluent for administering the vector topically or mucosally or intranasally or buccally or perlingually or orally.

62. A kit for preparing a pharmaceutical, vaccine, immunogenic, immunological or therapeutic composition for use in a method according to any one of paragraphs 22, 49, or 50 comprising in a first container the vector and in a second container a pharmaceutically acceptable carrier or diluent for administering the vector topically or mucosally or intranasally or bucally or perlingually or orally; wherein the containers are optionally present in the same package or are in separate packages; and, the kit optionally contains instructions for admixture of the vector and the carrier or diluent and/or administration.

63. The kit of paragraph 62 further comprising a delivery device in a third container; wherein the third container is optionally present in the same package as one or both of the first and second containers or is in a package separate from the first and second containers; and, wherein kit optionally contains instructions for installing the vector or vector and carrier or diluent into or onto the delivery device and/or for administration or application of the delivery device.

64. The method of paragraph 23, wherein contacting the skin is performed in combination with the use of microneedles. All publications mentioned in the above specification are here incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in immunology or related fields are intended to be within the scope of the following claims.

TABLE 1

List of proteins identified in B. anthracis spores

| Spot | Protein | Accession No.[a] | Function | Note |
|---|---|---|---|---|
| 1-11 | SLH, S-layer homology domain | NP_654830 | Structural protein | *1262.57 (238-249)<br>*1277.65 (194-205)<br>*1405.77 (194-206)<br>65% sequence identity to S-layer protein precursor of B. licheniformis (JC4930) |
| 12 | Immune inhibitor A metalloprotease[+↑] | NP_843763 | Protease | 94% sequence identity to Immune inhibitor A precursor of B. cereus<br>*1465.77 (450-463) |
| 13 | Hypothetical protein 1[+↓] | NP_655179 | Unknown | Hypothetical protein predicted by GeneMark ™ with no homology to database entries<br>*958.49 (58-66)<br>*1008.46 (110-116) *1009.42 (95-104)<br>*1351.55 (92-104)<br>*1721.79 (117-131)<br>*1827.90 (134-149)<br>*2044.94 (132-463) |
| 14 | Hypothetical protein 2[+] | NP_655177 | Unknown | Hypothetical protein predicted by GeneMark ™ with no homology to database entries<br>*1182.65 (112-121)<br>*1210.63 (86-95) |
| 15, 16 | Hypothetical protein 3 [↓] | NP_655132 | Unknown | Hypothetical protein predicted by GeneMark ™ with no homology to database entries |
| 17 | Hypothetical protein 4[+] | NP_657537 | Unknown | Hypothetical protein predicted by GeneMark ™ with no homology to database entries |
| 18 | Hypothetical protein 5[+] | NP_658120 | Unknown | Hypothetical protein predicted by GeneMark ™ with no homology to database entries |
| 19 | GPR-like spore protease[+↑] | NP_846769 | Protease | 91% sequence identity to Spore protease of B. cereus; 67% identity to SASP degradation spore proteinase GPR precursor of B. subtilis (gi|98324) |
| 20 | Clp protease[+] | NP_653598 | Protease | EC 3.4.21.92[b]; 99% sequence identity to Clp Pl of B. thuringiensis |
| 21 | Alanine racemase[↓] | NP_842805 | Metabolism | EC 5.1.1.1; 96% sequence identity to Alanine racemase of B. cereus (NP_830132) |
| 22, 23 | Cysteine synthase A[+] | NP_842636 | Metabolism | EC 4.2.99.8; 89% sequence identity to Cysteine synthase of B. cereus (NP_829970) |
| 24 | Trigger factor[↑] | NP_846918 | Molecular Chaperone | EC 5.2.1.8; 90% sequence identity to Trigger factor of B. cereus |
| 25 | Heat shock protein 70[+] | NP_658346 | Molecular chaperone | 89% sequence identity to Hsp70 (DnaK) of B. cereus |
| 26 | Heat shock protein 60[+] | BAB68361 | Molecular chaperone | 85% sequence identity to Hsp60 of B. thuringiensis |
| 27 | TCP-1/cpn60 chaperonin family[↑] | NP_654198 | Molecular chaperone | 95% sequence identity to 60 kDa chaperonin GRoEL of B. cereus |
| 28 | Class I heat shock protein (chaperonin)[+] | NP_242212 | Molecular chaperone | 73% sequence identity to Class I heat shock protein (chaperonin) of B. subtilis (CAB14489) |
| 29 | Elongation factor G, C-terminus[+] | NP_654055 | Translation | 97% sequence identity to protein translation elongation factor G (EF-G) of B. cereus |
| 30 | Elongation factor Ts[+] | NP_657794 | Translation | 100% sequence identity to protein translation elongation factor Ts (EF-Ts) of B. cereus (NP_833545) |
| 31 | RNA polymerase, alpha chain, N-terminal domain[+] | NP_654079 | Transcription | EC 2.7.7.6; 96% sequence identity to DNA-directed RNA polymerase alpha chain of B. cereus (NP_830037) |
| 32 | Acetate kinase[+] | NP_658669 | Metabolism | EC 2.7.2.1; 92% sequence identity to acetate kinase of B. cereus (NP_834343) |
| 33, 34 | Delta-1-pyrroline-5-carboxylate dehydrogenase, putative/Aldehyde dehydrogenase family[+] | NP_654240 | Metabolism | EC 1.2.1.3; 99% sequence identity to Delta-1-pyrroline-5-carboxylate dehydrogenase of B. cereus (NP_830183) |
| 35 | Pyruvate dehydrogenase complex E1 component, alpha subunit[+] | NP_846421 | Metabolism | EC 1.2.4.1; 85% sequence identity to Pyruvate dehydrogenase complex E1 component, alpha subunit of B. cereus (NP_833692) |
| 36 | Pyruvate dehydrogenase complex E2 component, dihydrolipoamide acetyltransferase[+] | NP_846419 | Metabolism | EC 2.3.1.-; 82% sequence identity to Dihydrolipoamide acetyltransferase component of pyruvate dehydrogenase complex of B. cereus (NP_833690) |

TABLE 1-continued

List of proteins identified in *B. anthracis* spores

| Spot | Protein | Accession No.[a] | Function | Note |
|---|---|---|---|---|
| 37 | Alkyl hydroperoxide reductase, F subunit[+] | NP_842891 | Metabolism | EC 1.6.99.3; 92% sequence identity to Alkyl hydroperoxide reductase, F subunit of *B. cereus* (NP_830215) |
| 38 | Pyruvate dehydrogenase complex E3 component, dihydrolipoamide dehydrogenase[+] | NP_846418 | Metabolism | EC 1.8.1.4; 94% sequence identity to Dihyrolipoamide dehydrogenase of *B. cereus* (NP_833689) |
| 39 | Oxidoreductase, aldo/keto reductase family[+] | NP_845729 | Metabolism | EC 1.1.1.-; 92% sequence identity to 2,5-diketo-D-gluconic acid reductase of *B. cereus* (NP_833127) |
| 40 | Enolase[+] | NP_653583 | Metabolism | EC 4.2.1.11; 98% sequence identity to Enolase of *B. cereus* (NP_834403) |
| 41 | ATP synthase F1 beta subunit[+↑] | NP_847705 | Metabolism | EC 3.6.3.14; 95% sequence identity to ATP synthase beta chain of *B. cereus* (NP_834968) |
| 42 | Pyruvate dehydrogenase complex E1 component, beta subunit[+] | NP_846420 | Metabolism | EC 2.2.1.1; 95% sequence identity to Pyruvate dehydrogenase E1 component, beta subunity of *B. cereus* (NP_833691) |
| 43 | Fructose-bisphosphate aldolase class-II[+] | NP_653796 | Metabolism | EC 4.1.2.13; 95% sequence identity to Fructose-bisphosphate aldolase of *B. cereus* (NP_834997) |
| 44 | Triosephosphate isomerase[+] | NP_653585 | Metabolism | EC 5.3.1.1; 74% sequence identity to Triosephosphate isomerase of *B. megaterium* (JQ1955) |
| 45 | ATP synthase B/B' CF(0)[+] | NP_653766 | Metabolism | EC 3.6.3.14; 80% sequence identity to ATP synthase beta chain of *B. cereus* (NP_834972) |
| 46, 47 | Glyceraldehyde 3-phosphate dehydrogenase, C-terminal domain [+↑] | NP_653587 | Metabolism | EC 1.2.1.12; 94% sequence identity to Glyceraldehyde 3-phosphate dehydrogenase of *B. cereus* (NP_834805) |
| 48 | Sugar ABC transporter, ATP-binding protein[+↑] | NP_846171 | Metabolism | 92% sequence identity to nucleoside transport ATP-binding protein of *B. cereus* (NP_833512) |
| 49 | Band 7, SPFH domain/Band 7 family[+] | NP_654492 | Unknown | 76% sequence identity to Flotillin of *B. cereus* (NP_830375) |
| 50 | Alcohol dehydrogenase, zinc-binding dehydrogenase[+] | NP_654728 | Metabolism | EC 1.1.1.1; 86% sequence identity to Alcohol dehydrogenase of *B. cereus* (NP_830592) |

Ninety-six % (48/50) of protein spots were linked to the published *B. anthracis* genome sequence(Read 2002; Reed 2003); spot 26 was revealed as the *B. anthracis* HSP60 and spot 28 as the *B. halodurans* Class I HSP at the National Center for Biotechnology Information (NCBI) database available at the NCBI website.
[a]Accession No. are accessible at the NCBI database
[b](EC -.-.-.-) represents the enzyme commission number
*Observed m/z (predicted peptide sequencing) using Q-TOF 2
[+]Protein expression not previously reported in *B. anthracis*
[↑]Germination-associated increases
[↓]Germination-associated decreases

REFERENCES

Apuya, N. R., et al. (2001). "The *Arabidopsis* embryo mutant schlepperless has a defect in the chaperonin-60alpha gene." Plant Physiol 126: 717-730.

Ariel, N., A. Zvi, et al. (2003). "Genome-based bioinformatic selection of chromosomal *Bacillus anthracis* putative vaccine candidates coupled with proteomic identification of surface-associated antigens." Infect Immun 71(8): 4563-79.

Beall, F. A., M. J. Taylor, et al. (1962). "Rapid lethal effect in rats of a third component found upon fractionating the toxin of *Bacillus anthracis*." J Bacteriol 83: 1274-80.

Bradley, K. A., Mogridge, J., Mourez, M., Collier, R. J., and Young, J. A. (2001). "Identification of the cellular receptor for anthrax toxin." Nature 414: 225-229.

Casillas-Martinez, L., A. Driks, et al. (2000). "Lack of a significant role for the PerR regulator in *Bacillus subtilis* spore resistance." FEMS Microbiol Lett 188(2): 203-8.

Centers for Disease Control and Prevention (2001). "Investigation of Bioterrorism-related Anthrax: Connecticut, 2001." MMWR Morb Mortal Wkly Rep 50: 1077-1079.

Chatfield, S. N., I. G. Charles, et al. (1992). "Use of the nirB promoter to direct the stable expression of heterologous antigens in *Salmonella* oral vaccine strains: development of a single-dose oral tetanus vaccine." Bio/Technology 10: 888-892.

Coulson, N. M., M. Fulop, et al. (1994). "*Bacillus anthracis* protective antigen, expressed in *Salmonella typhimurium* SL 3261, affords protection against anthrax spore challenge." Vaccine 12(15): 1395-401.

Couture-Tosi. E., e. a. (2002). "Structural analysis and evidence for dynamic emergence of *Bacillus anthracis* S-layer networks." J Bacteriol 184: 6448-6456.

Dalhammar, G. and H. Steiner (1984). "Characterization of inhibitor A, a protease from *Bacillus thuringiensis* which degrades attacins and cecropins, two classes of antibacterial proteins in insects." Eur J Biochem 139: 247-252.

Demicheli, V., D. Rivetti, et al. (1998). "The effectiveness and safety of vaccines against human anthrax: a systematic review." Vaccine 16(9-10): 880-4.

Deuerling, E., A. Schulze-Specking, et al. (1999). "Trigger factor and DnaK cooperate in folding of newly synthesized proteins." Nature 400: 693-696.

Edlund, T., I. Siden, et al. (1976). "Evidence for two immune inhibitors from *Bacillus thuringiensis* interfering with the humoral defense system of saturniid pupae." Infect Immun 14: 934-941.

Friedlander, A. M. (1986). "Macrophages are sensitive to anthrax lethal toxin through an acid-dependent process." J Biol Chem 261(16): 7123-6.

Gao, H., X. Jiang, et al. (2002). "The Elbeta and E2 subunits of the *Bacillus subtilis* pyruvate dehydrogenase complex are involved in regulation of sporulation." J Bacteriol 184(10): 2780-8.

Gish, W. and D. J. States (1993). "Identification of protein coding regions by database similarity search." Nat Genet 3(3): 266-72.

Goeddel, D. V., H. L. Heyneker, et al. (1979). "Direct expression in *Escherichia coli* of a DNA sequence coding for human growth hormone." Nature 281(5732): 544-8.

Goeddel, D. V., D. G. Kleid, et al. (1979). "Expression in *Escherichia coli* of chemically synthesized genes for human insulin." Proc Natl Acad Sci USA 76(1): 106-10.

Grandvalet, C., Gominet, M., and Lereclus, D. (2001). "Identification of genes involved in the activation of the *Bacillus thuringiensis* inhA metalloprotease gene at the onset of sporulation." Microbiology 147: 1805-1813.

Gu, M. L., S. H. Leppla, et al. (1999). "Protection against anthrax toxin by vaccination with a DNA plasmid encoding anthrax protective antigen." Vaccine 17(4): 340-4.

Hanna, P. C., D. Acosta, et al. (1993). "On the role of macrophages in anthrax." Proc Natl Acad Sci USA 90(21): 10198-201.

Hanson, R. S., J. Blicharska, et al. (1964). "RElationship between the tricarboxylic acid cycle enzymes and sporulation of *B. subtilis*." Biochem Biophys Res Commun 17: 1-11.

Huang, C. M., et al. (2003). "Comparative Proteomic Profiling of Murine Skin." J Invest Dermatol 121: 51-64.

Huang, C.-M., K. W. Foster, et al. (2004). "Identification of *Bacillus anthracis* proteins associated with germination and early outgrowth by proteomic profiling of anthrax spores." Proteomics In Press.

Huxsoll, D. L., C. D. Parrott, et al. (1989). "Medicine in defense against biological warfare." Jama 262(5): 677-9.

Inglesby, T. V., O'Toole, T., Henderson, D. A., Bartlett, J. G., Ascher, M. S., Eitzen, E., Friedlander, A. M., Gerberding, J., Hauer, J., Hughes, J., McDade, J., Osterholm, M. T., Parker, G., Perl, T. M., Russell, P. K., Tonat, K., and Biodefense, W. G. o. C. (2002). "Anthrax as a biological weapon, 2002: updated recommendations for management." JAMA 287: 2236-2252.

Itakura, K., T. Hirose, et al. (1977). "Expression in *Escherichia coli* of a chemically synthesized gene for the hormone somatostatin." Science 198(4321): 1056-63.

Ivanova, N., A. Sorokin, et al. (2003). "Genome sequence of *Bacillus cereus* and comparative analysis with *Bacillus anthracis*." Nature 423(6935): 87-91.

Ivins, B. E., S. L. Welkos, et al. (1992). "Immunization against anthrax with *Bacillus anthracis* protective antigen combined with adjuvants." Infect Immun 60(2): 662-8.

Ivins, B. E. e. a. (1996). Salisbury Med Bull Supp 87: 125-126.

Joellenbeck, L. M., L. L. Zwanziger, et al. (2002). The Anthrax Vaccine. Washington, D.C., National Academy Press.

Kanda-Nambu, K., Y. Yasuda, et al. (2000). "Isozymic nature of spore coat-associated alanine racemase of *Bacillus subtilis*." Amino Acids 18: 375-387.

Klimpel, K. R., N. Arora, et al. (1994). "Anthrax toxin lethal factor contains a zinc metalloprotease consensus sequence which is required for lethal toxin activity." Mol Microbiol 13(6): 1093-100.

Lai, E. M., N. D. Phadke, et al. (2003). "Proteomic analysis of the spore coats of *Bacillus subtilis* and *Bacillus anthracis*." J. Bacteriol. 185: 1443-1454.

Lemos, J. A. and R. A. Burne (2002). "Regulation and Physiological Significance of ClpC and ClpP in *Streptococcus mutans*." J. Bacteriol 184(22): 6357-66.

Leppla, S. H. (1982). "Anthrax toxin edema factor: a bacterial adenylate cyclase that increases cyclic AMP concentrations of eukaryotic cells." Proc Natl Acad Sci USA 79(10): 3162-6.

Leppla, S. H. e. a. (1990). Salisbury Med Bull Supp 68: 41-43.

Liu, H., N. H. Bergman, et al. (2004). "Formation and composition of the *Bacillus anthracis* endospore." J. Bacteriol 186(1): 164-78.

Liu, H., N. H. Bergman, et al. (2004). "Formation and composition of the *Bacillus anthracis* endospore." J. Bacteriol. 186: 164-178.

Lovgren, A., Zhang, M., Engstrom, A., Dalhammar, G., and Landen, R. (1990). "Molecular characterization of immune inhibitor A, a secreted virulence protease from *Bacillus thuringiensis*." Mol. Microbiol. 4: 2137-2146.

Marino, M., T. Hoffmann, et al. (2000). "Changes in protein synthesis during the adaptation of *Bacillus subtilis* to anaerobic growth conditions." Microbiology 146 (Pt 1): 97-105.

Mock, M. and A. Fouet (2001). "Anthrax." Annu Rev Microbiol 55: 647-71.

Murakami, P., E. Pungor, et al. (2002). "A single short stretch of homology between adenoviral vector and packaging cell line can give rise to cytopathic effect-inducing, helper-dependent E1-positive particles." Hum Gene Ther 13(8): 909-20.

Osterhaus, A. D. and P. de Vries (1992). "Vaccination against acute respiratory virus infections and measles in man." Immunobiology 184(2-3): 180-92.

Perkins, D. N., D. J. Pappin, et al. (1999). "Probability-based protein identification by searching sequence databases using mass spectrometry data." Electrophoresis 20: 3551-3567.

Pitt, M. L. M. e. a. (1996). Salisbury Med Bull Supp 87: 130.

Ponnuraj, K., S. Kelly, et al. (2000). "Crystallization and preliminary diffraction studies of a truncated form of a novel protease from spores of *Bacillus megaterium*." Acta Crystallogr D Biol Crystallogr 56: 70-72.

Price, B. M., A. L. Liner, et al. (2001). "Protection against anthrax lethal toxin challenge by genetic immunization with a plasmid encoding the lethal factor protein." Infect Immun 69(7): 4509-15.

Price, B. M., A. L. Liner, et al. (2001). "Protection against anthrax lethal toxin challenge by genetic immunization with a plasmid encoding the lethal factor protein." Infect. Immun. 69: 4509-4515.

Queen, C. (1983). "A vector that uses phage signals for efficient synthesis of proteins in *Escherichia coli*." J Mol Appl Genet 2(1): 1-10.

Read, T. D., et al. (2002). "Comparative genome sequencing for discovery of novel polymorphisms in *Bacillus anthracis*." Science 296: 2028-2033.

Read, T. D., S. N. Peterson, et al. (2003). "The genome sequence of *Bacillus anthracis* Ames and comparison to closely related bacteria." Nature 423(6935): 81-6.

Rhie, G. E., M. H. Roehrl, et al. (2003). "A dually active anthrax vaccine that confers protection against both bacilli and toxins." Proc Natl Acad Sci USA 100(19): 10925-30.

Sanchez-Salas, J. L., M. Santiago-Lara, L., et al. (1992). "Properties of *Bacillus megaterium* and *Bacillus subtilis* mutants which lack the protease that degrades small, acid-soluble proteins during spore germination." J Bacteriol 174: 807-814.

Sanchez-Salas, J. L. and P. Setlow (1993). "Proteolytic processing of the protease which initiates degradation of small, acid-soluble proteins during germination of *Bacillus subtilis* spores." J Bacteriol 75: 2568-2577.

Sa-Nogueira, I. and S. S. Ramos (1997). "Cloning, functional analysis, and transcriptional regulation of the *Bacillus subtilis* araE gene involved in L-arabinose utilization." J Bacteriol 179: 7705-7711.

Sellman, B. R., M. Mourez, et al. (2001). "Dominant-negative mutants of a toxin subunit: an approach to therapy of anthrax." Science 292(5517): 695-7.

Shi, Z., D. T. Curiel, et al. (1999). "DNA-based non-invasive vaccination onto the skin." Vaccine 17: 2136-2141.

Shi, Z., M. Zeng, et al. (2001). "Protection against tetanus by needle-free inoculation of adenovirus-vectored nasal and epicutaneous vaccines." J. Virol. 75: 11474-11482.

Shi, Z., Zeng, M., Yang, G., Siegel, F., Cain, L. J., Van Kampen, K. R., Elmets, C. A., and Tang, D. C. (2001). "Protection against tetanus by needle-free inoculation of adenovirus-vectored nasal and epicutaneous vaccines." J. Virol. 75: 11474-11482.

Shlyakhov, E. N. and E. Rubinstein (1994). "Human live anthrax vaccine in the former USSR." Vaccine 12(8): 727-30.

Singh, Y., B. E. Ivins, et al. (1998). "Study of immunization against anthrax with the purified recombinant protective antigen of *Bacillus anthracis*." Infect Immun 66(7): 3447-8.

Singh, Y., K. R. Klimpel, et al. (1999). "Oligomerization of anthrax toxin protective antigen and binding of lethal factor during endocytic uptake into mammalian cells." Infect Immun 67(4): 1853-9.

Smith, H. and J. Keppie (1954). "Observations on experimental anthrax; demonstration of a specific lethal factor produced in vivo by *Bacillus anthracis*." Nature 173 (4410): 869-70.

Stanley, J. L. and H. Smith (1961). "Purification of factor I and recognition of a third factor of the anthrax toxin." J Gen Microbiol 26: 49-63.

Steichen, C., P. Chen, et al. (2003). "Identification of the immunodominant protein and other proteins of the *Bacillus anthracis* exosporium." J Bacteriol 185(6): 1903-10.

Swain, S. L., H. Hu, et al. (1999). "Class II-independent generation of CD4 memory T cells from effectors." Science 286(5443): 1381-3.

Swartz, M. N. (2001). "Recognition and management of anthrax—an update." N Engl J Med 345(22): 1621-6.

Tan, Y., N. R. Hackett, et al. (2003). "Protective immunity evoked against anthrax lethal toxin after a single intramuscular administration of an adenovirus-based vaccine encoding humanized protective antigen." Hum Gene Ther 14(17): 1673-82.

Tang, D. C., M. DeVit, et al. (1992). "Genetic immunization is a simple method for eliciting an immune response." Nature 356(6365): 152-4.

Tang, D. C., Z. Shi, et al. (1997). "Vaccination onto bare skin." Nature 388(6644): 729-30.

Todd, S. J., A. J. Moir, et al. (2003). "Genes of *Bacillus cereus* and *Bacillus anthracis* encoding proteins of the exosporium." J Bacteriol 185(11): 3373-8.

Tovar-Rojo, F., R. M. Cabrera-Martinez, et al. (2003). "Studies on the mechanism of the osmoresistance of spores of *Bacillus subtilis*." J. Appl. Microbiol. 95: 167-179.

Turnbull, P. C., M. G. Broster, et al. (1986). "Development of antibodies to protective antigen and lethal factor components of anthrax toxin in humans and guinea pigs and their relevance to protective immunity." Infect Immun 52(2): 356-63.

Turnbull, P. C., S. H. Leppla, et al. (1988). "Antibodies to anthrax toxin in humans and guinea pigs and their relevance to protective immunity." Med Microbiol Immunol (Berl) 177(5): 293-303.

Ulmer, J. B., J. J. Donnelly, et al. (1993). "Heterologous protection against influenza by injection of DNA encoding a viral protein." Science 259(5102): 1745-9.

van Ginkel, F. W., J. R. McGhee, et al. (1997). "Adenoviral gene delivery elicits distinct pulmonary-associated T helper cell responses to the vector and to its transgene." J Immunol 159(2): 685-93.

Walter, T. and A. Aronson (1999). "Specific binding of the E2 subunit of pyruvate dehydrogenase to the upstream region of *Bacillus thuringiensis* protoxin genes." J Biol Chem 274(12): 7901-6.

Welkos, S., S. Little, et al. (2001). "The role of antibodies to *Bacillus anthracis* and anthrax toxin components in inhibiting the early stages of infection by anthrax spores." Microbiology 147: 1677-1685.

Welkos, S. L. and A. M. Friedlander (1988). "Comparative safety and efficacy against *Bacillus anthracis* of protective antigen and live vaccines in mice." Microb Pathog 5(2): 127-39.

Xiang, Z. Q., Y. Yang, et al. (1996). "A replication-defective human adenovirus recombinant serves as a highly efficacious vaccine carrier." Virology 219(1): 220-7.

U.S. Pat. No. 5,990,091
U.S. Pat. No. 6,004,802
U.S. Pat. No. 6,042,838
WO 95/60164
WO 95/60164
95/53940

What is claimed is:

1. A non-invasive method of inducing a protective immune response against inhalation anthrax in a mammal, comprising:
administering intranasally to the mammal at least $10^7$ pfu of a non-replicating adenovirus vector that contains and expresses a nucleic acid encoding B. anthracis protective antigen,
wherein induction of the protective immune response provides protection against challenge with intranasal inhalation of B. anthracis spores, and thereby non-invasively inducing a protective immune response against inhalation anthrax in the mammal.

2. The method of claim 1, wherein the mammal is a companion animal, a domesticated animal, a food- or feed-producing animal, a livestock animal, a game animal, a racing animal, or a sport animal.

3. The method of claim 1, wherein the mammal is a cow, a horse, a dog, a cat, a goat, a sheep, or a pig.

4. The method of claim 1, wherein the mammal is a human.

5. The method of claim 1, wherein the vector is E1 and/or E3 defective adenovirus serotype 5 (Ad5).

6. The method of claim 1, wherein the B. anthracis protective antigen is PA83.

7. A non-invasive method of inducing a systemic immune response against B. anthracis in a mammal, comprising:
administering intranasally to the mammal at least $10^7$ pfu of a non-replicating adenovirus vector that contains and expresses a nucleic acid encoding B. anthracis protective antigen,
wherein the mammal produces toxin-neutralizing antibodies in response to the intranasal administration of the adenovirus vector encoding B. anthracis protective antigen,
wherein the toxin-neutralizing antibodies provide a protective immune response against challenge with intranasal inhalation of B. anthracis spores, and thereby non-invasively inducing a systemic protective immune response against B. anthracis in the mammal.

8. The method of claim 7, wherein the vector is E1 and/or E3 defective adenovirus serotype 5 (Ad5).

9. The method of claim 7, wherein the mammal is a companion animal, a domesticated animal, a food- or feed-producing animal, a livestock animal, a game animal, a racing animal, or a sport animal.

10. The method of claim 7, wherein the mammal is a cow, a horse, a dog, a cat, a goat, a sheep, or a pig.

11. The method of claim 7, wherein the mammal is a human.

12. The method of claim 7, wherein the B. anthracis protective antigen is PA83.

* * * * *